United States Patent

Spangler

[11] Patent Number: 6,124,592
[45] Date of Patent: Sep. 26, 2000

[54] ION MOBILITY STORAGE TRAP AND METHOD

[75] Inventor: Glenn E. Spangler, Lutherville, Md.

[73] Assignee: Technispan LLC, Pikesville, Md.

[21] Appl. No.: 09/040,282

[22] Filed: Mar. 18, 1998

[51] Int. Cl.[7] ............................. B01D 59/44; H01J 49/00
[52] U.S. Cl. ........................................... 250/287; 250/282
[58] Field of Search ................................... 250/287, 282, 250/292, 281

[56] References Cited

U.S. PATENT DOCUMENTS

| | | |
|---|---|---|
| Re. 34,000 | 7/1992 | Syka et al. . |
| 2,939,952 | 6/1960 | Paul et al. . |
| 2,950,389 | 8/1960 | Paul et al. . |
| 3,699,333 | 10/1972 | Cohen et al. . |
| 4,390,784 | 6/1983 | Browning et al. . |
| 4,540,884 | 9/1985 | Sptafford et al. . |
| 4,736,101 | 4/1988 | Syka et al. . |
| 4,855,595 | 8/1989 | Blanchard ............................. 250/287 |
| 4,882,484 | 11/1989 | Franzen et al. . |
| 4,975,577 | 12/1990 | Franzen et al. . |
| 5,028,777 | 7/1991 | Franzen et al. . |
| 5,170,054 | 12/1992 | Franzen . |
| 5,180,914 | 1/1993 | Davis et al. ............................. 250/287 |
| 5,200,614 | 4/1993 | Jenkins . |
| 5,283,436 | 2/1994 | Wang . |
| 5,291,017 | 3/1994 | Wang et al. ............................. 250/292 |
| 5,331,157 | 7/1994 | Franzen . |
| 5,338,931 | 8/1994 | Spangler et al. . |
| 5,386,113 | 1/1995 | Franzen et al. . |
| 5,420,424 | 5/1995 | Carnahan et al. ...................... 250/287 |
| 5,468,958 | 11/1995 | Franzen et al. . |
| 5,569,917 | 10/1996 | Buttrill, Jr. et al. . |
| 5,576,540 | 11/1996 | Jolliffe ................................... 250/292 |
| 5,693,941 | 12/1997 | Barlow et al. ......................... 250/292 |
| 5,714,755 | 2/1998 | Wells ..................................... 250/292 |

OTHER PUBLICATIONS

J.O. Hirschfelder, C.F. Curtiss and R.B. Bird, "Molecular Theory of Gases and Liquids," Wiley: New York, 1954, table of contents and chap. 3, sec. 10f(pp. 222–225).

E.A. Mason and H.W. Schamp, "Mobility of Gaseous Ions in Weak Electric Fields," Annals of Physics (NY), vol. 4, 1958, pp. 233–270.

U. von Zahn, "Monopole Spectrometer, a New Electric Field Mass Spectrometer," Review of Scientific Instruments, vol. 34, No. 1, 1963, 1–4.

M.H. Studier, "Continuous Ion Source for a Time–of–Flight Mass Spectrometer," Review of Scientific Instruments, vol. 34, No. 12, 1963, 1367–1370.

E.A. Mason, H. O'Hara and F.J. Smith, "Mobilities of Polyatomic Ions in Gases: Core Model," Journal of Physics B: Atomic and Molecular Physics, vol. 5, 1972, 169–176.

R.F. Bonner, G. Lawson and J.F.J. Todd, "Ion–Molecule Reaction Studies with a Quadrupole Ion Storage Trap," International Journal of Mass Spectromety and Ion Physics, vol. 10, 1972/1973, 197–203.

J.H. Schummers, G.M. Thomson, D.R. James, I.R. Gatland and E.W. McDaniel, "Mobilities and Longitudinal–Diffusion Coefficients of Mass–Identified Positive Ions in Carbon Monoxide Gas," Physical Review A, vol. 7, No. 2, 1973, 683–688.

E.C. Horning, M.G. Horning, D.I. Carroll, I.Dzidic and R.N. Stillwell, "New Picogram Detection System Based on a Mass Spectrometer with a, External Ionization Source at Atomspheric Pressure," Analytical Chemistry, vol. 45, 1973, 936–943.

(List continued on next page.)

*Primary Examiner*—Bruce C. Anderson
*Attorney, Agent, or Firm*—Nikaido, Marmelstein, Murray & Oram LLP

[57] ABSTRACT

An apparatus and method to separate and store ions by exploiting mobility characteristics of the ions. A sample is introduced into a trap volume and ionized. The ions are separated according to their mobility characteristics by applying an electric field to the trap volume. The ions thus migrate to equilibrium positions in the trap volume due to a difference in mobilities and to changes in the electric field. The ions may be sequentially scanned from the trap by changing the electric field. The identity of ions within the trap may then be determined.

75 Claims, 46 Drawing Sheets

OTHER PUBLICATIONS

S.C. Terry, "A Gas Chromatography System Fabricated on a Silicon Wafer using Integrated Circuit Technology," PhD Dissertation, Stanford University, CA, 1975.

R.E. Mather, G. Lawson, J.F.J. Todd and J.M.B. Bakker, "The Quadrupole Ion Storage Trap (Quistor) as a Low–Pressure Chemical Ionisation Source for a Magnetic Sector Mass Spectrometer," International Journal of Mass Spectrometry and Ion Physics, vol. 28, 1978, 347–364.

S.C. Terry, J.H. Jerman and J.B. Angell, "A Gas Chromatographic Air Analyzer Fabricated on a Silicon Wafer," IEEE Transactions on Electron Devices, vol. ED–26, No. 12, Dec. 1979, 1880–1886.

J.E. Fulford, D.–N. Hoa, R.J. Hughes, R.E. March, R.F. Bonner and G.J. Wong, "Radio–Frequency Mass Selective Excitation and Resonant Ejection on Ions in a Three–Dimensional Quadrupole Ion Trap," Journal of Vacuum Science and Technolgy, vol. 17, No. 4, 1980, 829–835.

J.B. Angell, S.C. Terry and P.W. Barth, "Silicon Micromechanical Devices," Scientific American, vol. 248, No. 4, Apr. 1983, 44–55.

E.W. McDaniel, "Atomic Collisions: Electron and Photon Projectiles," Wiley: New York, 1989, table of contents and pp. 27–33.

R.G. Brewer, R.G. DeVoe and R. Kallenbach, "Planar Ion Microtraps," Rapid Communication in Physical Review A, vol. 46, 1992, pp. R6781–6784.

I.A. Buryakov, E.V. Krylov, E.G. Nazarov and U. Kh. Rasulev, "A New Method of Separation of Multi–Atomic Ions by Mobility at Atmospheric Pressure using a High–Frequency Amplitude–Asymmetric Strong Electric Field," International Journal of Mass Spectrometry and Ion Processes, vol. 128, 1993, pp. 143–148.

D. Wittmer, Y.H. Chen, B.K. Luckenbill and H.H. Hill, Jr., "Electrospray Ionization Ion Mobility Spectrometry," Analyical Chemistry, vol. 66, 1994, pp. 2348–2355.

R.R. Reston and E.S. Kolesar, Jr., "Silicon–Micromachined Gas Chromatography Systems Used to Separte and Detect Ammonia and Nitrogen Dioxide—Parts I and II," Journal of Microelectromechanical Systems, vol. 3, No. 4, Dec. 1994, 134–154.

G.E. Spangler, "Theoretical Investigations into the Application of Momentum Transfer Theory to The Motion of Ions in the Presence of RF Fields," Poster presentation at the Scientific Conference on chemical and Biological Defense Research, ERDEC, Aberdeen Proving Grounds, MD, Nov. 1995.

Q. Ji, M.R. Davenport, C.G. Enke and J.F. Holland, "A Segmented Ring, Cylindrical Ion Trap Source for Time–of–Flight Mass Spectrometry," Journal of the American Society for Mass Spectrometry, vol. 7, 1996, pp. 1009–1017.

G.E. Spangler, "I. Further Development of Momentum Transfer Theory for Ion Transport in Ion Mobility Spectrometry," Presented at the Fifth International Workshop of Ion Mobility Spectrometry, Jackson, Wyoming, Aug. 1996.

G.E. Spangler, "II. Theory for the Selective Transport of Ions in the Presence of RF Fields," Presented at the Fifth International Workshop on Ion Mobility Spectrometry, Jackson, Wyoming, Aug. 1996.

$$\Phi = (U + V\cos\omega t)\left[\frac{r^2 + 2(z_0^2 - z^2)}{r_0^2 + 2z_0^2}\right]$$

$$E_r = -(U + V\cos\omega t)\left[\frac{2r}{r_0^2 + 2z_0^2}\right]$$

$$E_z = (U + V\cos\omega t)\left[\frac{4z}{r_0^2 + 2z_0^2}\right]$$

$$\Phi = (U + V\cos\omega t)\left[\frac{2z^3 - 3r^2z}{4z_0^3}\right]$$

$$E_r = (U + V\cos\omega t)\left[\frac{3rz}{2z_0^3}\right]$$

$$E_z = (U + V\cos\omega t)\left[\frac{3r^2 - 6z^2}{4z_0^3}\right]$$

$$\Phi = (U + V\cos\omega t)\left[\frac{r^4}{2r_0^4} + \frac{z^4}{2z_0^4} - \frac{4z_0^2 + 3r_0^2}{r_0^4 + 2r_0^2 z_0^2}\frac{r^2 z^2}{z_0^2}\right]$$

$$E_r = (U + V\cos\omega t)\left[\frac{8z_0^2 + 6r_0^2}{r_0^4 + 2r_0^2 z_0^2}\frac{rz^2}{z_0^2} - \frac{2r^3}{r_0^4}\right]$$

$$E_z = (U + V\cos\omega t)\left[\frac{8z_0^2 + 6r_0^2}{r_0^4 + 2r_0^2 z_0^2}\frac{r^2 z}{z_0^2} - \frac{2z^3}{z_0^4}\right]$$

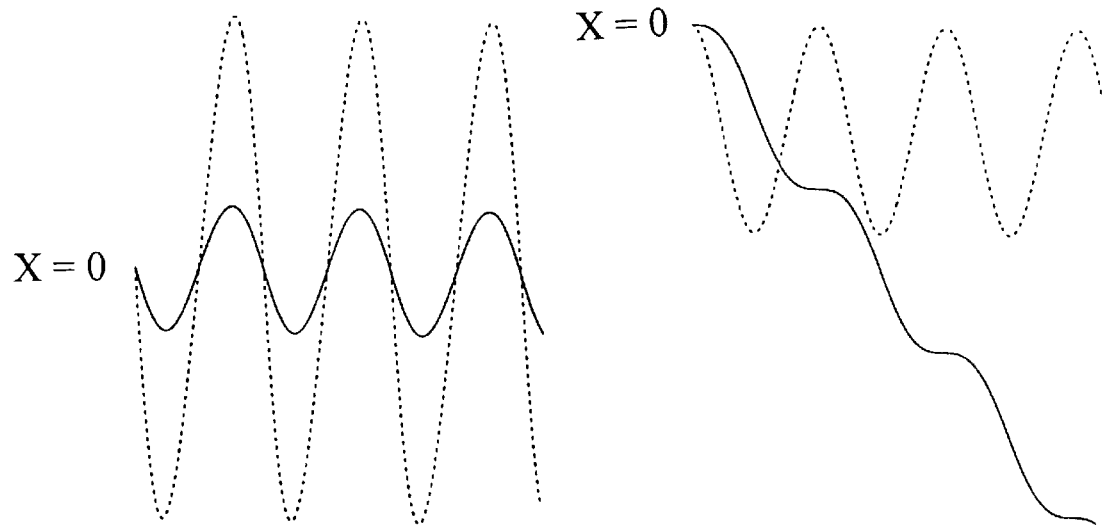
FIGURE 12A  FIGURE 12B
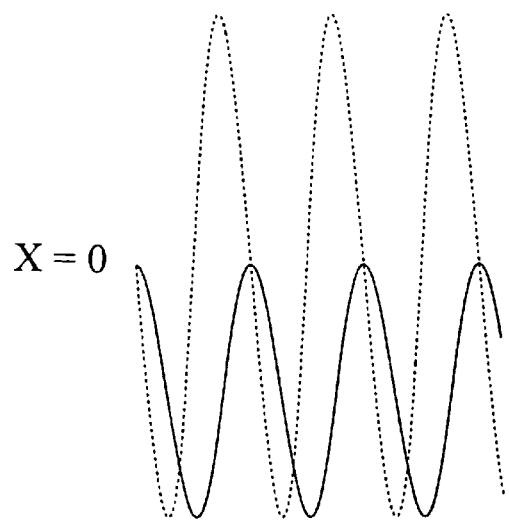 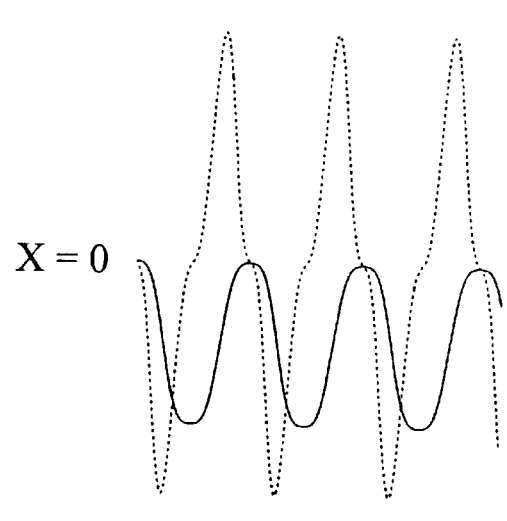
FIGURE 12C  FIGURE 12D

Plot of the R-Solution

Plot of the Z-Solution

Plot of the R-Solution

Plot of the Z-Solution

Plot of the R-Solution

Plot of the Z-Solution

Plot of the R-Solution

Plot of the Z-Solution

Plot of the R-Solution

Plot of the Z-Solution

Plot of the R-Solution

Plot of the Z-Solution

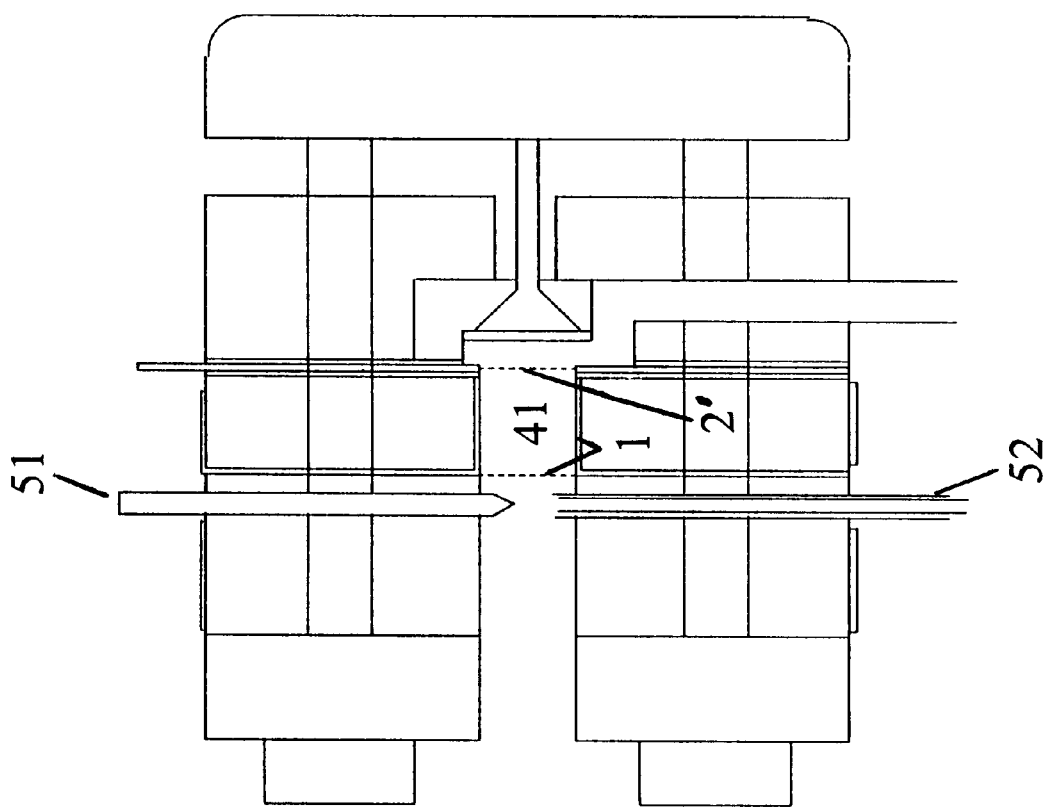

ION MOBILITY STORAGE TRAP AND METHOD

FIELD OF THE INVENTION

The invention relates to ion mobility spectrometry to separate and store ions in gases using an asymmetric AC potential.

BACKGROUND OF THE INVENTION

Several devices are known that ionize a gaseous sample and analyze the product ions for the molecular makeup of the sample. The devices fall into two categories: those that operate under vacuum and those that operate under pressure conditions. The devices that operate under vacuum are know as mass spectrometers and separate ions according to charge-to-mass ratios using a combination of electromagnetic fields. The devices that operate under pressure are known as ion mobility spectrometers and separate ions according to mobilities through a drift gas in a constant electric field. Generally, mass spectrometers require a vacuum better than $10^{-3}$ mm Hg to eliminate the adverse effects of collisions between ions and neutral gas molecules. This is unlike ion mobility spectrometry where pressures greater than $10^{-3}$ mm Hg are needed to assure that collisions between the ions and neutral gas molecules firmly establish mobility values. Due to the absence of collisions in mass spectrometry, the ions can gain considerable energy as they respond to the imposed electromagnetic fields. In ion mobility spectrometry, the energy gained by the ions is rapidly dissipated by collisions between the ions and neutral gas molecules. One consequence of this difference in ion energy between mass spectrometry and ion mobility spectrometry is that the energetic ions of mass spectrometry do not follow electric field lines, while the thermal ions of ion mobility spectrometry do. Because of this difference, attempts to separate ions using one technique in the pressure regime of the other is generally unsuccessful. On the other hand, there are enough similarities between mass spectrometry and ion mobility spectrometry to encourage exploitation of common features.

The technique of ion mobility spectrometry (IMS) was first disclosed in U.S. Pat. No. 3,699,333 which issued on Oct. 17, 1972 to M. J. Cohen, D. I. Carroll, R. F. Wemlund and W. D. Kilpatrick. It was originally conceived as a method to analyze and detect organic vapors in a gas mixture. FIG. 1 shows a simplified IMS detector cell. It contains two regions: a reaction (or reactor) region where the ions are ionized, and a drift (or drift tube) region where the ions are separated. The ionization and separation processes occur under a wide range of pressure to, conditions, but the preferred operating pressure in U.S. Pat. No. 3,699,333 was atmospheric pressure. In the reaction region, the sample is either ionized directly by using ultraviolet radiation from a photoionization source, electrospraying the ions as a mist into the ionizer, etc.; or indirectly by reacting with an intermediate set of reactant ions (designated by $R^\pm$ in FIG. 1). The indirect method of ionization is known as chemical ionization and the reactant ions are created by using a radioactive source (e.g., $Ni^{63}$, $Am^{241}$, tritium, etc.), a corona discharge source, a thermionic emitter of alkali ions, or another primary source of ions.

The nature of the reactant ions generated by the ionization source depends on the composition of the carrier gas used to transport sample into the reactor of the ion mobility spectrometer. This dependency can be used to selectively ionize a specific component in a sample matrix by adjusting the composition of the carrier gas. This is accomplished by doping the carrier gas with a low level of a chemical reagent, such as acetone, a chlorinated solvent, methyl salicylate, etc. The reactant ions then become a protonated di,acetones a chloride anion or a protonated monomer of methyl salicylate, etc. that react differently the ample.

While the reactant ions and product ions (designated by $P^\pm$ in FIG. 1) can be positively or negatively charged, the polarity of the ions that are extracted from the reactor and analyzed by the drift tube depends upon the directionality of the electric field applied to the drift tube. If the ionization source is biased positive relative to the ion collector, positive ions are extracted from the reactor and analyzed by the drift tube for mobility. If the ionization source is biased negative relative to the ion collector, negative ions are extracted from the reactor and analyzed by the drift tube for mobility. If no electric field is applied, the positive and negative ions recombine, and are otherwise lost for analysis by the drift tube.

A shutter grid positioned between the reactor and the drift tube provides a means whereby a localized concentration of ions is extracted from the reactor and introduced into the drift tube. Typically this shutter grid consists of a planar array of parallel wires with neighboring wires electrically independent. When the two sets of electrically independent wires are at the same potential, the ions pass freely through the grid and enter the drift tube. When the two sets of neighboring wires are at different potentials, the ions are captured by the grid and are denied entry into the drift tube. Ion injection into the drift tube is accomplished by momentarily removing the blocking potential from the shutter grid. Once inside the drift tube and exposed to the drift field applied to the drift tube, the ions migrate toward an ion collector (or Faraday plate) located at the other end of the drift tube. When the ions arrive at the collector, their drift time is recorded and correlated with the composition of the original sample delivered to the reactor.

The IMS technique, as described above, has several limitations. These include:

1. The basic limits of detection are restricted to about ten picograms or ten parts per trillion due to build up of space charge in the reactor. There is no capability of concentrating and storing ions.
2. Ion mobilities are sensitive to the composition of the drift gas, and decrease as the ion clusters with water vapor or other polar compounds. Ions attached to contaminant gases have different mobilities, making it difficult to identify the ions.
3. Miniature IMS sensors are plagued by low total ion currents (the ion current collected by the ion collector when the shutter grid is biased open continuously) that limit the dynamic range of the device.

U.S. Pat. No. 5,200,614 which issued on Apr. 6, 1993 to A. Jenkins and W. J. McGann describes an "ion trap mobility spectrometer" that attempts to remove one of the above limitations and improves the limits of detection of IMS for electrophilic compounds (e.g., nitro-compounds used as explosives). A schematic representation of their device is shown in FIG. 2. The two halves of the shutter grid are separated to create a field-free ion storage region within the device. When the two grids (E1 and E2 in FIG. 2) are at the same potential, the ions entering the ion storage region from the reactor become "trapped" (i.e., lie motionless). By momentarily applying a high potential between grids E1 and E2 ($V_3$ in FIG. 2), the "trapped" ions are injected into the drift tube. The ion storage region, therefore, behaves like a pulsed reactor for the IMS. When compared to the reactor of a conventional IMS, this pulsed reactor has the advantage that it increases the reaction time for ionization; and in the case where electron capture processes are important, thermalizes the reacting electrons. On the other hand, the disadvantages are that space charge can more easily build up in the ion storage region. Like conventional IMS, the drift times for the ions in the affected ion trap mobility spetrometer are by the composition of the carrier gas flowing through the drift region, and the total ion current decreases when attempts are made to miniaturize the cell.

Disclosed in Russian Inventor's Certificate No. 9666583 is another method for separating ions according to mobility. The parallel plate ion separator for this invention is shown in FIG. 3 where the ion flow (induced by a drift gas) is from left to right. A transverse asymmetric AC field is applied across the electrodes of the separator to excite a perpendicular micromotion in the ions as they move in the average direction of the flowing drift gas. The amplitude of the micromotion is proportional to the electric field strength through a mobility coefficient K. The relationship $v_d=KE$ is a vector relationship between the drift velocity $v_d$ of the ion and the electric field E. Unlike conventional IMS where ion separation is accomplished using relatively low electric field strengths (e.g., 150–250 volts/cm), higher field strengths are required to successfully separate the ions in the Russian invention. E. A. Mason and E. W. McDaniel in their book entitled "Transport Properties of Ions in Gases" (Wiley, New York, 1988) teach that the mobility coefficient K is a function of the electric field E. An approximate expression for the functional dependence is $K(E)=K_0+K_2E^2+K_4E^4+\ldots$, where the $K_i$'s are coefficients dependent on the ion species under consideration. Therefore when an ion is exposed to an asymmetric AC potential that is oscillating between adequately high and low values, the ion experiences different mobilities when traveling in one direction compared to the other. This causes; the ions to move more in one direction than another, and be neutralized when they collide with the electrodes of the Russian invention. By adding a DC component to the asymmetric potential, the path taken by the ions can be altered; and depending on the combination of the DC and asymmetric AC potentials applied, certain ions can be directed towards an ion collector. Since the difference in mobilities created by the asymmetric field is dependent on the type of ion being analyzed, ion separation is possible.

In a paper published in the *International Journal of Mass Spectrometry and Ion Processes*; volume 128 (1993), pp. 143–148; I. A. Buryakov, E. V. Krylov, E. G. Nazarov and U. Kh. Rasulev further describe the method of Certificate No. 9666583. They state that the ion separation is performed in a dense gas (e.g., air at 760 mm Hg) using a 2 megahertz RF potential. The waveform for the RF potential is rectangular with a period of $T=t_1+t_2$ ($t_1 \ll t_2$); the absolute value for the positive semi-period, $t_1(E_{max})$, being much less than the absolute value for the negative semi-period, $t_2(E_{min})$, and the integrated areas for the waveform above and below zero being equal. An ion spectrum (sometimes called an ionogram) is obtained by superimposing the asymmetric potential on top of a DC potential and scanning the DC potential. As the DC potential is scanned, ions with different mobilities sequentially pass through the device. Buryakov, et al. showed that amines in a gas mixture can be selectively detected within 10 seconds. They further stated that because of its small size, the parallel plate ion separator can be incorporated into a portable gas analyzer.

The ion separator of FIG. 3, however, has several disadvantages. The linear velocity of the drift gas must be kept constant across the diameter of the tube and also, preferably, along its length. Diffusers are required to establish laminar flow conditions. In addition, the device has a slow response because the velocity of the ions along the longitudinal direction of the drift tube is controlled by the relatively slow moving drift gas.

In U.S. Pat. No. 5,420,424 which issued on May 30, 1995, B. L. Carnahan and A. S. Tarassov disclosed a modified version of the parallel plate ion separator which they called a "transverse field ion mobility spectrometer" (later concatenated to "field ion spectrometer (FIS)") This device is shown in FIG. 4 which is a cross-sectional view of cylindrical geometry. The cylindrical capacitor provides a more uniform field and a greater cross-sectional area for transmission of ions. Instead of using the rectangular waveform of Buryakov, et al., they used an oscillating potential is superimposed upon its second harmonic to generate the asymmetric field; i.e., $V(t)=V_0+V_1[(1-\beta)\cos\omega t+\beta\cos 2\omega t]$, where $V_0$ and $V_1$ are constants and $0.1<\beta<0.7$. The field ion spectrometer has been used to collect spectra on various organo phosphorus and aromatic compounds with a total analysis time of 0.1 to 1.3 seconds. However, the device continues to suffer from the deficiencies noted above for the parallel plate ion separator of FIG. 3.

Despite the fact that they work only under vacuum conditions, certain mass spectrometers Be are related to the devices of FIGS. 1–4. An important mass spectrometer for this purpose is the quadrupole mass filter first disclosed by W. Paul, et al. in U.S. Pat. Nos. 2,939,952 and 2,950,389 which issued on Jun. 7, 1960 and Aug. 30, 1960, respectively. Such a mass filter is illustrated in FIG. 5. The vacuum allows the focusing lenses to accelerate the ions and direct them onto the entrance aperture of four quadrupole rods. Since the function of the quadrupole rods is to separate ions, they are sometimes collectively referred to as a quadrupole ion filter. Again due to the vacuum, the ions maintain their linear velocity as they pass through the quadrupole filter; and as they interact with an oscillating electromagnetic field applied across the rods, they oscillate perpendicular to their original direction of motion. The oscillating field is created by a symmetric RF and DC potential applied across neighboring rods. The magnitude of the ion oscillation is dependent on the mass-to-charge ratio of the ions; and because the oscillations are so great, most of the ions hit the quadrupole rods. Certain of the ions, however, do not hit the rods and survive until they reach the opposite end of the filter. A detector, or electron multiplier, registers the arrival of the surviving ions.

The principle of operation for the quadrupole mass filter relies upon the electric field applying a restoring force to the ion so that it oscillates about some preferred position within the rods. To effectively perform this function, the electric field must satisfy certain spatial distribution requirements. In particular, the electric field must be quadrupolar. Such a field is created by carefully sculpting the internal surfaces of the quadrupole rods. Theoretically, the internal surfaces should define complementary hyperbolas. However, due to difficulties in machining hyperbolas, the hyperbolic rods are often replaced with round rods, (as shown in FIG. 5) that are carefully placed relative to each other to create the desired hyperbolic field.

An ion separator related to the quadrupole mass filter is the monopole mass filter described by U. von Zahn in a paper published in the *Review of Scientific Instruments*, volume 34 (1963), pp. 1–4. Such a filter is shown in FIG. 6. The monopole mass filter is a rod and an angle electrode located relative to each other so that a quarter-section of the quadrupole mass filter is approximated. Ions are separated by applying a combination of RF and DC potentials across the two electrodes. Because the angle electrode occupies the path that the ions would normally travel in a quadrupole mass filter, the ions are injected with a transverse, as well as a longitudinal, velocity component into the monopole mass filter. After injection, the ions describe an arc; first moving toward the rod, and then away from the rod and toward the angle electrode. Like the quadrupole mass filter, the combination of the RF and DC potentials determines which ions pass through the electrode structure for detection by an electron multiplier.

In addition to the quadrupole mass filter, W. Paul and H. Steinwedel al so disclosed a three-dimensional analogue of the quadrupole mass filter in U.S. Pat. No. 2,939,952. This variation eventually became know as the "ion trap mass spectrometer (ITMS)" further disclosed by G. C. Stafford, P. E. Kelley and D. R. Stephens in U.S. Pat. No. 4,540,884, dated Sep. 10, 1985, and shown in FIG. 7. Being a cylindrical analogue of the linear quadrupole filter, the electrode structure for the ITMS consists of a ring-electrode sandwiched between two end-caps with the internal surfaces defining revolutions of complementary hyperbolas. Although other shapes for the electrode structures have been studied, more attention has been given to fabricating ideal electrode shapes (albeit with known distortions) for the ITMS than for the linear quadrupole.

When a symmetric RF and DC (optional) potential is applied across the ring and end-cap electrodes of the ITMS, a trapping field develops within its volume. The trapping field is characterized by a potential well (more specifically, a rotating saddle point) that causes the ions to migrate towards and oscillate around the center of the trap. This trapping field is considerably different from the trapping field described earlier for the field free region of the ion trap mobility spectrometer of FIG. 2. Unlike the ion trap mobility spectrometer, the restoring force invoked by the rotating saddle point causes the ions to be trapped for longer periods of time near the center of the trap. In fact, the times are so long that the ITMS is sometimes referred to as an "ion storage trap", or "ion store" for short. On the other hand, the ions can be ejected at will by changing the combination of the RF and DC potentials applied to the electrodes. This combination of storing and then releasing ions allows ion concentrations (see U.S. Pat. No. 4,650,999, dated Mar. 17, 1987 for handling space charge effects) to be enriched before they are delivered to a detector. It also allows the ITMS to work as a mass spectrometer.

Since the original ion trap inventions, several investigators have disclosed that the trapping field does not have to be quadrupolar. For example, J. Franzen, et al. in U.S. Pat. Nos. 4,882,484; 4,975,577; 5,028,777; 5,170,054; 5,283,436; 5,331,157; 5,386,113 and 5,468,958 state that multipolar fields can be added to the quadrupolar field to create nonlinear resonances that improve mass resolution, scan speed and ion storage stability. In chapter 3 of a book entitled "Practical Aspects of Ion Trap Mass Spectrometry: Volume I" (CRC Press: Boca Raton, Fla., 1995), it is disclosed that the nonlinear resonances can be unintentionally introduced by imperfect machining of the electrodes, or intentionally introduced to improve the performance of the trap.

Examples of electrode structures that can be used to generate multipolar fields are shown in FIGS. 8A–8C. FIG. 8A is the conventional quadrupole structure, while FIGS. 8B and 8C are the hexapole and octapole structures, respectively. The analytical expressions for the electric field and potential created by each of the structures are also shown in FIG. 8. "z" represents the vertical longitudinal dimension and "r" represents the horizontal radial dimension in each case. $E_r$ and $E_z$ represent the electric field in the r and z directions respectively, and $\phi$ represents the potential. To create a nonlinear resonance, a weighted sum of two or more of these fields is necessary.

Other electrode structures that have been investigated for vacuum-operated ion trap mass spectrometers are shown in FIG. 9 along with the equipotential lines they generate. Each trap is a cross-sectional view of cylindrical geometry where the electrodes are indicated by cross-hatched areas. FIG. 9A is the conventional quadrupole structure and FIGS. 9B and 9C are two planar analogues. Brewer, DeVoe and Kallenbach have theoretically analyzed the planar traps in a paper published in the journal entitled *Physical Review A*, volume 46 (1992), pp. R6781–6784. In each case, the electrode(s) corresponding to the ring-electrode is/are labeled as 1, and the electrodes corresponding to the end-caps as 2. It is evident that the equipotential line profile is largely quadrupolar in each case. It is also evident that the planar analogues, have other multipolar contributions.

To date, none of the mass spectrometer devices of FIGS. 5–9 have been successfully used to separate ions at pressures greater than about $10^{-2}$ mm Hg. Any attempt to do so results in a loss of signal. The reason for the loss in signal is that the ions collide with, and are scattered by, the neutral gas molecules contained in the analyzer. The collision and scattering events prevent the ions from reaching the ion collector.

SUMMARY OF THE INVENTION

An apparatus and method is described for analyzing a sample matrix by ionizing its constituent components and separating the ions in an ion mobility storage trait (IMST) with the aide of asymmetric AC and variable DC potentials that are applied across the electrode structure defining the trap volume. In response to the asymmetric AC and DC potentials, the ions are gathered and temporarily stored in the trap volume as they oscillate about preferred equilibrium position(s). The ions are then scanned out of the trap by varying one or more parameters (e.g., magnitudes, phases, etc.) of the AC or DC potentials, and/or their ratios, between predetermined limits. Using this approach, ions with a specific mobility, or a range of mobilities, can be ejected from the trap. The ions exiting the trap are detected by an ion detector (e.g., a Faraday plate) and are identified by the scanning parameters required to expel them from the trap. The device operates in any gas with a pressure greater than $10^{-2}$ mm Hg (including greater than atmospheric pressure).

Additionally if a scan function is not desirable, all the ions can be expelled from the trap by temporarily applying an accelerating potential across the electrode structure of the trap.

Lastly, further embodiments are directed to an ion storage trap used in combination with a variety of ionizers and ion analyzers.

BRIEF DESCRIPTION OF THE DRAWINGS

FIGS. 12A to 12D illustrate movement of an ion within the chamber of FIG. 11 using two pressure and two electric field conditions.

FIGS. 36A, 36B, and 36C show an embodiment where a dipolar trap is integrated with a photoionization source, a discharge ionization source and a $Ni^{63}$ radioactive ionization source, respectively.

DETAILED DESCRIPTION OF THE PREFERRED EMBODIMENTS

Figure 10A:
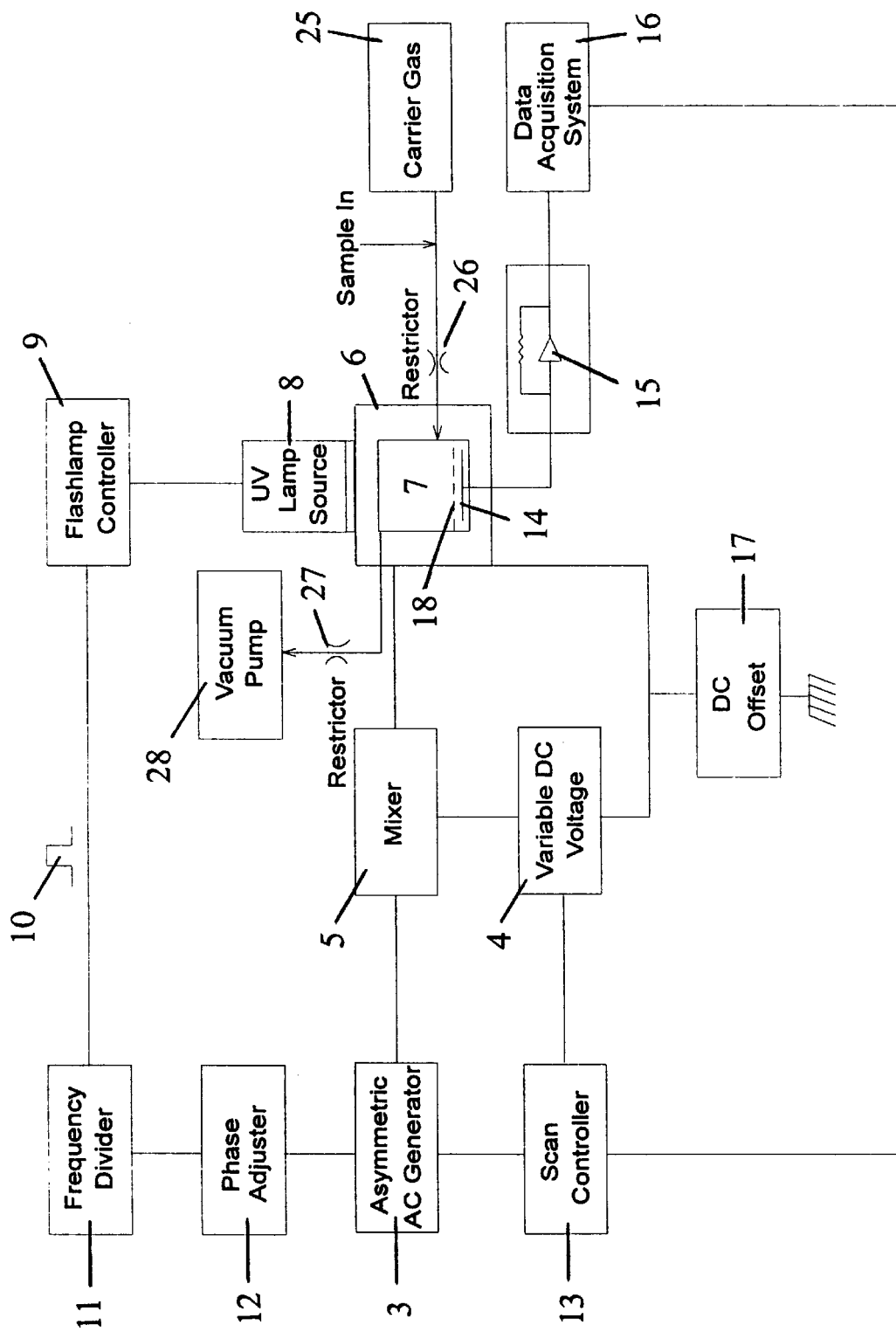
FIGS. 10A and 10B are examples for the ion mobility storage trap system of the present invention.

FIG. 10A is a simplified schematic for an ion mobility storage trap system according to one example of the invention. Element 6 is a general representation of an ion mobility storage trap (also referred to hereinafter as an IMST) that may have mechanical features very similar to the ion trap of mass spectrometry (ITMS). The details of several examples of the ion mobility storage trap will be described in more detail later. AC voltage generator 3 generates an oscillating asymmetric potential and DC power supply 4 generates a variable DC potential. The AC asymmetric potential is superimposed on the DC potential by mixer 5 and is applied across electrodes (not shown) of the ion mobility storage trap 6. Mixer 5 may be an autotransformer or a fast high voltage solid state switch (in combination with a high voltage power supply) similar to that manufactured by Behlke, Frankfurt, Germany. The functions of the AC voltage generator 3 and the mixer 5 can also be combined into a high voltage pulse generator similar to that manufactured by Directed Energy, Inc., Fort Collins, Colo.

A sample is introduced into volume 7 of the trap 6 by flowing a carrier gas, provided by a carrier gas source 25, through a hole in one of the electrodes, or through a space between the electrodes. Restrictor 26 and 27 regulate the flow of carrier gas and sample into and out of volume 7. A vacuum pump 28 may also be connected to trap 6 and in fluid communication with trap volume 7 (not necessary for high pressure operation). Restrictors 26 and 27, in combination with vacuum pump 28, operate to regulate the pressure inside the trap volume, 7.

Ions are formed from the sample using an ultra-violet (UV) flashlamp 8 that is pulsed using a frequency derived from the asymmetric AC generator 3. Alternatively, the ions may be generated outside the trap volume 7 by other known means. Photoionization, however, avoids issues related to injecting ions into trap volume 7 under high pressure conditions. A particularly suited flashlamp for this purpose is a krypton flashlamp equipped with a magnesium fluoride window as supplied by EG&G Electro-Optics in Salem, Mass. G. E. Spangler, J. E. Roehl, G. B. Patel and A. Dorman have described the use of such a flashlamp as an ionization source for IMS in U.S. Pat. No. 5,338,931 which issued on Aug. 16, 1994. Flashlamp 8 can either directly photoionize a sample introduced into trap volume 7, or indirectly ionize the sample when a dopant (e.g., acetone or benzene) is added to the carrier gas. Other flashlamps are also available with different energy characteristics.

A grid (not shown) allows the flashlamp to be inserted into the trap without affecting the field distribution within volume 7.

Flashlamp controller 9 is an energy storage device that matches the low voltage bias circuitry with the high voltage requirements of flashlamp 8. Between flashes, a capacitor within the flashlamp controller 9 charges, and then discharges through the lamp whenever pulse 10 is applied to flashlamp controller 9.

The phase adjuster 12 and frequency divider 11 provide a means whereby the pulse is synchronized with the ion motion in trap volume 7. Specifically, it is desirable that flashlamp 8 discharge (or flash) when the phase of the asymmetric potential is such that the newly formed ions are propelled away from the electrodes and into the main volume 7 of the trap. If the oscillatory motion of the ions is such to allow them to hit the electrodes, the ions are neutralized and are lost for subsequent analysis.

Once the ions are trapped, they experience a variety of forces as they migrate through the gas contained in volume 7. Some of the forces originate from collisions between the ions and the neutral gas molecules contained in the trap, but others include interaction of the ions with the electric field. As explained in more detail below, the function of the asymmetric AC and DC potentials across the electrodes is to create an oscillating electric field that causes the ions to migrate towards an equilibrium position within the trap. This tendency for migration is related to the field dependence of the mobility for the ions. Because different ions have different mobility characteristics, a mixture of different ions eventually occupy different locations within the trap and are separated according to type.

The location for the equilibrium positions is changed by changing the relative amplitudes for the asymmetric AC and DC potentials. Thus, the ions can be moved around in trap volume 7 by scanning the potentials with scan controller 13. An appropriate scan function might be to continuously increase the DC potential so that the ions vertically exit the trap towards ion collector 14. Ion collector 14 may be encapsulated in a Faraday cage that is AC coupled to ground. This, together with a high gain electrometer 15, filters out ripples created by the asymmetric AC potential that might otherwise produce noise in the ion signal.

The ion current induced in ion collector 14 is amplifed by electrometer 15 for processing by the data acquisition system 16. The data acquisition system 16 first determines the combination of AC and DC potentials that caused the ions to exit the trap, and then from that information determines the type of ion. A DC offset 17 is provided so that ion collector 14 can be maintained at a virtual ground equal to system ground. The DC offset establishes the potential for aperture grid 18 that serves as an end-cap electrode for trap 6.

Figure 10B:
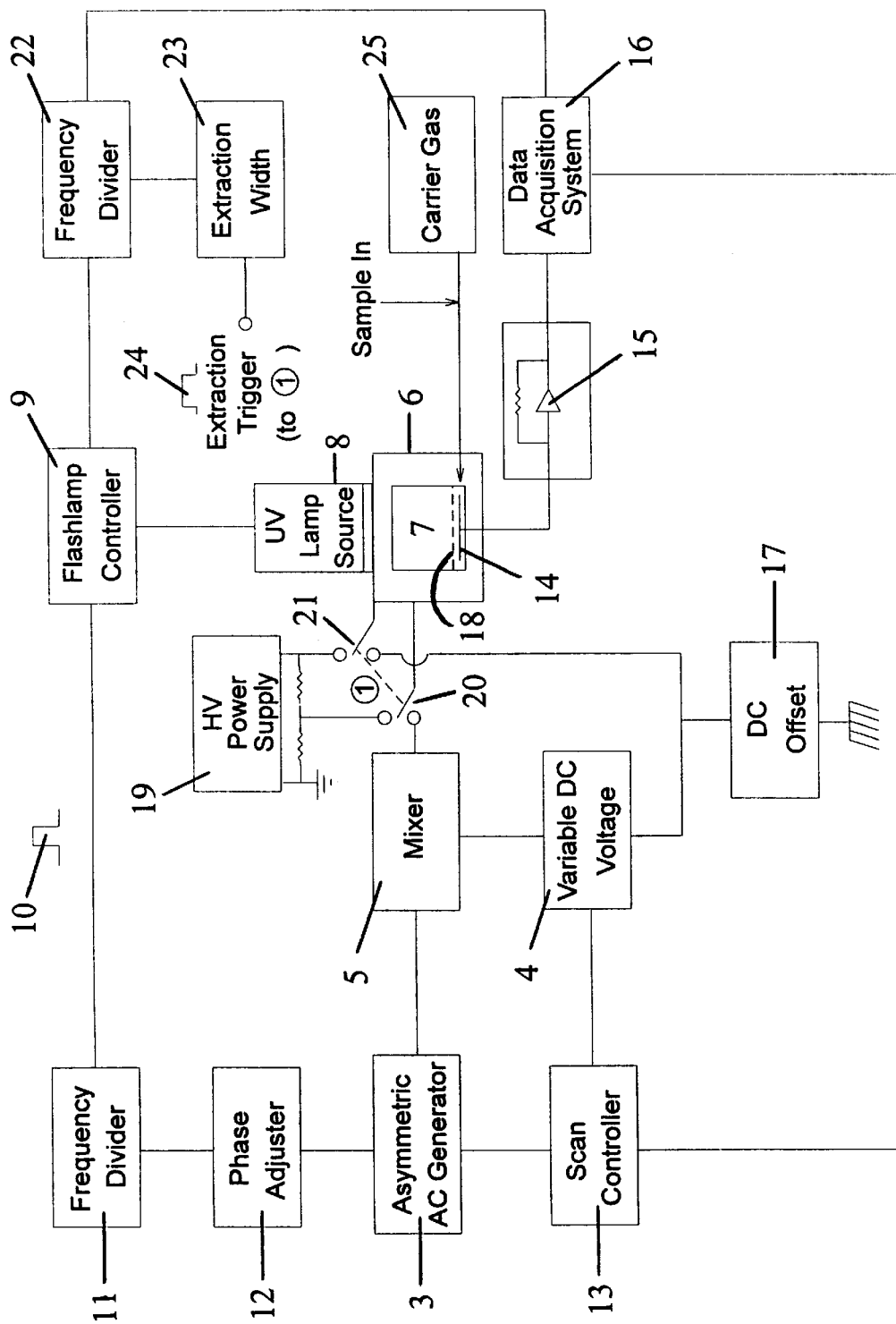

FIG. 10B illustrates another example of the ion mobility storage trap. Elements labeled with the same numerals have the same function as those illustrated in FIG. 10A. Because their operation is the same, their description is omitted here. Additionally included in FIG. 10B is a high voltage power supply 19, a pair of electronic (including, but not limited to, relay switches) switches 20 and 21 selectively connecting the high voltage power supply to electrodes within trap 6, a frequency divider 22 and an extraction width adjuster 23 for controlling the operation of switches 20 and 21.

Instead of removing the ions from volume 7 using scan controller 13, the high voltage power supply 19 and switches 20 and 21 remove the ions by applying an accelerating potential between the end-cap electrodes as described by Q. Ji, M. R. Davenport, C. G. Enke and J. F. Holland in the *Journal of the American Society of Mass Spectrometry* volume 7 (1996), pp. 1009–1017. The switches are driven by an extraction trigger pulse 24 that is synchronized with the data acquisition system 16 through frequency divider 22. The effect of the high voltage power supply 19 is to propel the ions towards ion collector 14. Buttrill, Jr., et al. in U.S. Pat. No. 5,569,917 which issued on Oct. 29, 1996; M. H. Studier in a paper published in the *Review of Scientific Instruments*, volume 34 (1963), pp. 1336–1370; B. F. Bonner, et al. in a paper published in the *International Journal of Mass Spectrometry and Ion Physics*, volume 10 (1972/1973), pp. 197–203; R. E. Mather, et al., in a paper published in the *International Journal of Mass Spectrometry and Ion Physics*, volume 28 (1978), pp. 347–374; and J. E. Fulford, et al. in a paper published in the *Journal of Vacuum Science and Technology*, volume 17 (1980), pp. 829–835 discuss and critically evaluate other approaches to electronically pulsing/accelerating ions out of an ion trap mass spectrometer. These, and other techniques are all applicable to this invention with equal facility.

Ion Oscillations in Electromagnetic Fields

Before describing in detail the motion of the ions in trap volume 7, it is instructive to first describe the dependence of an ion's mobility on the strength of the electric field in which it exists.

Figure 11:
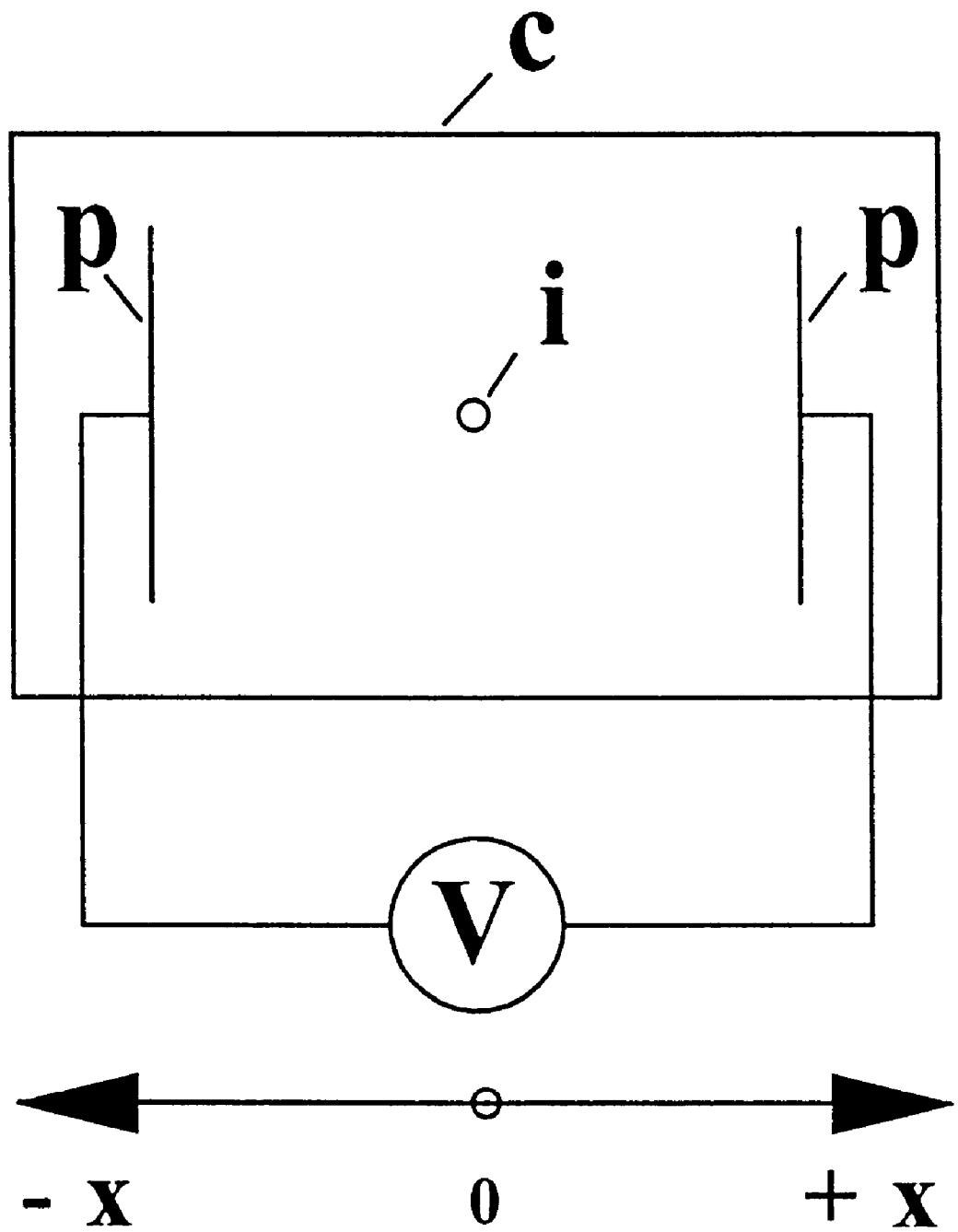
FIG. 11 illustrates an ion positioned between two parallel plates in a chamber.

FIG. 11 shows ion i positioned between two parallel plates p within chamber c. A voltage source V applies a potential across plates p to generate an electric field between them. The axis connecting the two plates is the x-axis with the origin located midway between the plates. The electric field generated between plates p will be assumed uniform (so that the electric field lines are parallel and evenly spaced).

FIGS. 12A to 12D illustrate the motion of ion i using four different operating conditions in chamber c. FIGS. 12A and 12B illustrate the movement of the ion i when a vacuum condition exists in chamber c and a potential having a sinusoidal waveform is applied across parallel plates p. Newton's Law states that ion i experiences a force given by $$F = ma = qE \quad (1)$$

where m is the mass of the ion, a is its acceleration, q is its charge, and E is the electric field strength. The location of the ion in volume c is determined by the second integral of the acceleration along with some initial conditions. If it is assumed that the ion is introduced into the chamber at x=0 with an initial velocity of v=0, and the initial phase of the sinusoidal waveform when the ion was introduced into the trap is 90° (i.e., sin (ωt) having a value of one), FIG. 12A shows that the subsequent motion for the ion will be sinusoidal where the broken curve represents the ion's velocity and the solid curve the ion's position. When the right electrode of FIG. 11 is positively charged, a positive ion will initially move in the negative x-direction with an increasing velocity. As the sinusoidal potential changes polarity, the ion decelerates and begins to move in the positive x-direction (i.e., change direction). Because the electric field applied between the plates exerts an equal and opposite force on the ion for each polarity of the potential (i.e., for each half cycle of the sinusoidal waveform), the displacement of the ion in each direction is the same. Thus, the ion oscillates about a fixed location within volume c. In FIG. 12A, the ion is shown oscillating about x=0.

FIG. 12B shows the motion of the ion of 12A when it is introduced into chamber c with the initial phase of the sinusoidal potential is equal to zero. The ion immediately experiences a negative acceleration and drifts in the negative x-direction ad infinitum. The reason for the continued drift is that any momentum added to the ion by the electric field can not be completely removed. Thus when an ion has an initial velocity, it has a tendency to drift in the direction dictated by that initial velocity. The net effect of FIGS. 12A and 12B is that if a large number of ions are randomly introduced into chamber c at x=0, the ion cloud expands as some of the ions oscillate around x=0, and others drift off in the positive and/or negative x-directions respectively.

FIG. 12C illustrates the movement of the ion i when the chamber c contains a gas with a pressure of $10^{-2}$ mm Hg or greater. A potential having a sinusoidal waveform is again applied to parallel plates p. The motion of the ions is dependent on the ion's mobility. Specifically, collisions between the ion and molecules of the gas impede the motion of the ion and, unlike the vacuum condition of FIGS. 12A and 12B, the ion drifts with a drift velocity proportional to the strength of the electric field (to which the ion is subjected). The drift velocity $V_d$ is given by a mobility coefficient K times the electric field E:

$$v_d = \pm K \cdot E \quad (2)$$

The mobility coefficient K is constant for low electric fields, but increases as the electric field strength increases. An approximate expression for the dependence of K on the electric field is:

$$K(E) = K_0 + K_2 \cdot E^2 + K_4 \cdot E^4 + \ldots \quad (3)$$

where the $K_i$'s are coefficients dependent on the ion species under investigation. In a weak electric field, the solid curve in FIG. 12C illustrates that ion i oscillates about a fixed position within chamber c. The deviations are generally sinusoidal; but since the position is related to the integral of the driving potential (or the drift velocity as represented by the broken curve in FIG. 12C), the maximum deviations in position are 90 degrees out of phase with the electric field.

In a strong electric field, FIG. 12D shows that the dependence of the ion mobility on electric field causes the drift velocity to peak at the extremes of the oscillating potential. That is, the mobility, and hence the velocity, of the ion increases and maximizes at the extremes of the driving potential. In order for this maximization to occur, the ion must gain energy from the electric field in excess of the thermal energy that it otherwise has in a low electric field. Because of the energy gain, the ion of FIG. 12D migrates with a non-sinusoidal trajectory in volume c. The ion still oscillates about a fixed position within chamber c, however, because the waveform of the potential is symmetrical during the positive and negative phases of the applied potential. The ion experiences equivalent accelerations and decelerations.

Figure 13:
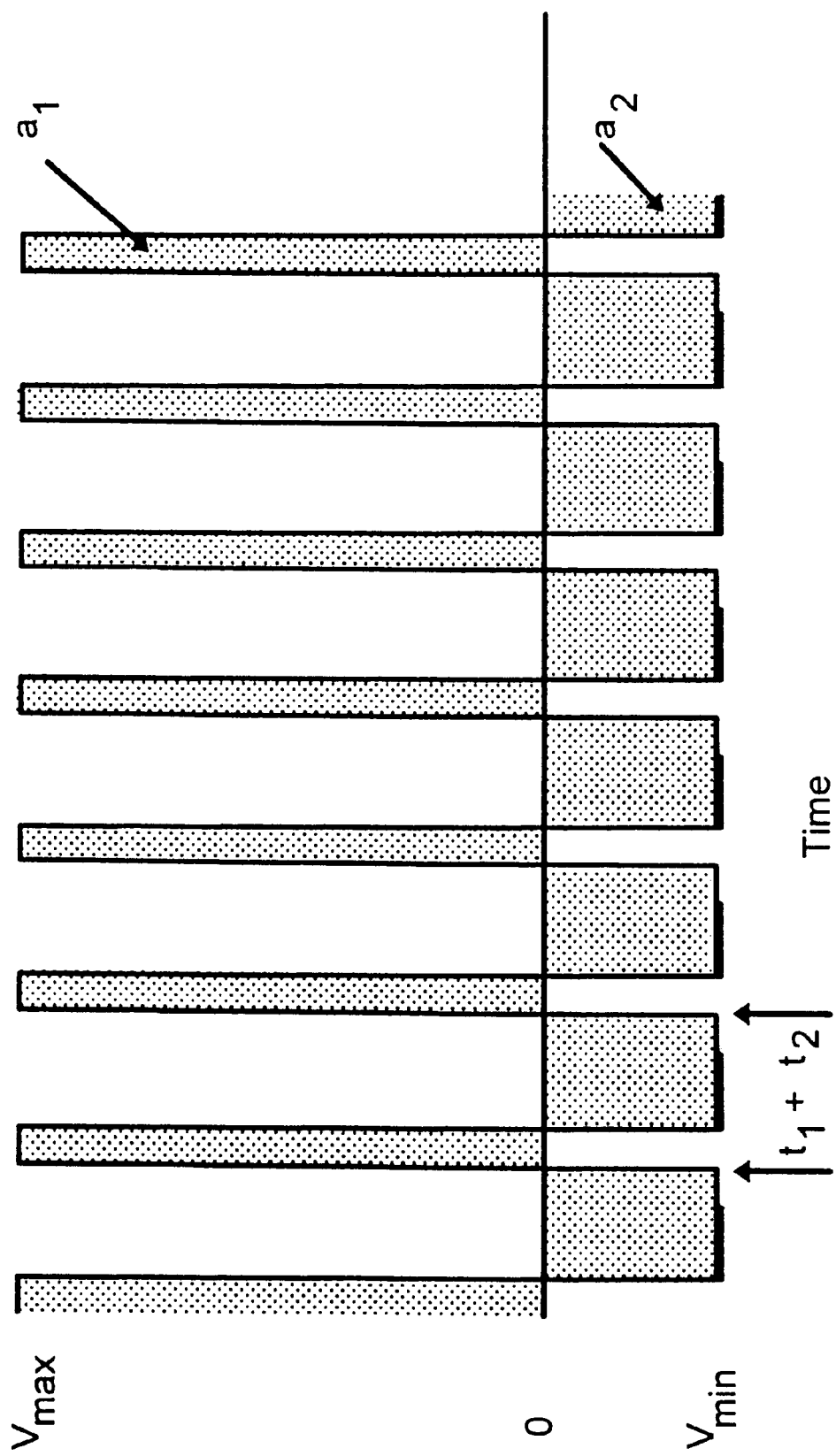
FIG. 13 illustrates one example of a voltage having an asymmetric waveform.

The situation changes when an asymmetric potential is applied across the plates p of FIG. 11. FIG. 13 illustrates an appropriate waveform. The waveform has a period of $t_1 + t_2$, is constant and positive over sub-period $t_1$, and is constant and negative over sub-period $t_2$. The waveform is also shown to have an absolute value in the positive going direction ($V_{max}$) much greater than in the negative going direction ($V_{min}$), and an area defined by the positive going portion of the waveform (shaded area $a_1$) equaling the area defined by the negative going portion of the waveform (shaded area $a_2$).

Now if chamber c in FIG. 11 is filled with a gas and the waveform of FIG. 13 is applied across its plates p, the ion may or may not oscillate about a fixed position within the device depending upon the absolute values of $V_{max}$ and $V_{min}$ and the ion type. If the absolute values; are below a certain threshold value where the mobility of ion i is independent of the electric field strength (i.e., the mobility is always constant), the ion i will return to its original position after each completed cycle. This will occur regardless of the mobility of the ion. In completing its cycle, ion i will travel with velocities $v_{t1}$ and $v_{t2}$ during time periods $t_1$ and $t_2$, respectively. The total displacement of the ion for each cycle is $t_1 \cdot v_{t1} - t_2 \cdot v_{t2}$, or $t_1 \cdot K_{t1} \cdot E_{t1} - t_2 \cdot K_{t2} \cdot E_{t2}$, where $K_{tx}$ and $E_{tx}$ are the mobility of the ion and the electric field, respectively. Because the areas $a_1$ and $a_2$ of FIG. 13 are equal, $t_1 \cdot E_{t1} = t_2 \cdot E_{t2}$, and the total displacement is zero.

Figure 14:
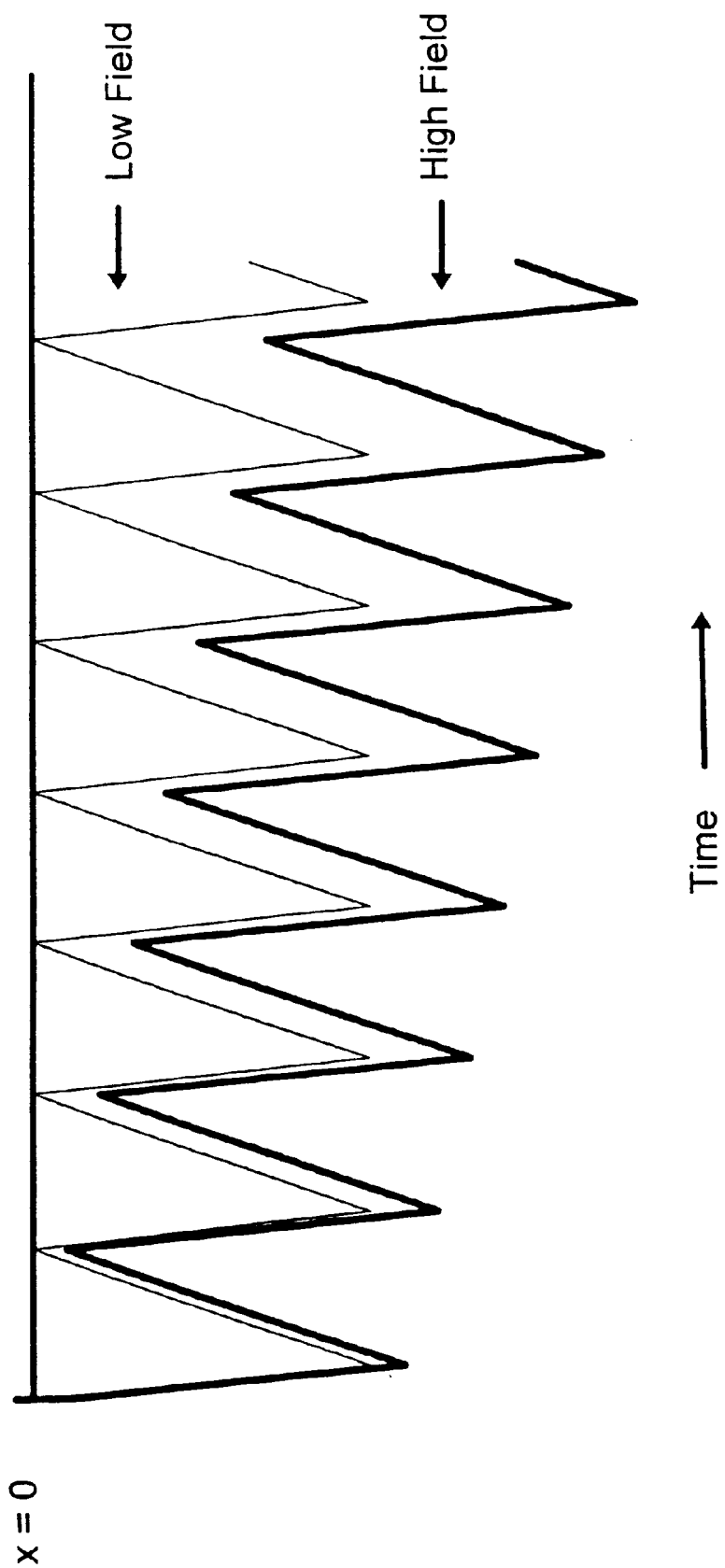
FIG. 14 illustrates movement of an ion within the chamber of FIG. 11 with the voltage of FIG. 13 applied across the plates.

If the absolute value of $V_{max}$, or both $V_{max}$ and $V_{min}$, exceed a certain threshold value, the mobility of the ion becomes dependent on the strength of the electric field. That is, if chamber c of FIG. 11 is again filled with a gas and the waveform of FIG. 13 is applied to its plates p, the mobility of ion i will be different as it travels in one direction versus the other. Because of this difference in mobility (and hence velocity), the ion will experience a displacement as it responds to one complete cycle of the oscillating potential that is given by $t_1 \cdot K_{t1} \cdot E_{t1} - t_2 \cdot K_{t2} \cdot E_{t2} \neq 0$. The net result is that the ion gradually drifts towards one or the other of the plates of FIG. 11. This drift is illustrated in FIG. 14 where the light curve is the ion's motion under low field conditions, and the dark curve is the ion's motion under high field conditions. Since FIG. 14 shows the ion slowly migrating in the negative x-direction, it is moving toward the left plate in FIG. 11.

One Example of an Electrode Configuration for an Ion Mobility Storage Trap

Figure 15:
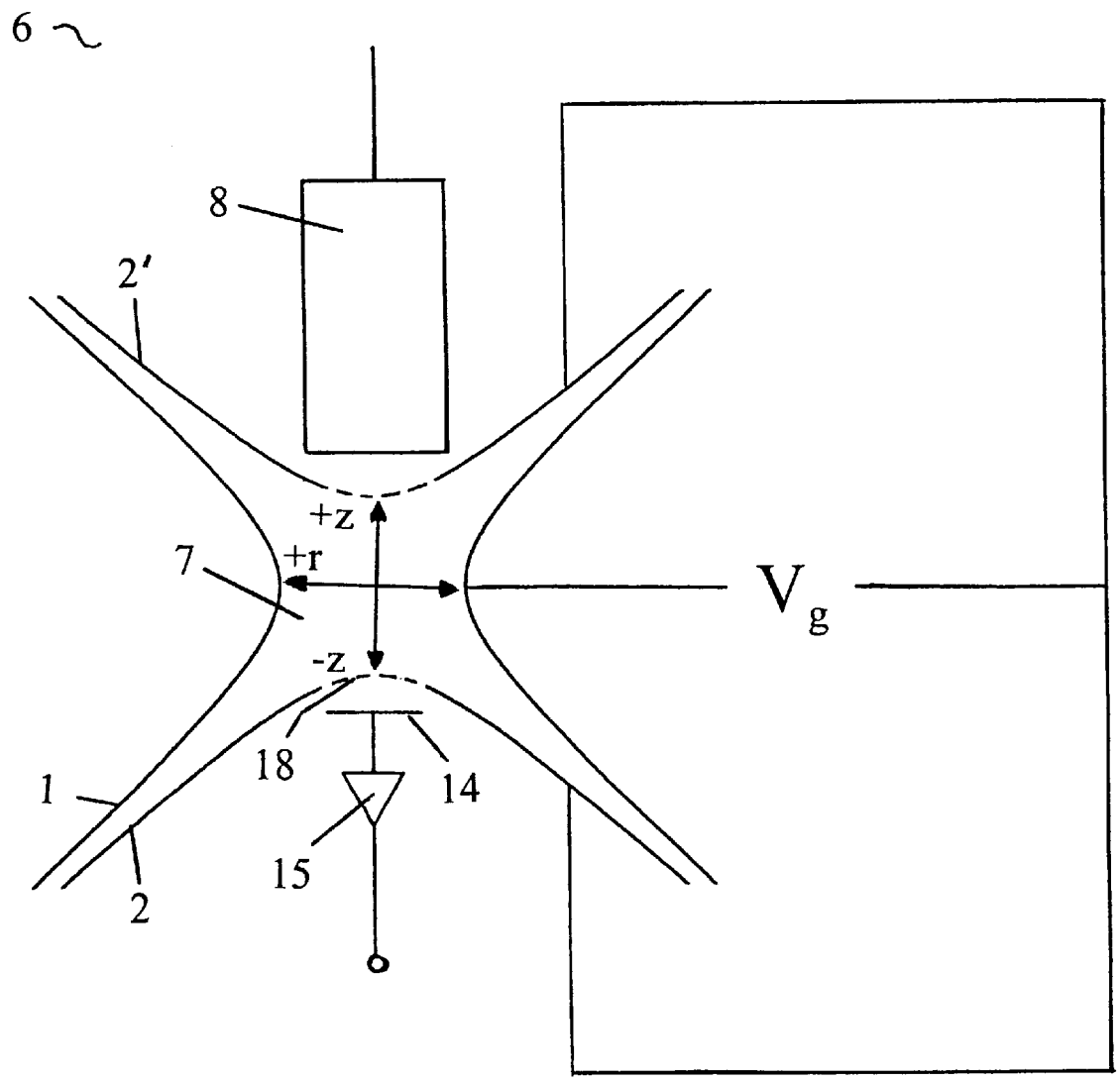
FIG. 15 illustrates one example of a trap structure according to this invention.

FIG. 15 illustrates a cross-section of one example for an ion mobility storage trap 6 according this invention. The ion mobility storage trap 6 includes ring electrode 1 and two end-cap electrodes 2, 2' of cylindrical geometry. The z-coordinate extends vertically along the symmetry axis connecting the two end-caps (positive towards end-cap electrode 2', negative towards end-cap electrode 2), the r-coordinate extends radially from the z-axis towards ring electrode 1, and the origin is located at the center of the trap. The end-cap electrodes 2 and 2' are hyperbolically shaped, the apex of each hyperbola lying on the z-axis. As its name implies, the ring electrode 1 is ring-shaped with its axis of symmetry located along the z-axis. Note that in FIG. 15, the cross-section for the ring electrode appears as two opposing hyperbolas.

The electrodes 1, 2, and 2' define trap volume 7. Aperture grid 18 allows ions to leave the trap volume 7 along the z-axis (in the negative direction, or downward in FIG. 15). Faraday plate 14 acts as an ion collector to collect the ions as they leave the trap. The electric current generated by the ions is amplified by a high-gain amplifier or electrometer 15.

A functional ion mobility storage trap has a potential applied between its ring electrode 1 and end-caps 2 and 2'. Except where special pulsing procedures are used to eject ions, the two end-caps 2 and 2' are connected electrically with the same potential. In FIG. 15, the electronics applying the potential to the electrodes is simplistically represented by voltage generator $V_g$ that may include, for example, one or more of the components in FIG. 10. Those skilled in the art of ion trap spectrometry will recognize that many types of voltage generators can be applied to the trap 6 other than those illustrated in FIG. 10.

The trap volume 7 contains a neutral gas. Since the operation of the trap 6 depends on the collisions of ions with neutral gas molecules, gas pressures greater than $10^{-2}$ mm Hg are desirable within volume 7. For pressures less than atmospheric, a vacuum pump is required to help regulate the pressure. The vacuum pump requirement can be removed by operating the trap under atmospheric pressure conditions, or slightly above.

Figure 16A:
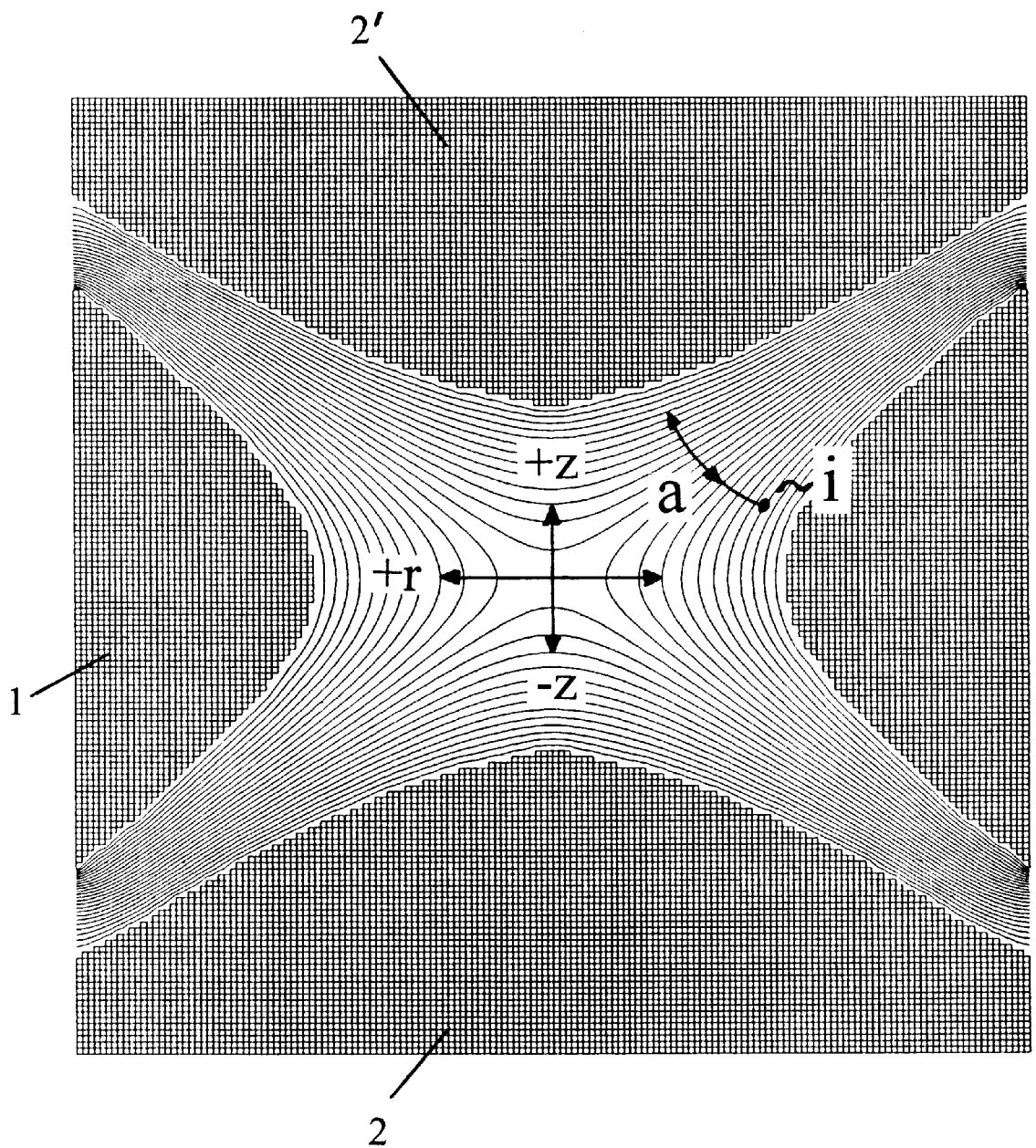
FIGS. 16A and 16B illustrates equipotential lines within the trap structure of FIG. 15.
Figure 16B:
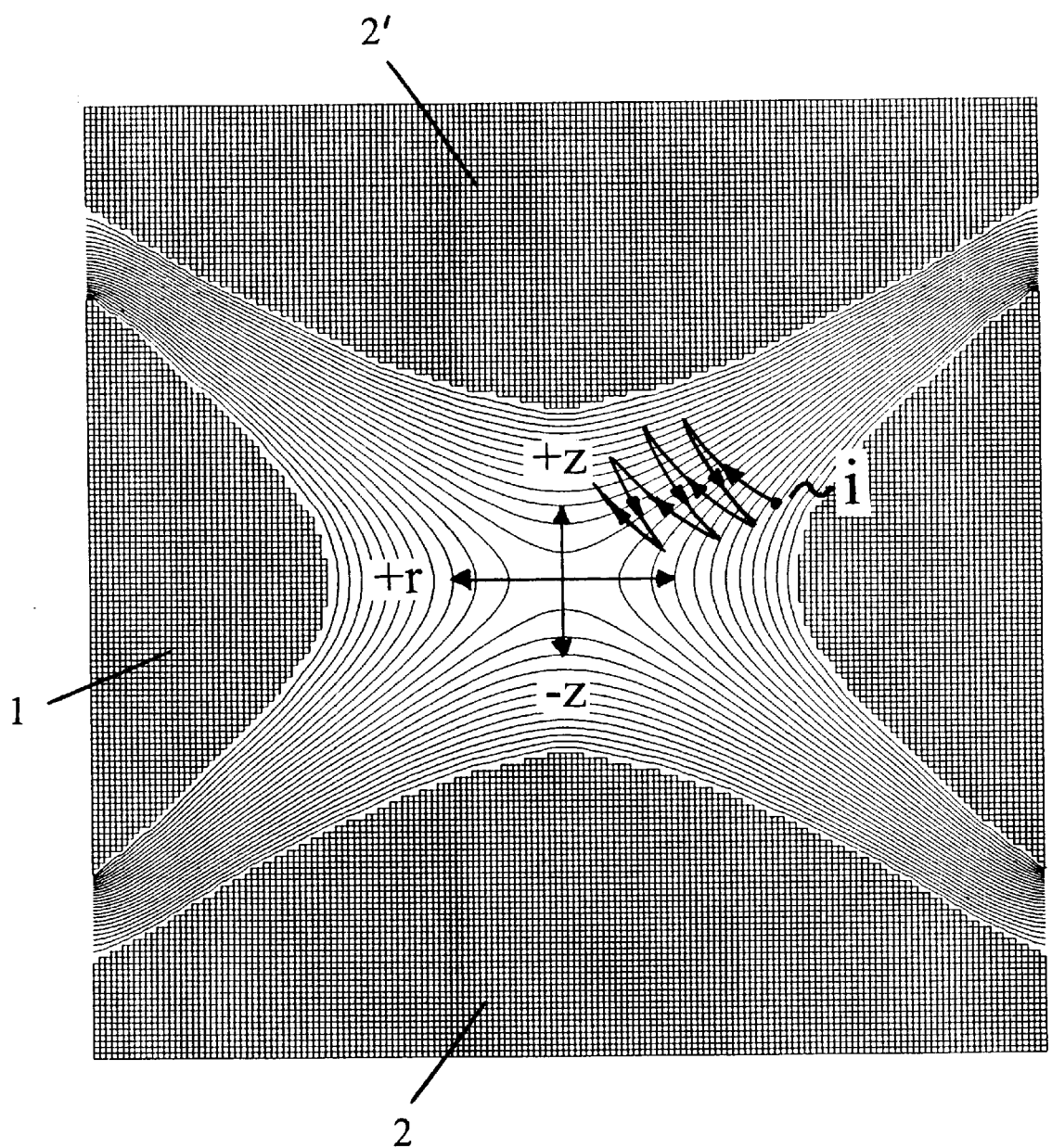

The operation of the trap can be explained with assistance from the SIMION plot of FIG. 16A and FIG. 16B which is a plot of the equipotential lines created by potential $V_g$ within trap volume 7. SIMION is an electrostatic lens analysis and design computer program developed by D. C. McGilvery at LaTrobe University in Australia, and extensively redesigned by D. A. Dahl at Idaho National Engineering Laboratories, Idaho Falls, Id. The cross-hatched areas correspond to electrodes 1, 2, and 2' in FIG. 15.

FIG. 16A illustrates the motion of ion i in a potential of single polarity that is applied across ring electrode 1 and end-cap electrodes 2 and 2' (the end-cap electrodes are at the same potential).

Depending on the charge on the ion and whether the potential is positive or negative, the ion travels from the ring electrode towards the end-caps, or vice versa. In FIG. 16A, ion i is shown traveling from ring electrode 1 towards end-cap electrode 2'. The trajectory that the ion follows is normally perpendicular to the equipotential lines, as indicated by path "a" in FIG. 16A. The ion will continue to follow this trajectory until either it arrives at end-cap electrode 2', or the polarity of the potential is reversed, whichever occurs first. If it arrives at end-cap electrode 2', its charge is lost to the electronic circuitry biasing the electrodes.

If, on the other hand, the polarity of the potential is reversed before ion i arrives at end-cap 2', the ion will change its direction of motion and retrace its path.

Figure 17A:
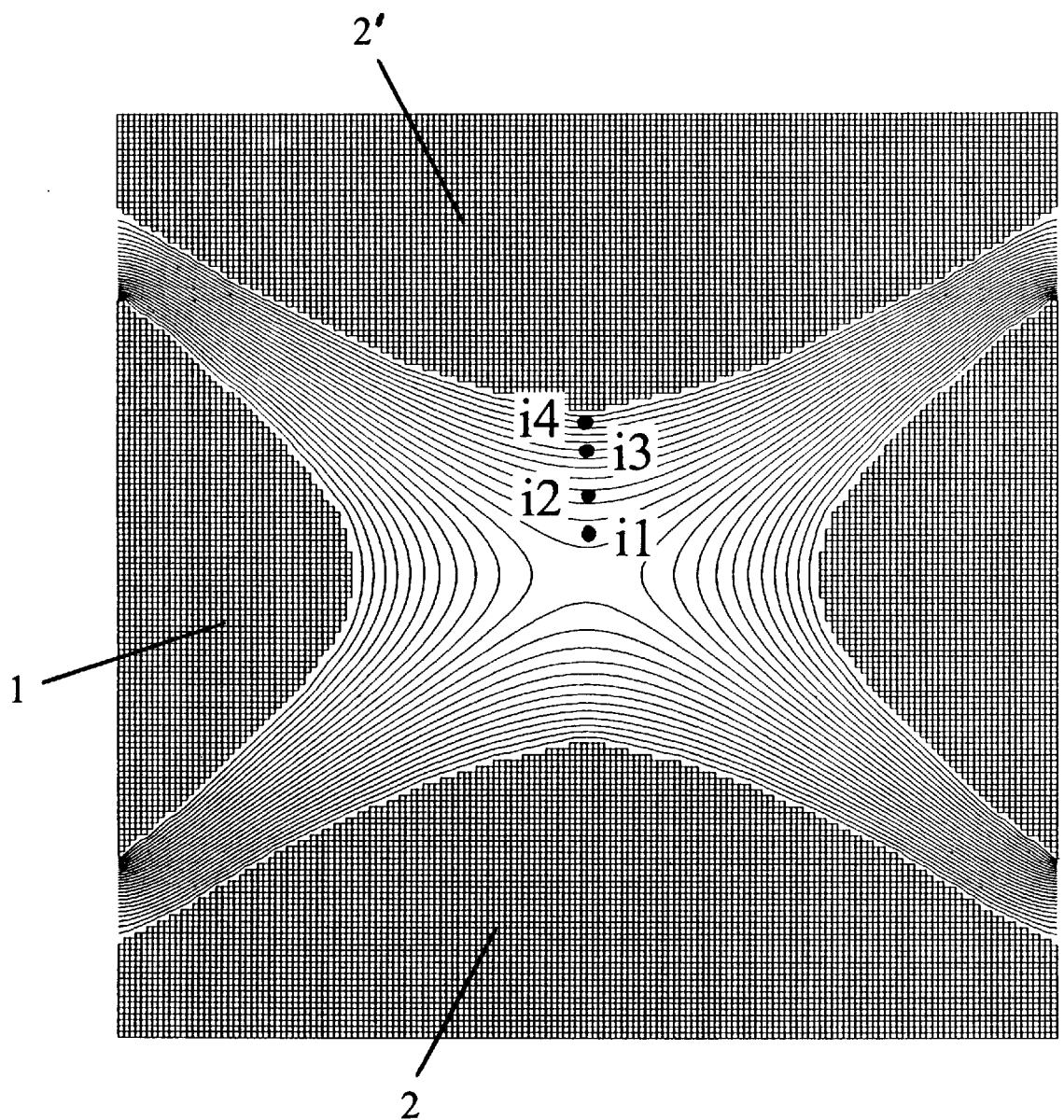
FIGS. 17A and 17B illustrate equilibrium positions of different types of ions.

Now when voltage generator $V_g$ applies an asymmetric potential (as illustrated in FIG. 13) between ring electrode 1 and end-caps 2 and 2' of the trap in FIG. 16A, the motion of the ions is altered. First, the ions have a tendency to migrate towards the center of the trap as illustrated in FIG. 16B. This occurs because during period $t_1$, the ions experience a high electric field that draws them towards the center of the trap. The strength of this electric field is greater than that applied during period $t_2$ that draws the ions away from the center of the trap (or towards end-cap electrodes 2 and 2'). Second, the ions have a tendency to distribute along the z-axis as illustrated in FIG. 17A. This occurs because the strength of the electric field varies within trap volume 7 and the ions seek a location where their displacements during time periods $t_1$ and $t_2$ are equal. More details on this motion will be given later in connection with FIGS. 20 to 34.

Voltage generator $V_g$ also generally superimposes a DC potential on. the asymmetric AC potential (by variable DC voltage generator 4 in FIG. 10, e.g.) of the trap in FIG. 16A and applies the resulting potential across the ring electrode 1 and end-cap electrodes 2 and 2'. In this example, the DC component shifts the waveform illustrated in FIG. 13 downward. Typically, the DC potential is selected to counteract the ion movement created by the asymmetric electric field. The DC component of the potential acts to attract the ions toward end-cap electrodes 2 and 2', the AC potential component, as explained above, acts to repel the ions from end-cap electrodes 2 and 2'. Depending on the mobility of the ions and the AC and DC ratio, the ions will migrate towards an equilibrium position within the trap, and oscillate about that equilibrium position. More specifically, depending on the change of mobility of the ions as the strength of the electric field (here, a function of z), the ions will move toward an associated equilibrium position. Thus, samples may be continuously introduced into the trap and ionized. The ions of the samples will localize along the z-axis, separate according to type and distribute about associated equilibrium positions.

FIG. 17 illustrates how a mixture of ions (i1, i2, i3 and i4) can be separated using an ion mobility storage trap of type shown in FIG. 15. In FIG. 17A, ion group i1 has a greater difference in mobilities during periods $t_1$ and $t_2$; thus the movement of ion group i1 is influenced by the AC component of the electric field at an area where the electric field is relatively weak, close to the center of trap volume 7. In contrast, at ion group i1's equilibrium position, ion group i4 has a lesser difference in mobilities during periods $t_1$ and $t_2$. The DC component of the electric field functions to pull ions of ion group i4 closer to the end-cap electrode 2'. As the ions near end-cap electrode 2', the electric field strengthens and the difference in the mobility of ions of the ion group i4 during periods $t_1$ and $t_2$ grows greater. At ion group i4's equilibrium position, the difference in the mobility of the ions during periods $t_1$, and $t_2$ counteract the DC component of the electric field, and the ions of ion group i4 oscillate about their equilibrium position. The mobility characteristic, of ions i2 and i3 are intermediate to those of i1 and i4.

Figure 17B:
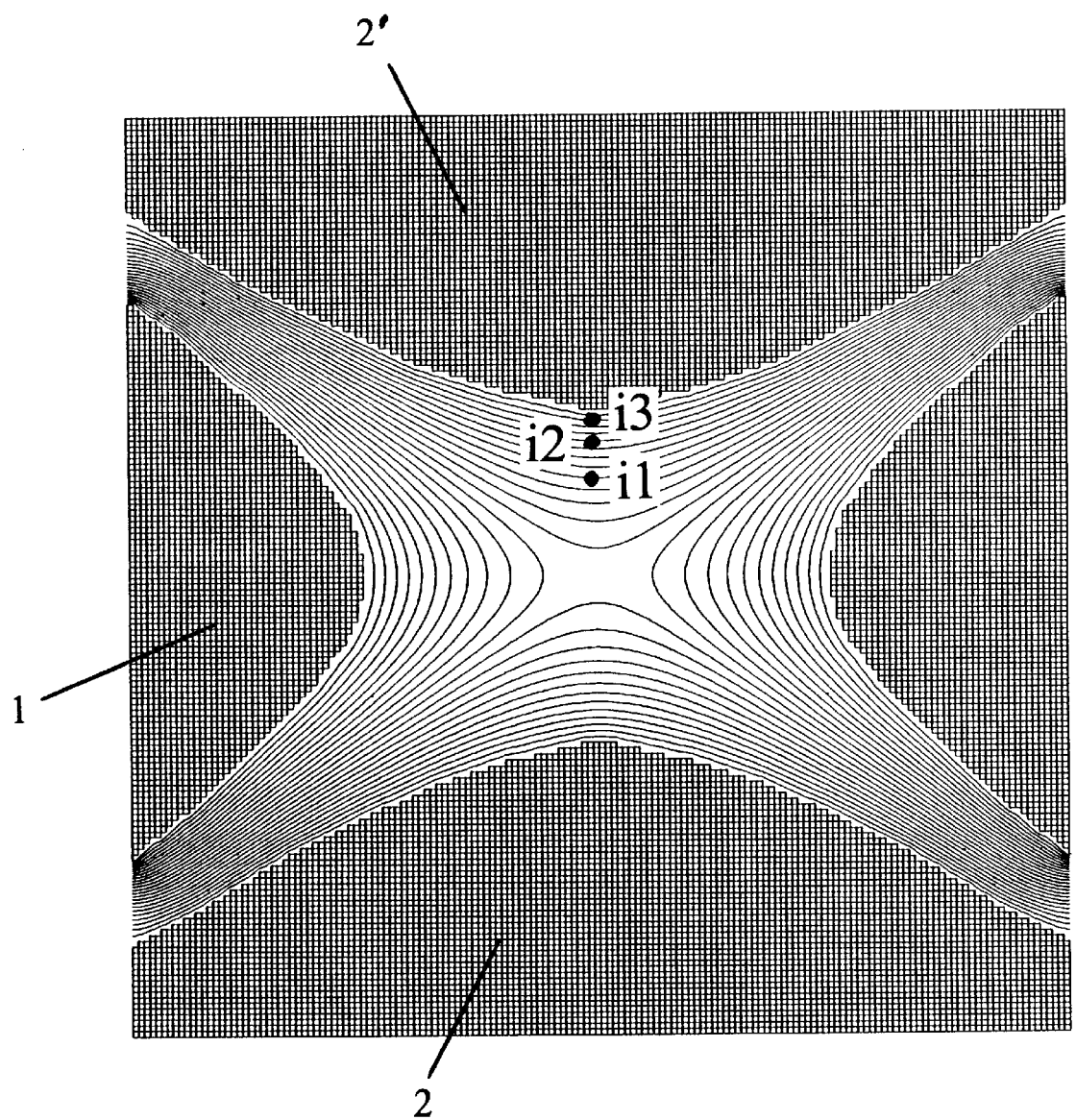

FIG. 17B illustrates the state of ion groups i1, i2, i3 and i4 after the DC component of the electric field is applied. The ion groups have shifted along the z-axis towards the end-cap electrode 2'. Ion group i4 has migrated out of the trap volume 7 through an opening in the end-cap electrode 2' (not shown). The opening may contain an ion collector protected by an aperture grid (14 and 18 in FIGS. 10 and 15, e.g.). By continuing to increase the DC potential, all the ions can be scanned out of trap volume 7. As the ion collector 14 collects the ions leaving trap volume 7, the ion current is amplified by an electrometer circuit 15 for delivery to a data acquisition system 16. In addition to the DC potential, the amplitude or phase relationships within the AC asymmetric potential can be used to scan the ions out of the trap.

This combination of equipment can be used to identify the components of a sample matrix that has been injected and ionized (by ionizer 8 in FIG. 15, e.g.) in trap volume 7 by monitoring the AC and DC potentials required to expel the ions from the trap. Consequently, a sample can be introduced into an ion mobility storage trap, the components ionized into characteristic ions, and the products ions stored along an axis of the trap. The ions are then scanned out of the trap by using a variable DC potential, detected by an electrometer amplifier circuit, and analyzed by a data acquisition system for content of the original sample.

The above description applies to ions of either positive or negative polarity. The only difference in operation of the trap is the polarity of the potentials applied to the trap. Ions of opposite polarity are analyzed by inverting the polarity of both the AC asymmetric and DC potentials applied across electrodes 1, 2, and 2'. Also because of the symmetry of the trap, the ions can be trapped along the r-axis and scanned out of the trap through the ring electrode. This is accomplished by changing the polarity of either the DC or AC asymmetric potential, but not both.

To assist in the explanation, the above description describes first applying a voltage with only an AC component and then with both AC and DC components across the electrodes. However, this is not necessary; a voltage with both the AC and DC components may be applied from the start of operations.

Figure 18:
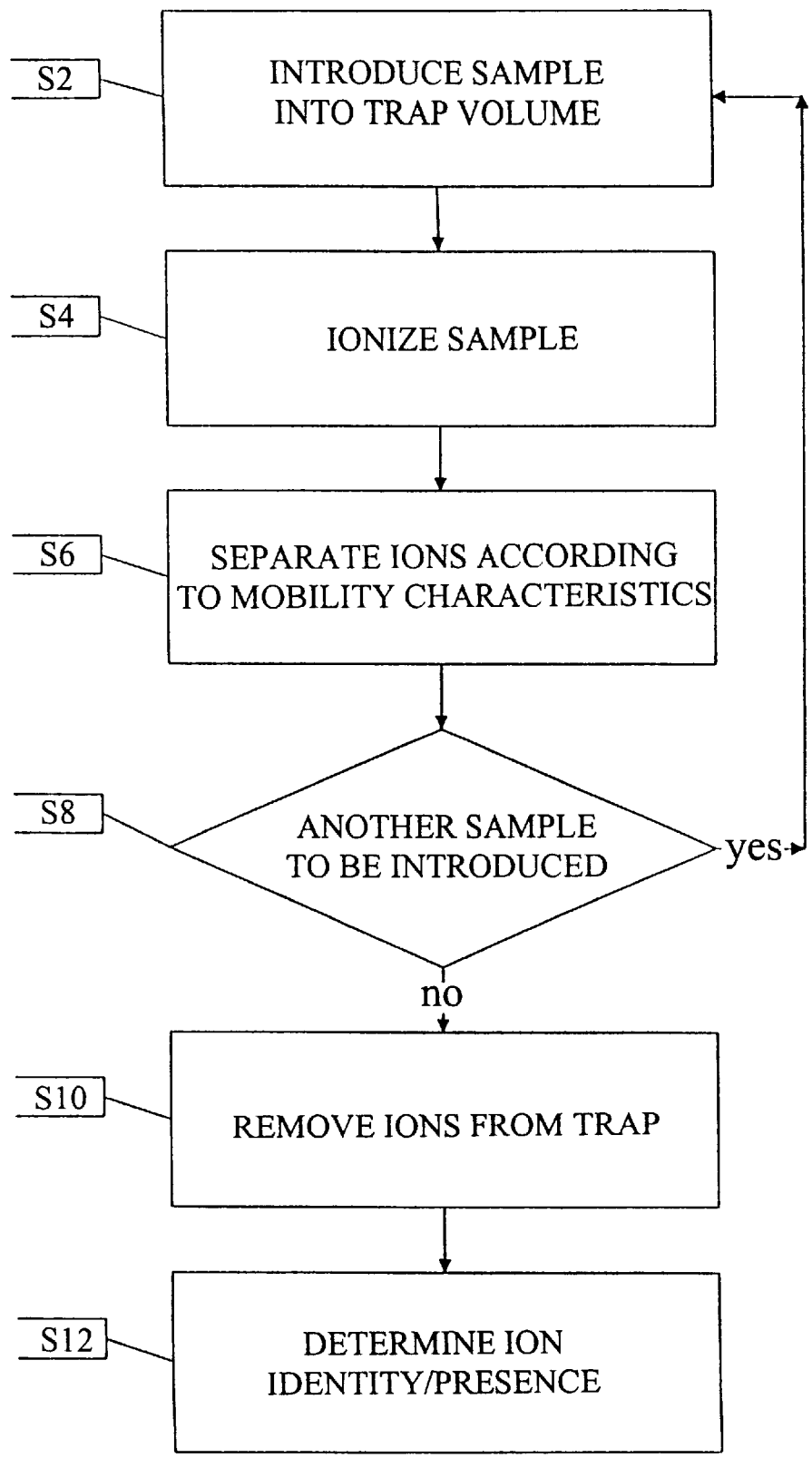
FIG. 18 illustrates a method according to another example of the invention.

FIG. 18 illustrates such a method of operation for the trap. In step S2, a sample is introduced into the trap volume. The sample is ionized in step S4. The ions are separated according to their mobility characteristics in step S6 by applying the appropriate potentials across the electrodes and causing the ions to migrate to their equilibrium positions. A decision is made in step S8 whether another sample should be introduced (or continued to be introduced). If another sample is introduced, the process repeats step S2, S4, and S6. If no further samples are introduced, the process proceeds to step S10. In step S10, the ions are removed from the trap. The ions may be sequentially scanned from the trap by changing one of the DC potential components, the AC potential components, or a combination thereof. In step S12, the identity of the ions removed from the trap are determined and correlated with the sample. Alternatively, in step S12, single ion monitoring can be performed, for example, by reversing the DC potential, scanning the reversed DC potential to eliminate ions with low mobilities, returning the DC potential to normal polarity, and scanning the DC potential to a predetermined value to eject the ions of interest.

Figure 19:
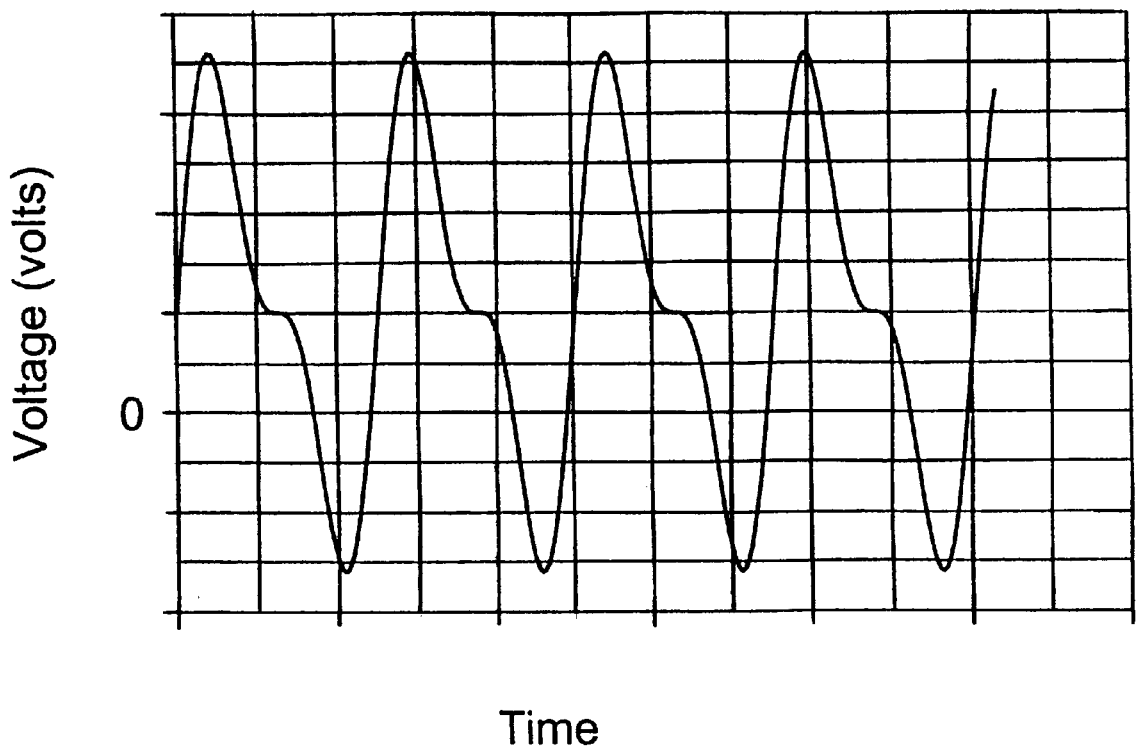
FIG. 19 illustrates another example of a voltage having an asymmetric potential.

As apparent from the above description, other waveforms for the asymmetric potential, other than the one displayed in FIG. 13, can be used to excite ion motion in the ion mobility storage trap. For example, the waveform shown in FIG. 19 is a sinusoidal waveform superimposed on its second harmonic and a DC potential. The purpose of the asymmetric waveform is to induce in the ions a velocity component that varies in a non-compensating manner throughout one complete cycle of the waveform. Thus, the best approach to selecting an asymmetric potential is to intuitively focus on the dynamic changes that occur in the ion's velocity as it migrates through one complete cycle of the waveform and the parameters that prevent it from returning to its original position.

To more fully appreciate the other types of asymmetric potentials that can be used to separate ions using the current invention, it is necessary to develop a more detailed description for ion motion in an ion mobility storage trap. The following provides such a description. As ion i responds to the oscillating electromagnetic field, it experiences a variety of forces. In addition to the forces that originate from interaction of the ion with the electric field, others originate from collisions of the ion with neutral gas molecules. For each collision, Newton's Force law of classical physics applies and the net force acting on the ion and its collision partner satisfies:

$$\Sigma \vec{F} = M \vec{a}_{cm} \tag{5}$$

where $\Sigma \vec{F}$ is the vector sum of the forces acting on the center-of-mass of the ion and its collision partner, M is the total mass of the colliding pair, and $\vec{a}_{cm}$ is the acceleration of the center-of-mass. If $m_1$ is the mass of the collision partner and $m_2$ is the mass of the ion, then the internal force exerted on $m_1$ by $m_2$ is $\vec{F}_{12}$, the internal force exerted on $m_2$ by $m_1$ is $\vec{F}_{21}$, the external force exerted on $m_1$ is $\vec{F}_{ext,1}$, and the external force exerted on $m_2$ is $\vec{F}_{ext,2}$. When Newton's Force Law is applied to each particle, $$\vec{F}_{ext,1} + \vec{F}_{12} = m_1 \vec{a}_1 \tag{6}$$

$$\vec{F}_{ext,2} + \vec{F}_{21} = m_2 \vec{a}_2 \tag{7}$$

where $\vec{a}_1$ and $\vec{a}_2$ are the accelerations of $m_1$ and $m_2$ in the laboratory frame of reference, and $$\vec{F}_{ext,1} + \vec{F}_{ext,2} + \vec{F}_{12} + \vec{F}_{21} = m_1 \vec{a}_1 + m_2 \vec{a}_2 = M \vec{a}_{cm} \tag{8}$$

For elastic collisions in three dimensions, $\vec{F}_{12} = -\vec{F}_{21}$ and $$\Sigma \vec{F}_{ext} = m_1 \vec{a}_1 + m_2 \vec{a}_2 = M \vec{a}_{cm} \tag{9}$$

But when an ion responds to an electric field (the situation for the present invention), motion in only one-direction is of importance. In that direction $F_{12}$ is not equal to $-F_{21}$ and $$\frac{d}{dt}F_{12} + \frac{d}{dt}F_{21} = -\frac{d}{dt}P_{col} \tag{10}$$

where the right-hand differential represents a loss in directional momentum due to scattering. Mason and McDaniel in their book entitled *Transport Properties of Ions in Gases* (Wiley: New York, 1988) argue that this differential is equal to $\mu v(\in)v_d$ (equation 5-2-8 of Mason and McDaniel), where $\mu$ is the reduced mass, $v(\in)$ is the collision frequency, $\in$ is the mean relative energy, and $v_d$ is the drift velocity for the ion. If the direction of motion is in the r-direction, equations 8 to 10 become ($m_2 = m_{ion}$)

$$\sum \vec{F}_{ext} = m_{ion}\frac{d^2\vec{r}}{dt^2} + \mu v(\epsilon)\frac{d\vec{r}}{dt} = q\vec{E} \tag{11}$$

where $v_d$ has been written as $$\frac{d\vec{r}}{dt}$$

and $\vec{a}_{cm}$ has been written as $$\frac{m_{ion}}{m_1 + m_{ion}}\frac{d^2r}{dt^2}.$$

A correction for the laboratory frame of reference has been made. When equation 11 is reorganized, it becomes $$m_{ion}\frac{d^2\vec{r}}{dt^2} + \mu v(\epsilon)\frac{d\vec{r}}{dt} - q\vec{E} = 0 \qquad (12)$$

which is a general relationship describing the motion for the ion. Equation 12 reduces to Newton's Force Law when the pressure, and hence $v(\epsilon)$, goes to zero; and reduces to $v_d$=KE (where K is the mobility constant) when there is no acceleration.

According to the Chapman-Enscog theory, the ratio $q/\mu v$ ($\epsilon$) is related to the mobility constant, K, through $$K = \frac{q}{\mu v(\epsilon)} = \frac{3q}{16N}\left(\frac{2\pi}{\mu k T_{eff}}\right)^{1/2}\frac{1}{\Omega^{(1,1)}(T_{eff})} \qquad (13)$$

where N is the neutral gas density, k is the Boltzmann constant, $\Omega^{(1,1)}(T_{eff})$ is the collision cross section, T is the drift temperature, and $T_{eff}$=T +$Mv_d^2$/3k is the effective ion temperature. When equation 13 is combined with equation 12, the expanded equation of motion !becomes $$m_{ion}\frac{d^2\vec{r}}{dt^2} + \frac{16}{3}\sqrt{\frac{\mu k T_{eff}}{2\pi}} N\Omega^{(1,1)}(T_{eff})\frac{d\vec{r}}{dt} - q\vec{E} = 0 \qquad (14)$$

E. W. McDaniel in his book entitled *Atomic Collisions: Electron and Photon Projectiles* (Wiley, New York, 1989) states that the collision cross section, $\Omega^{(1,1)}(T_{eff})$ is related to the interaction potential that accompanies the collision between the ion and the neutral gas molecule (assumed to be in excess). J. O. Hirschfelder, C. F. Curtiss and R. B. Bird in chapter 3 of their book entitled *Molecular Theory of Gases and Liquids* (Wiley: New York, 1954) state that there are basically two types of interactions that can occur: (1) an hard core (or nearly hard core since angular momentum plays a role) interaction that is typically described by either an infinite potential or a Lennard-Jones (6–12) potential, and (2) an induced quadrupole interaction between the ionic charge and the neutral molecules. E. A. Mason and H. W. Schamp in a paper published in *Annals of Physics*, volume 4 (1958), pp. 233–270 note that when these two interactions are combined, a 12-6-4 potential can be defined such that the interaction potential becomes $$V(r) = \frac{\epsilon}{2}\left[(1+\gamma)\left(\frac{r_m}{r}\right)^{12} - 4\gamma\left(\frac{r_m}{r}\right)^6 - 3(1-\gamma)\left(\frac{r_m}{r}\right)^4\right] \qquad (15)$$

In equation 15, $\epsilon$=$(e^2\alpha_p)/(3r_m^2)$ is the depth of the potential energy minimum for the interaction, $r_m$ is the ion-neutral separation for the minimum potential energy, $\alpha_p$ is the polarizability of the neutral gas, and $\gamma$ is a parameter used to adjust the relative strength of the hard core versus the induced quadrupole interaction. For an ion which resonates charge throughout its molecular structure, a correction must be made to equation 15 to account for uncertainties in charge location. In a paper published in the *Journal of Physics B: Atomic and Molecular Physics*, volume 5 (1972), pp. 169–176, E. A. Mason, H. O'Hara and F. J. Smith proposed a core model for this purpose. The core model states that $$V(r) = \frac{\epsilon}{2}\left[\left(\frac{r_m - a}{r - a}\right)^{12} - 3\left(\frac{r_m - a}{r - a}\right)^4\right] \qquad (16)$$

where "a" is the core diameter (a parameter that may depend upon the isomer being investigated). To relate the interaction potentials of equations 15 and 16 with the collision cross section, collision theory normally breaks the collision cross section, $\Omega^{(1,1)}(T_{eff})$, into two parts: the hard core cross section, $\pi r_m^2$, and a multiplicative dimensionless parameter, $\Omega^{(1,1)*}(T_{eff})$. That is, $\Omega^{(1,1)}(T_{eff})$=$\pi r_m^2 \Omega^{(1,1)*}(T_{eff})$. $\Omega^{(1,1)*}(T_{eff})$ is a function of the effective temperature, $T_{eff}$, or energy of the ion, and in the case of the core model, the core diameter, "a". Values for $\Omega^{(1,1)*}(T_{eff})$ are available in the open scientific literature for both the 12-6-4 (equation 15) and the core (equation 16) models described above. G. E. Spangler (the inventor assigned to the present invention) has observed that equation 12 can be used to fit mobility data generated by a conventional linear IMS using either the core model of equation 16, or a hard core (defined by $\Omega^{(1,1)*}(T_{eff})$=1) model (Scientific Conference on Chemical and Biological Defense Research, Aberdeen Proving Ground, Md. November, 1995; and Fifth International Workshop on Ion Mobility Spectrometry, Jackson, Wyo., August 1996). A conventional linear IMS uses a constant electric field to separate ions, as opposed to an AC field as described in this invention.

The electric field generated in the IMST of FIG. 15 when using the asymmetric potential of FIG. 19

$$E_r(r, t) = -2\frac{U + V_1\cos\omega t + V_2\cos 2\omega t}{r_0^2 + 2z_0^2}r \qquad (17)$$

$$E_z(r, t) = 4\frac{U + V_1\cos\omega t + V_2\cos 2\omega t}{r_0^2 + 2z_0^2}z \qquad (18)$$

where U is the DC potential, $V_1$ and $V_2$ are the magnitudes for the superimposed AC potentials, $\omega$ is the AC frequency, and $r_0$ and $z_0$ are the internal dimensions of the quadrupole trap. When these expressions for the electric fields are substituted into equation 14, the equation of motion becomes $$m_{ion}\frac{d^2 r}{dt^2} + \frac{16}{3}\sqrt{\frac{\mu k T_{eff}}{2\pi}} N\Omega^{(1,1)}(T_{eff})\frac{dr}{dt} + \qquad (19)$$

$$2q\left[\frac{U + V_1\cos\omega t + V_2\cos 2\omega t}{r_0^2 + 2z_0^2}\right]r = 0$$

$$m_{ion}\frac{d^2 z}{dt^2} + \frac{16}{3}\sqrt{\frac{\mu k T_{eff}}{2\pi}} N\Omega^{(1,1)}(T_{eff})\frac{dz}{dt} - \qquad (20)$$

$$4q\left[\frac{U + V_1\cos\omega t + V_2\cos 2\omega t}{r_0^2 + 2z_0^2}\right]z = 0$$

in the r- and z-directions, respectively. Since $T_{eff}$ depends on the square of the ion velocity, these equations are non-linear and require numerical methods for their evaluation. Rosenbrock's techniques can be used for this purpose as they are implemented in Mathcad Plus 6.0, a computational software package available from MathSoft, Inc., Cambridge, Mass.

The first observation that can be made on equations 19 and 20 is that they reduce to the Mathieu equation when the pressure (and hence the number density, N) goes to zero and $V_2$ is set equal to zero. This condition corresponds to the condition typically used to separate ions in a quadrupole ion trap mass spectrometer (ITMS). FIGS. 20, 21, 22 and 23 show solutions to equations 19 and 20 using this condition with the following operating parameters:

EXAMPLES 1–4

| | |
|---|---|
| Sample | Mesitylene |
| Carrier Gas | Purified Air (absolutely no impurities) |
| Pressure | $1 \times 10^{-6}$ mm Hg (Example 1, FIG. 20), |
| | $5 \times 10^{-3}$ mm Hg (Examples 2, 3, and 4, FIGS. 21, 22, and 23, respectively) |
| Temperature | 50° C. |
| $r_0$ | 5 mm |
| $z_0$ | 5 mm |
| U | 0 volts |
| $V_1$ | 1 volt (Examples 1 and 2) |
| | 2.75 volts (Example 3) |
| | 8.0 volts (Example 4) |
| $V_2$ | 0 volts |
| ω | 500 kilocycles/sec |
| initial conditions | $r_i = 1$ mm, $dr_i/dt = 0$, $z_i = 5$ mm, $dz_i/dt = 0$ |
| collision model | hard core |

Figure 20A:
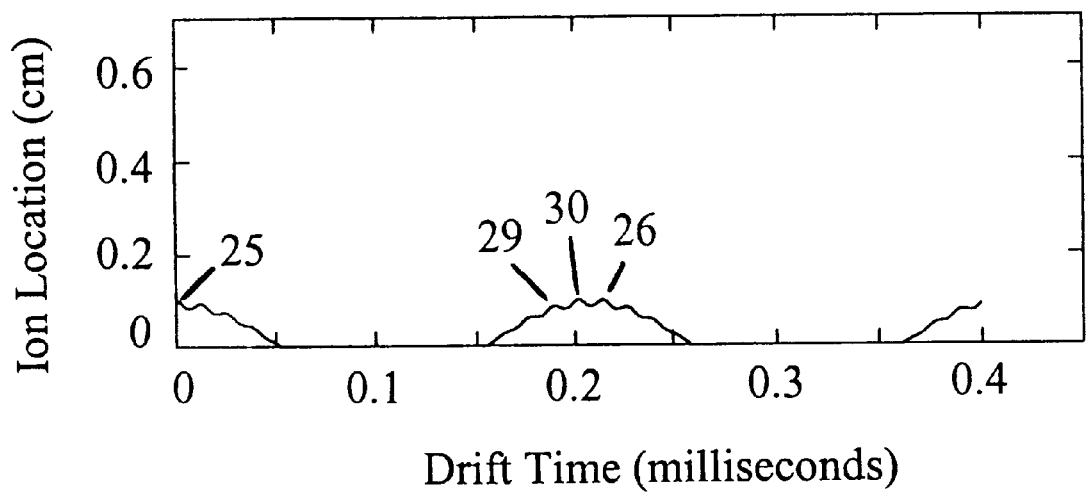
FIGS. 20A and 20B show the ion trajectories for a mesitylene cation in a AC-only quadrupole ion trap when operated at a pressure of $1 \times 10^{-6}$ mm Hg. The top plot shows the trajectory in the redirection and the bottom plot shows the trajectory in the z-direction.
Figure 20B:
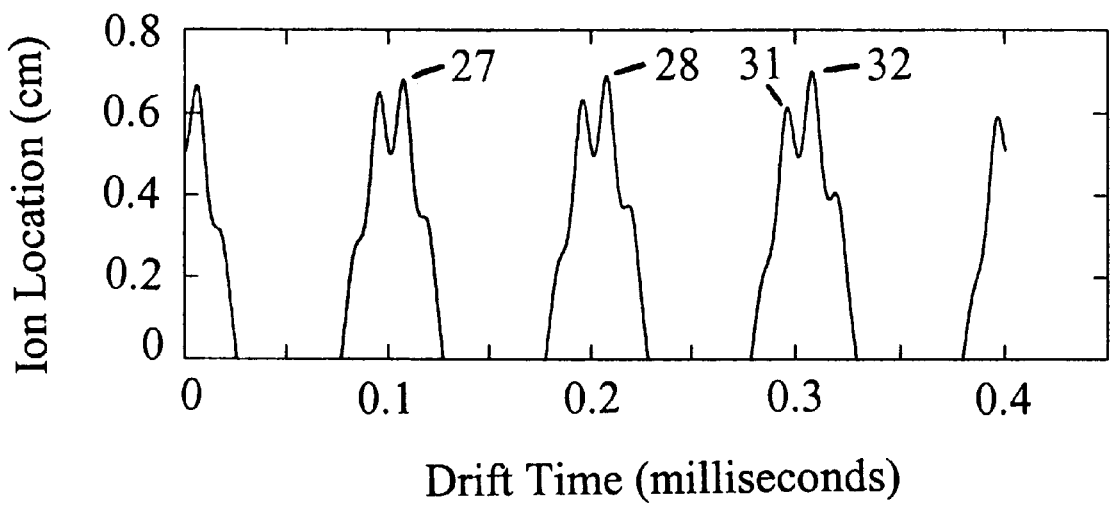
Figure 21A:
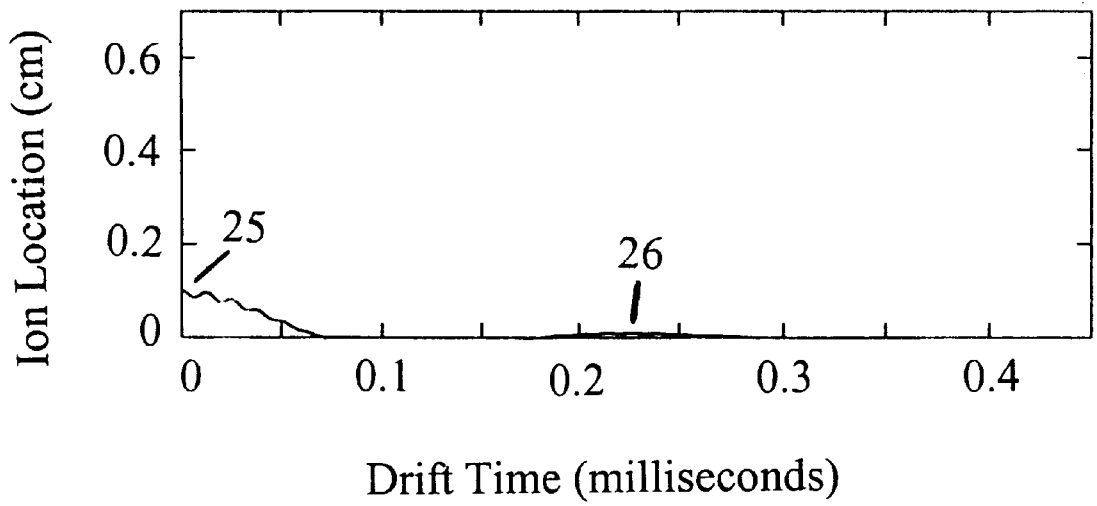
FIGS. 21A and 21B show the ion trajectories for a mesitylene cation in an AC-only quadrupole ion trap when operated at a pressure of $5 \times 10^{-3}$ mm Hg. Except for pressure, the operating conditions are the same as in FIG. 20.
Figure 21B:
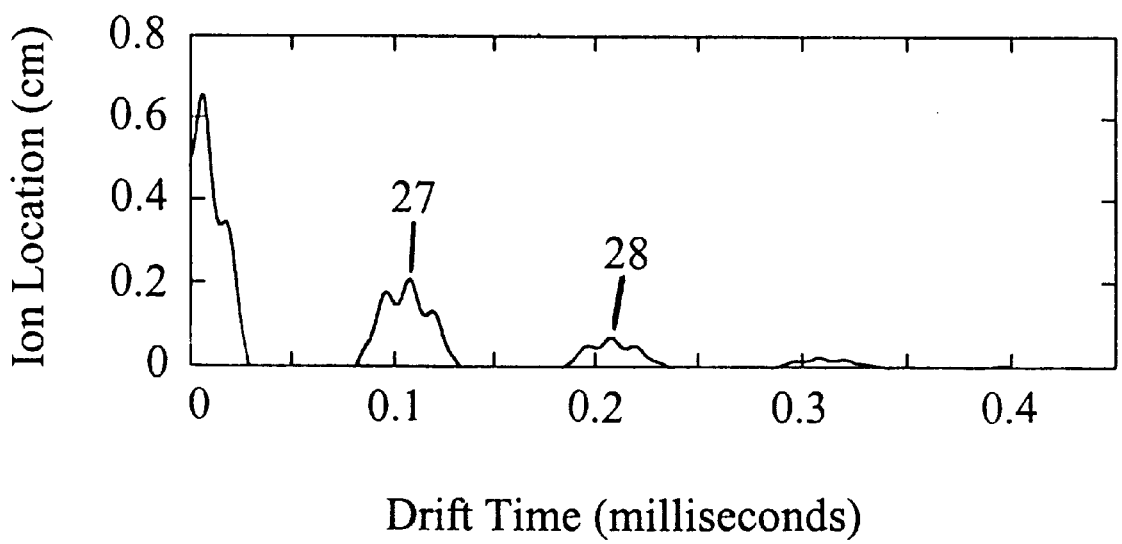
Figure 22A:
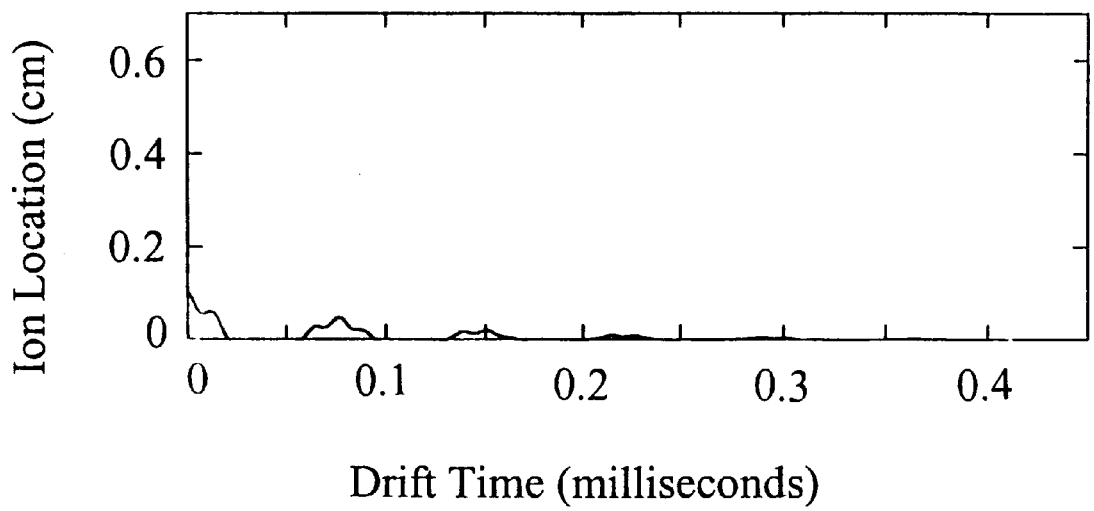
FIGS. 22A and 22B show the ion trajectories for a mesitylene cation in the AC-only quadrupole ion trap of FIG. 21 after the AC-voltage was increased from 1 volt peak-to-peak to 2.75 volts peak-to-peak.

Equation 19 was used to obtain the plots illustrated in FIGS. 20A, 21A, 22A, acid 23A (showing the movement of the ionized sample in the r-direction) and equation 20 was used to obtain the plots illustrated in FIGS. 20B, 21B, 22B, and 23B (showing the movement of the ionized sample in the z-direction). The mesitylene ion oscillates in both the r- and z-directions about r=0 and z=0. The secular frequency for the oscillations is $$\omega = \frac{2\pi}{\Delta t} \quad (21)$$

where Δt is the time difference between points 25 and 26, and points 27 and 28 in FIGS. 20 and 21. The secular frequencies are approximately 29 kilocycles/second and 63 kilocycles/second in the r- and z-directions, respectively. Similar data for the benzene cation shows that the secular frequencies are 126 kilocycles/second and 251 kilocycles/second, respectively. That is the secular frequency is mass dependent. Superimposed on the secular frequency is a much faster oscillation indicated by points 29, 30 and 31, 32 in FIG. 20. The time difference between these points corresponds to approximately 500 kilocycles/second, a residual of the drive frequency. The amplitude of the secular oscillations are fairly pronounced and constant below about $5 \times 10^{-4}$ mm Hg. However as the pressure is raised, they are damped. This is evident in FIG. 21 that illustrates the results for Example 2 with a pressure of $5 \times 10^{-3}$ mm Hg and $V_1=1$ volt.

Figure 22B:
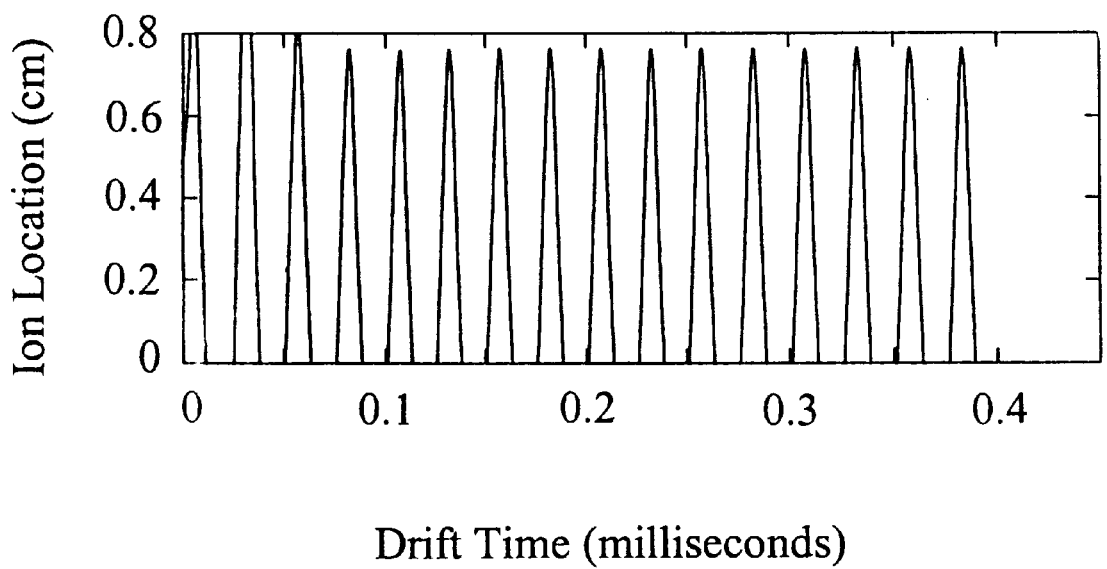
Figure 23A:
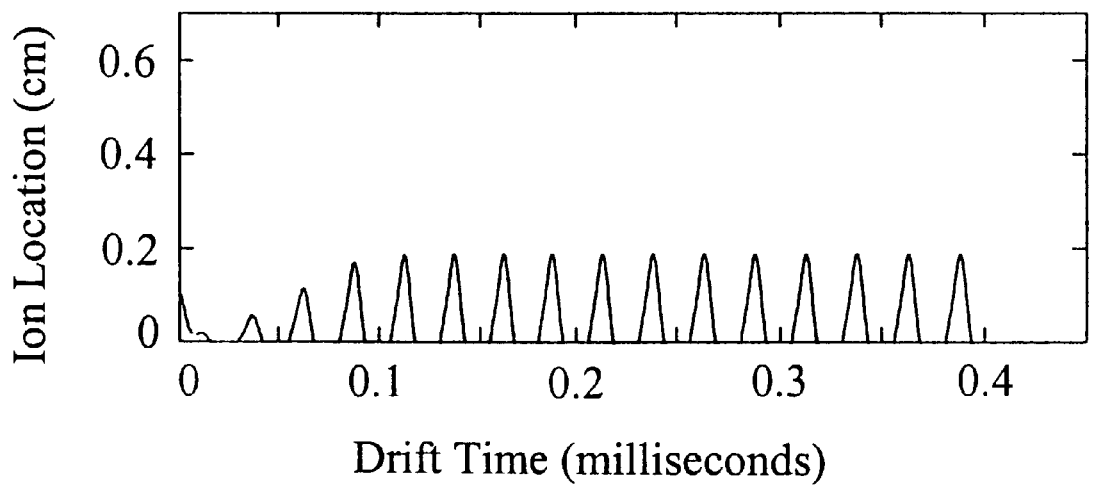
FIGS. 23A and 23B show the ion trajectories for mesitylene cation in the AC-only quadrupole ion trap of FIG. 21 after the AC-voltage was increased from 1 volt peak-to-peak to 8.0 volts peak-to-peak.
Figure 23B:
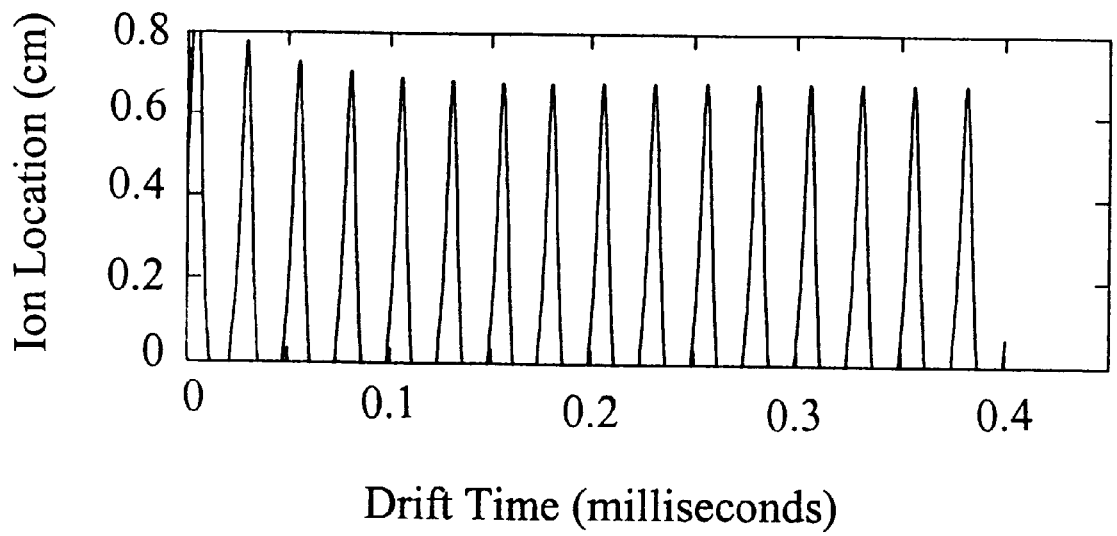
Figure 24A:
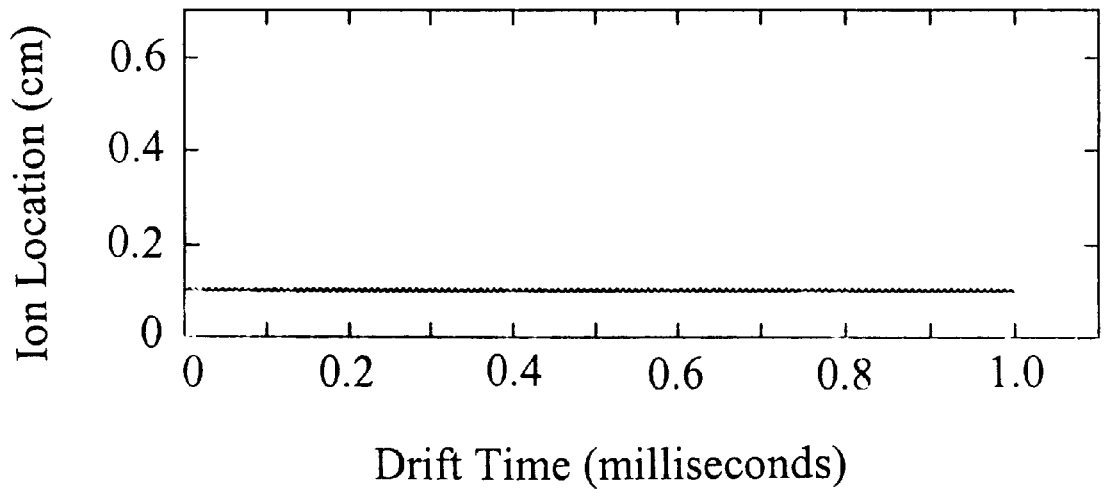
FIGS. 24A and 24B show the ion trajectories for a mesitylene cation in an AC-only quadrupole ion mobility storage trap when operated at a pressure of 200 mm Hg.
Figure 24B:
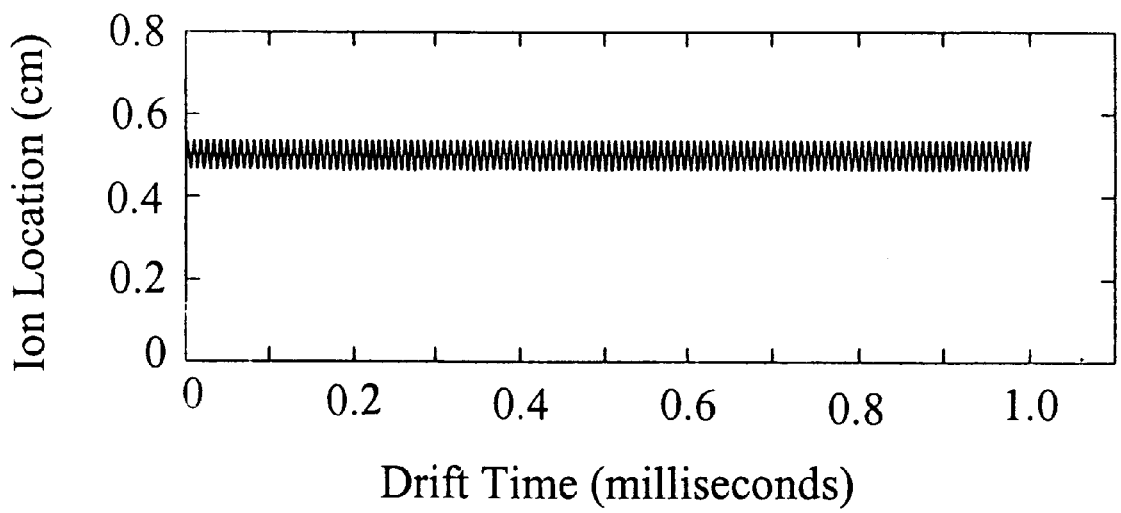
Figure 25A:
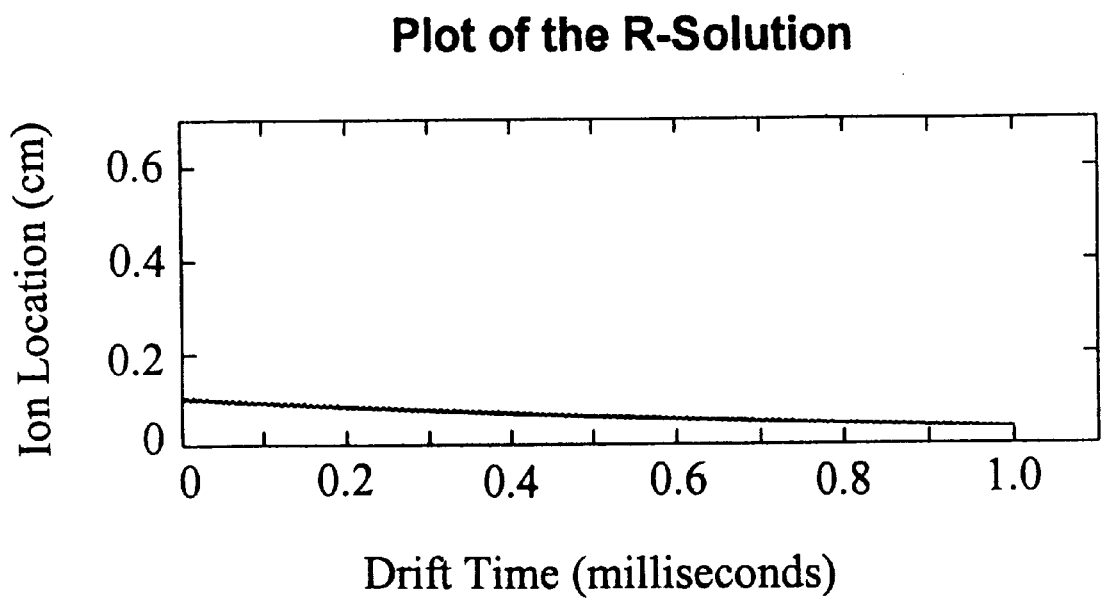
FIGS. 25A and 25B show the ion trajectories for a mesitylene cation in the quadrupole ion mobility storage trap of FIG. 24 after a DC potential (40 volts) is added to the AC potential (1200 volts) already applied to the ring-electrode.
Figure 25B:
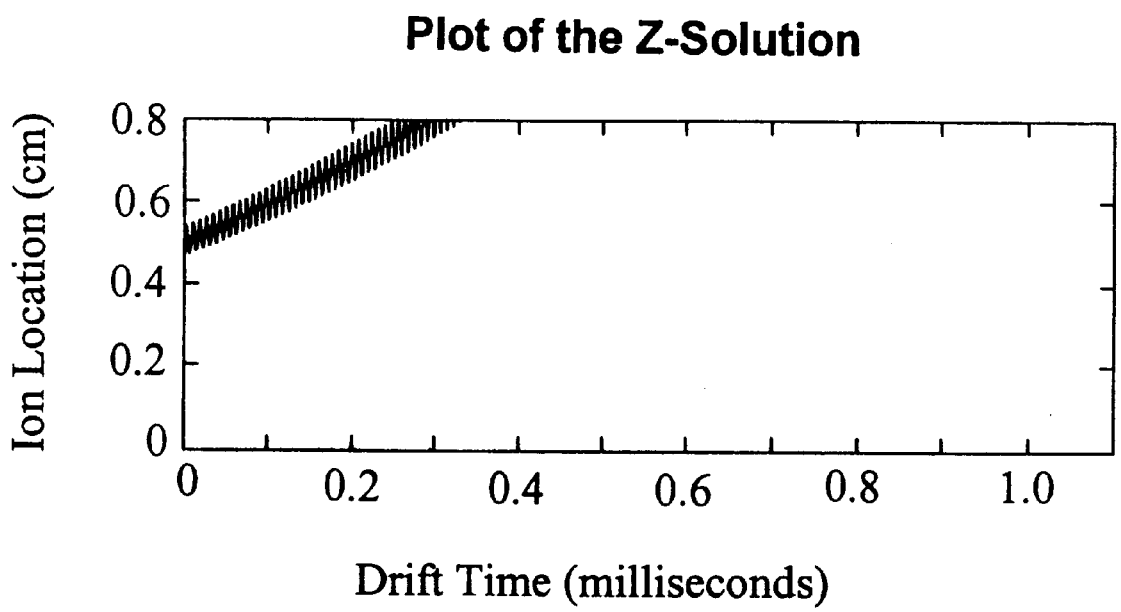
Figure 26A:
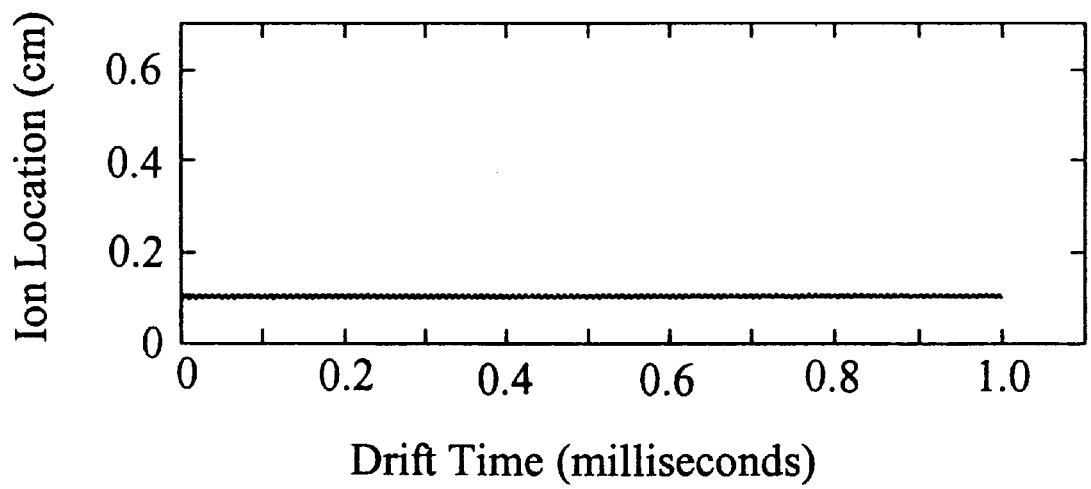
FIGS. 26A and 26B show the ion trajectories for a mesitylene cation in the quadrupole ion mobility storage trap of FIG. 24 after an AC potential and its second harmonic ($V_1 = 2V_2$) are applied to the ring-electrode.
Figure 26B:
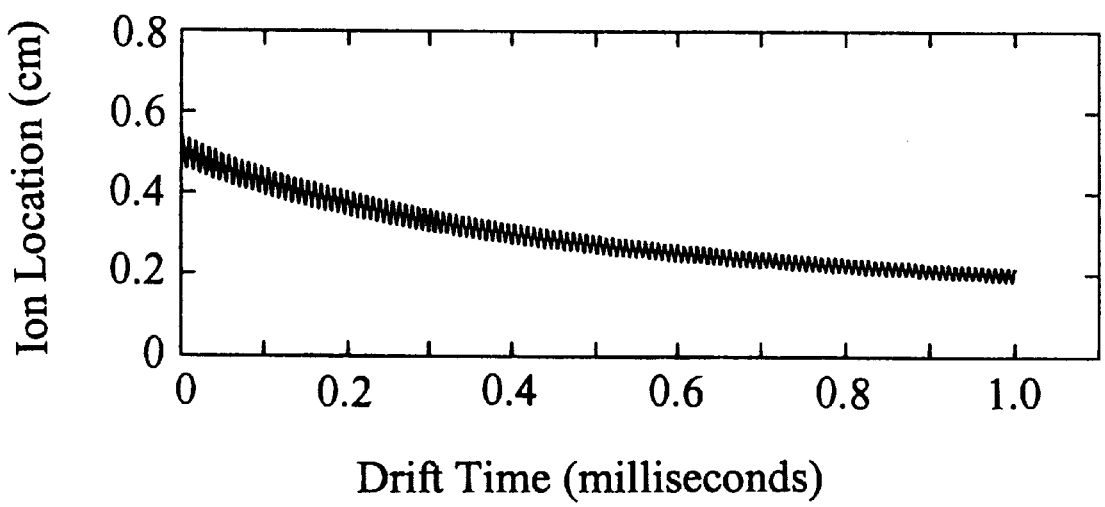
Figure 27A:
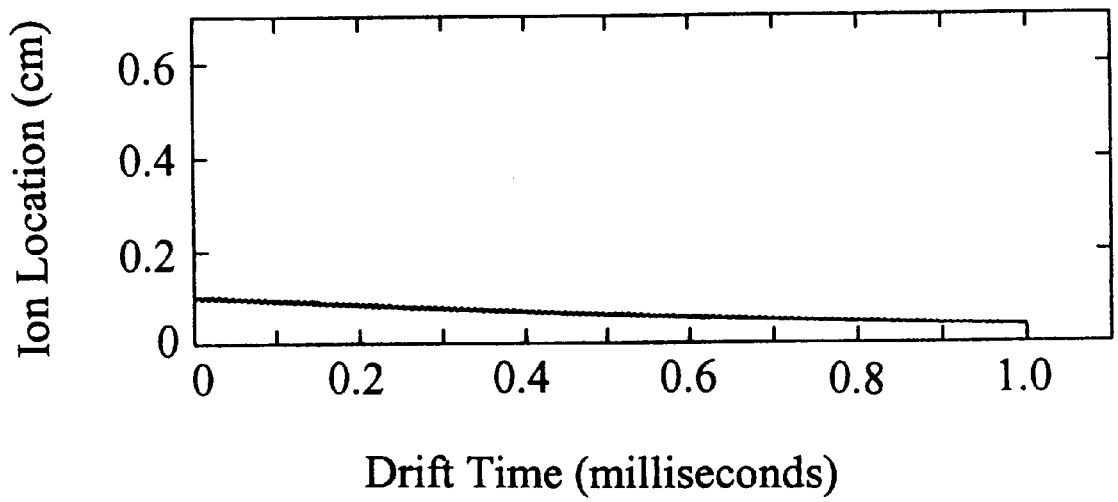
FIGS. 27A and 27B show that the ion trajectories for a mesitylene cation in the quadrupole ion mobility storage trap of FIG. 26 after a DC potential (40 volts) is added to the ring-electrode. The ion is introduced near an end-cap at x=5 mm.
Figure 27B:
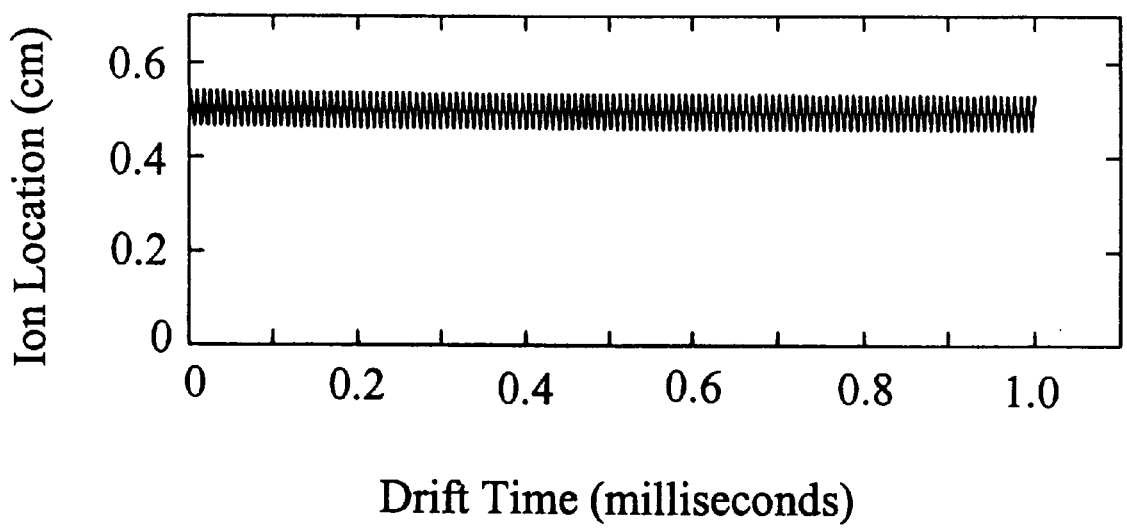
Figure 28A:
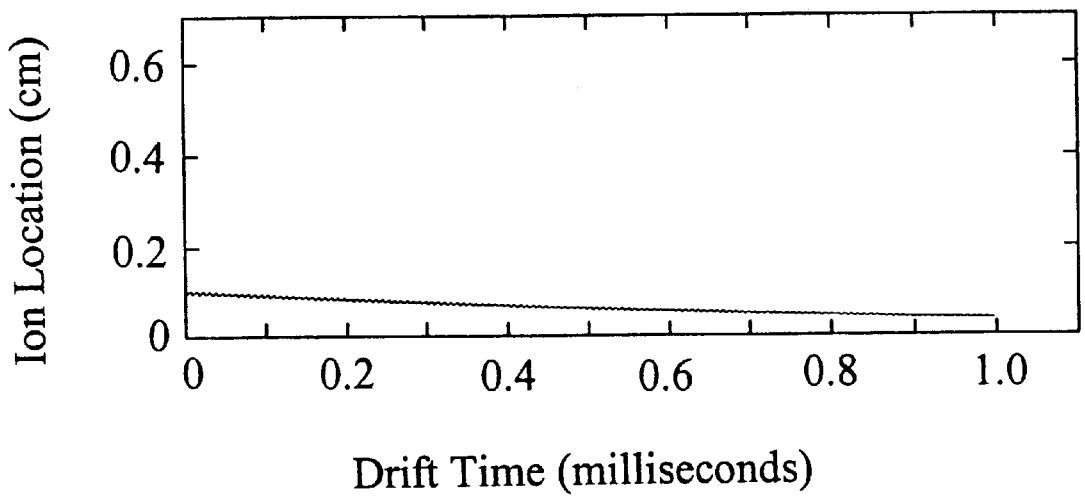
FIGS. 28A and 28B show the ion trajectories for a mesitylene cation in quadrupole ion mobility storage trap of FIG. 26 after a DC potential (40 volts) is added to the ring-electrode. The ion is introduced near the center of the trap at z=1 mm.
Figure 28B:
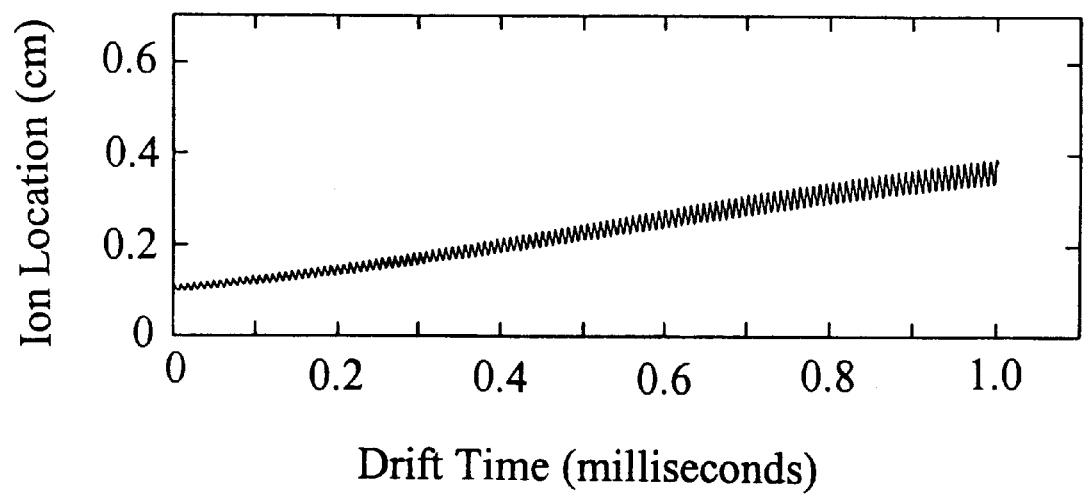

When $V_1$ is increased in Example 2 (FIG. 21), the secular frequency increases and approaches that for the drive frequency. FIG. 22 shows the result for Example 3 where $V_1$ equals 2.75 volts and the secular frequency is about 250 kilocycles/second in the z-direction (FIG. 22A) and 84 kilocycles/second in the redirection (FIG. 22B). FIG. 23 shows the result for Example 4 where $V_1$ equals 8.0 volts and the secular frequency is about 250 kilocycles/second in both directions. Further to increases in potential lead only to increased amplitudes for the oscillations with no further changes in frequencies. This region of higher pressure, potentials and secular frequencies is the region of interest for the present invention.

The ion separation capability for the present invention at higher pressure is illustrated in FIGS. 24 to 34. FIGS. 24 to 28 (Examples 5–9, respectively) show solutions to equations 19 and 20 using the following set of operating conditions:

EXAMPLES 5–9

| | |
|---|---|
| Sample | Mesitylene |
| Carrier Gas | Purified Air (absolutely no impurities) |
| Pressure | 200 mm Hg |
| Temperature | 50° C. |
| $r_0$ | 5 mm |
| $z_0$ | 5 mm |
| U | 0 volts (Examples 5 and 7) |
| | 40 Volts (Examples 6, 8, and 9) |
| $V_1$ | 1200 volts |
| $V_2$ | 0 volts (Examples 5 and 6) |
| | 600 Volts (Examples 7–9) |
| ω | 800 kilocycles/sec |
| initial conditions | $r_i = 1$ mm, $dr_i/dt = 0$, $z_i = 5$ mm, $dz_i/dt = 0$ |
| | (Except $z_i = 1$ mm for Example 9) |
| collision model | hard core |

For this higher pressure, higher potentials are needed to induce oscillations in the ions. Example 5 (FIG. 24) shows that the mesitylene ion is not deflected in the trap when the ring-electrode is excited only with a symmetrical AC potential of the type $V_1 \cos \omega t$. Example 6 (FIG. 25) shows that the mesitylene ion leaves the trap along the z-axis if, in addition to the AC excitation of FIG. 24, a DC potential of 40 volts is added to the ring-electrode. Example 7 (FIG. 26) shows that the mesitylene ion collapses toward the center of the trap when the ring-electrode is excited with an asymmetric AC potential of the type $V_1 \cos \omega t + V_2 \cos 2\omega t$. Example 8 (FIG. 27) shows that the 40 volts DC potential of Example 6 can be used to offset the effects of the asymmetric potential in Example 7. Example 9 (FIG. 28) shows that the mesitylene ion migrates to the same location regardless of where it is formed in the trap. That is, the ion migrates towards z=5 mm, whether it is injected at z=5 mm in Example 8 or at z=1 mm in Example 9.

Figure 29:
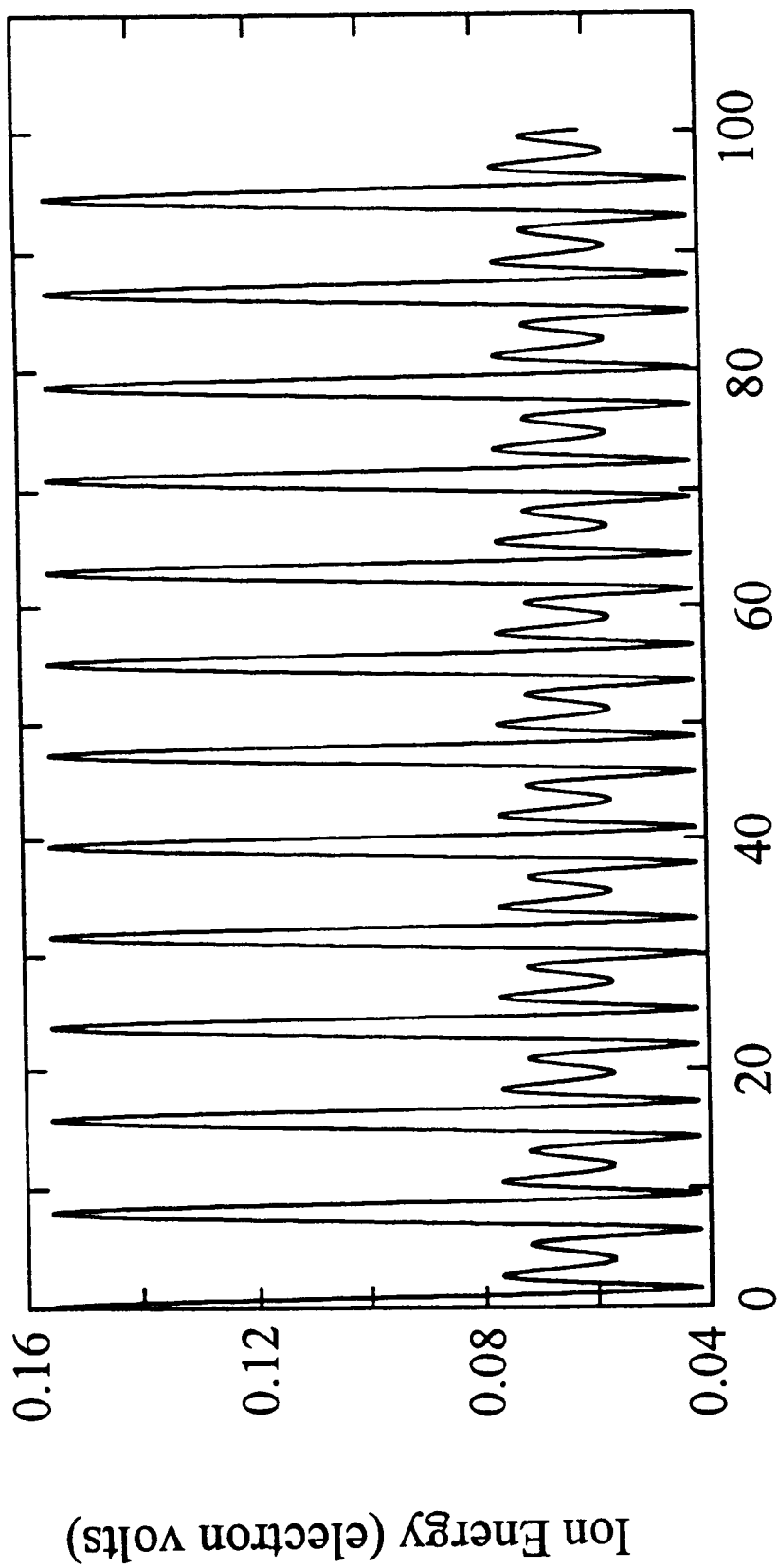
FIG. 29 shows the energy (as calculated from Wannier's expression for average ion energy) for the mesitylene cation of FIG. 27.
Figure 30A:
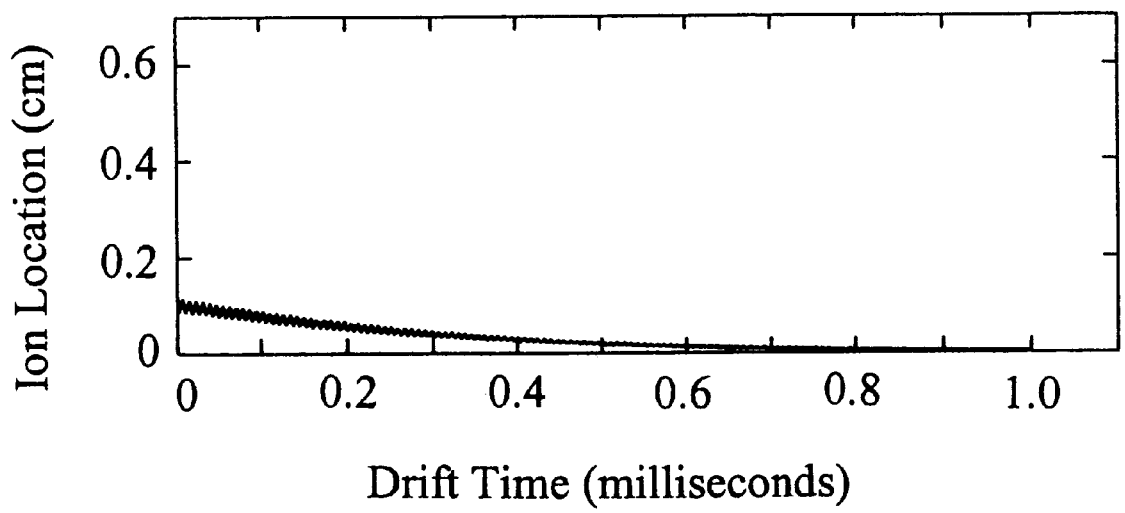
FIGS. 30A and 30B show the ion trajectories for a protonated water cation in the quadrupole ion mobility storage trap of FIG. 27.
Figure 30B:
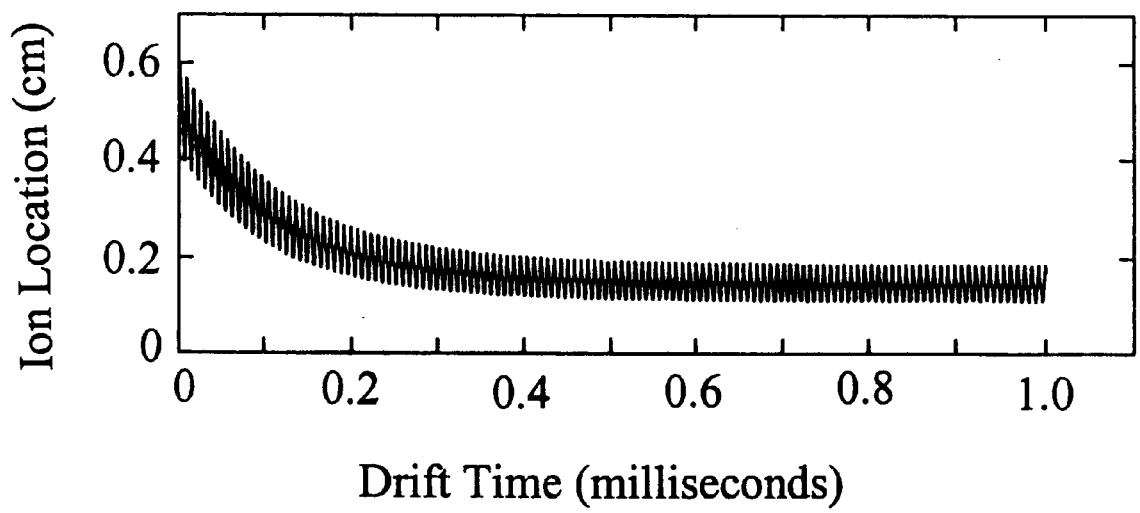
Figure 31A:
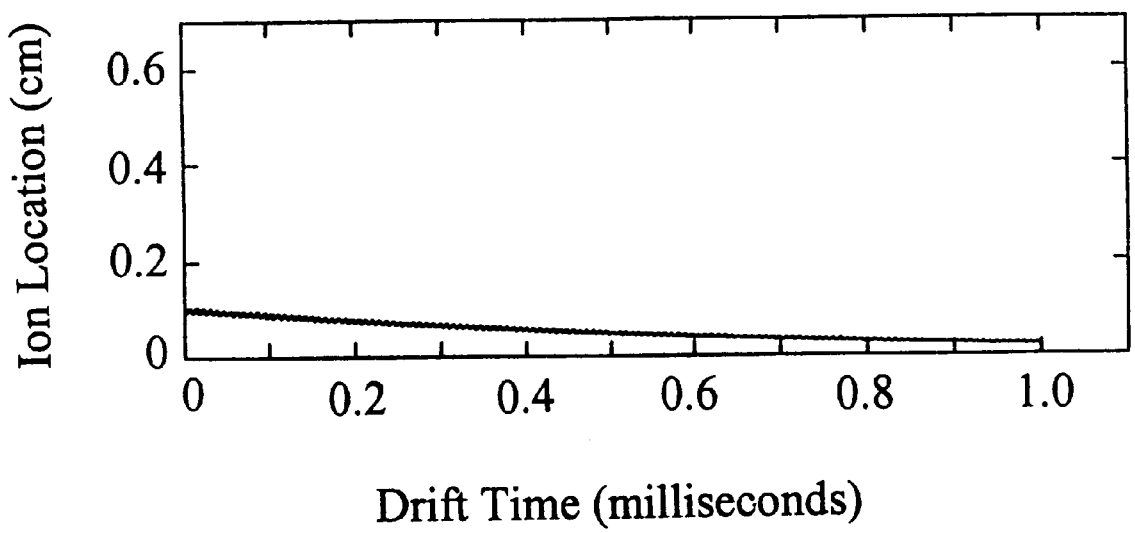
FIGS. 31A and 31B show the ion trajectories for a protonated acetone cation in the quadrupole ion mobility storage trap of FIG. 27.
Figure 31B:
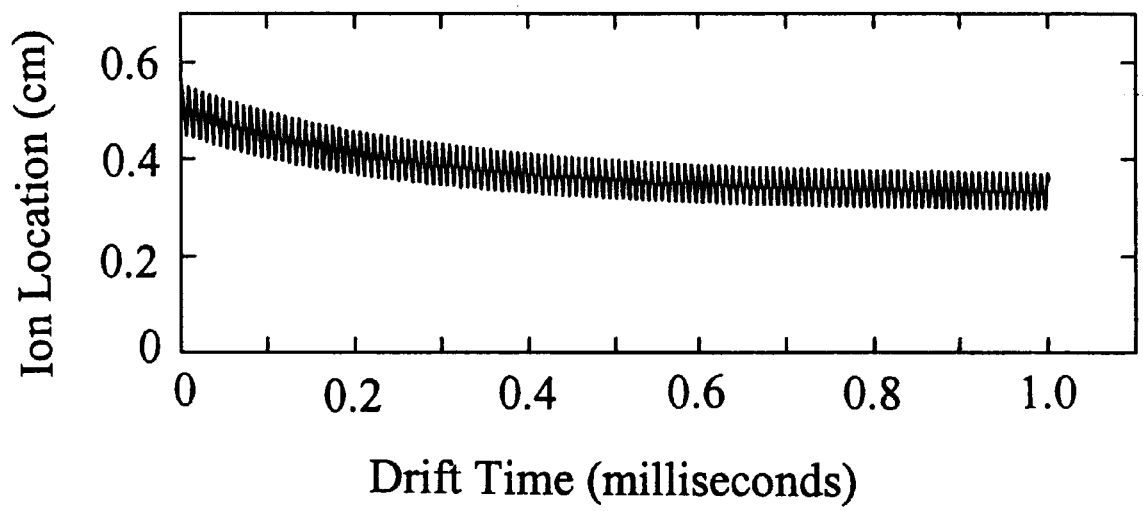
Figure 32A:
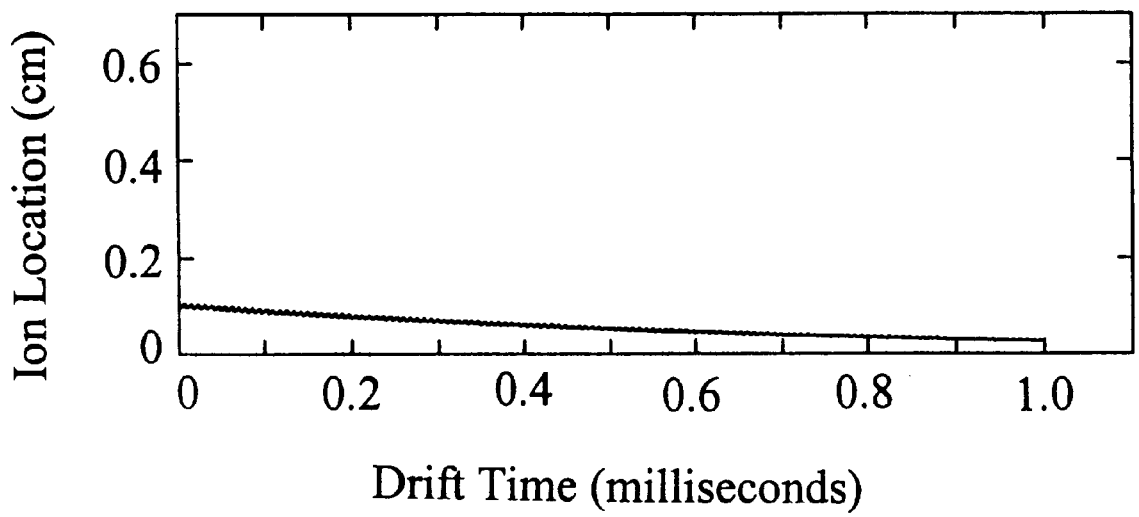
FIGS. 32A and 32B show the ion trajectories for benzene cation in the quadrupole ion mobility storage trap of FIG. 27.
Figure 32B:
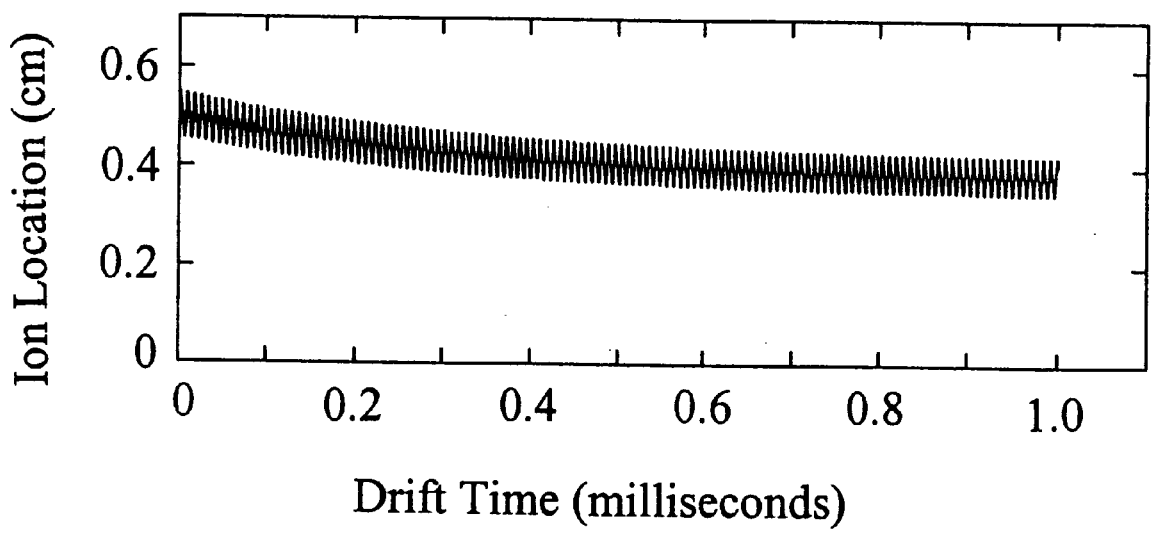
Figure 33A:
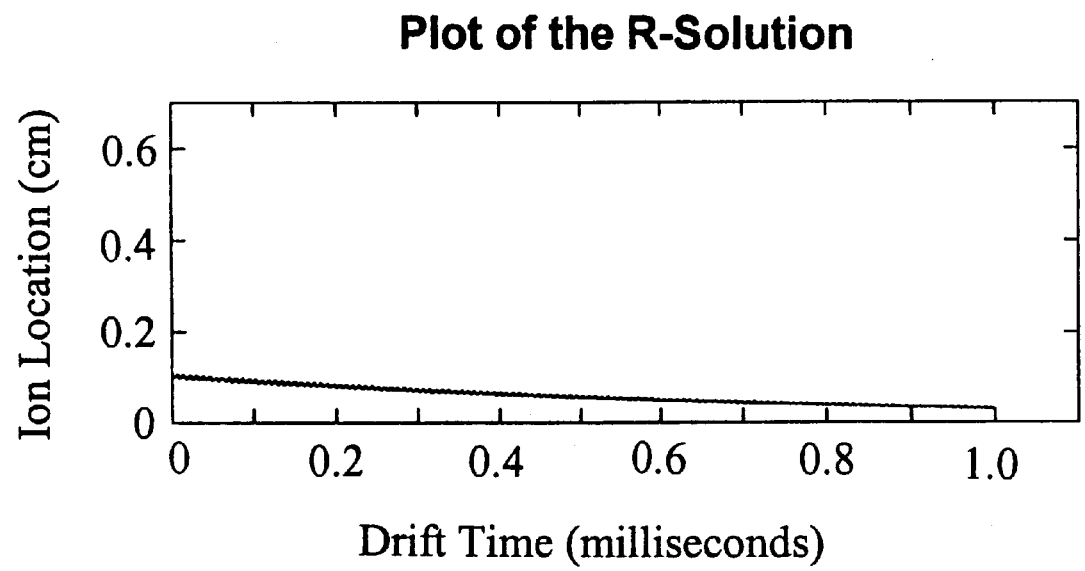
FIGS. 33A and 33B show the ion trajectories for toluene cation in the quadrupole ion mobility storage trap of FIG. 27.
Figure 33B:
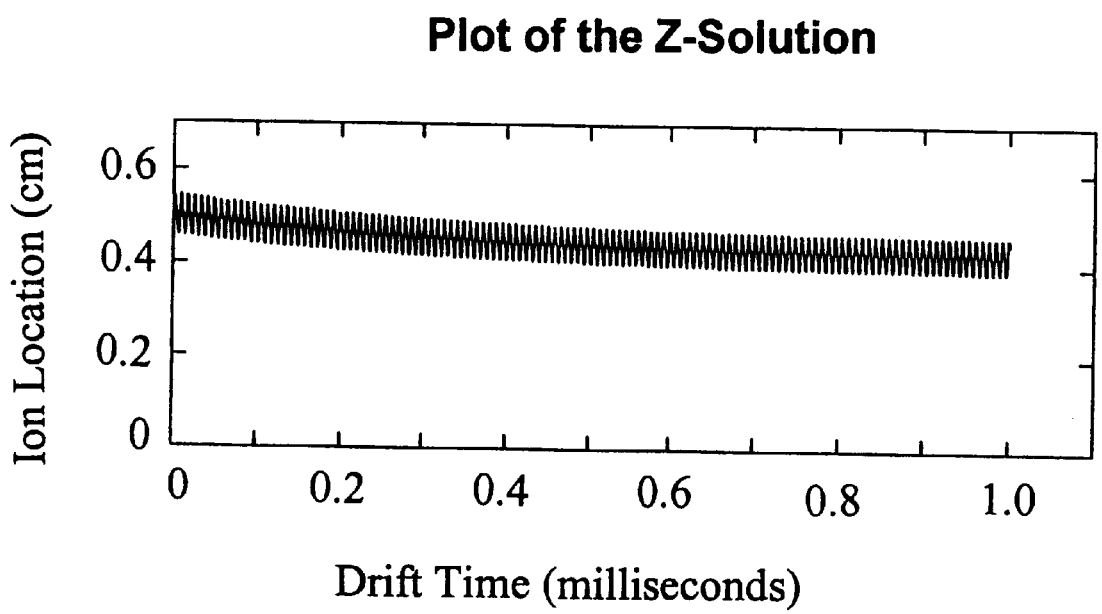
Figure 34A:
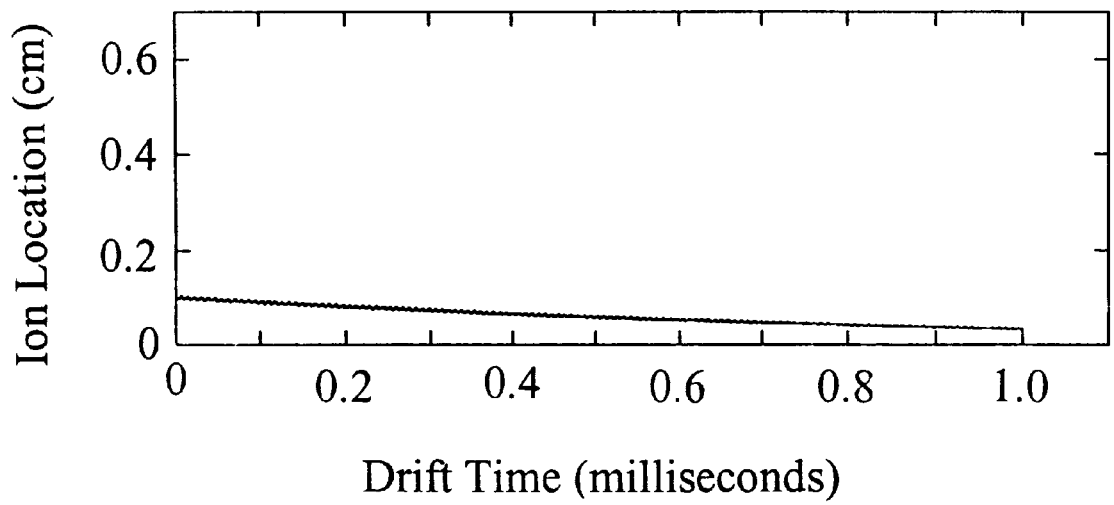
FIGS. 34A and 34B show the ion trajectories for xylene cation in the quadrupole ion mobility storage trap of FIG. 27.
Figure 34B:
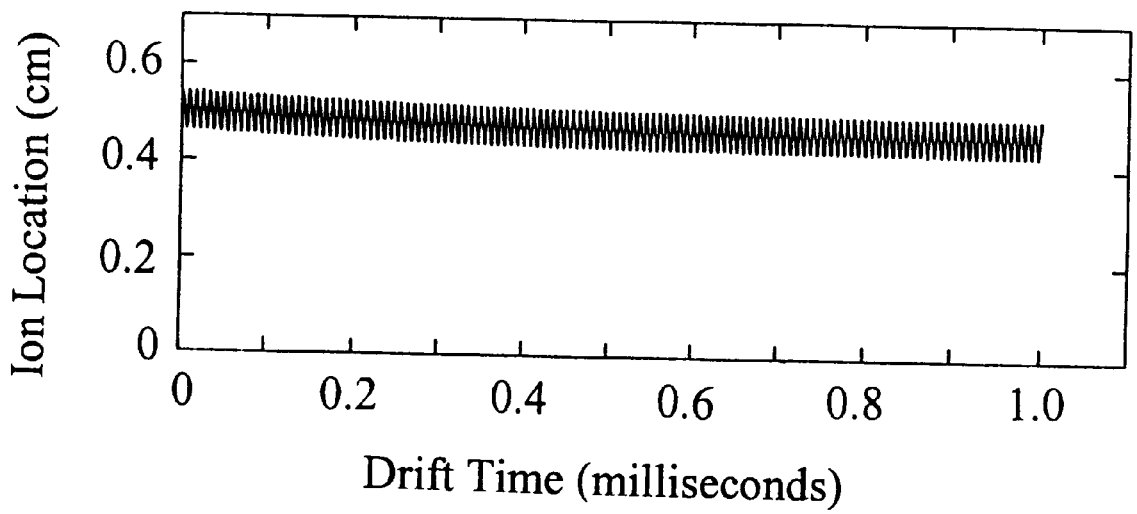

FIG. 29 shows that the energy (as calculated from Wannier's expression for the average ion energy) of the mesitylene ion in Example 8 is a periodic function of time with a maximum energy of just under 4 times thermal energy. This energy is gained from the electric field that accompanies the high potential applied to the trap. For an ion that clusters with neutrals, this energy may be sufficient to partially decluster the ion, causing the mobility to approach that for a bare ion.

FIGS. 30 to 34 show solutions to equations 19 and 20 with different ions; injected into the trap under the operating conditions of Example 8 (and 9). These examples show that molecular ions with different mass-to-charge ratios occupy different locations within the trap. They are distributed along the z-axis in the following order:

| MASS-TO-CHARGE RATIO | ION | INCREASING z |
|---|---|---|
| 18 | Water (FIG. 30) | ↓ |
| 58 | Acetone (FIG. 31) | |
| 78 | Benzene (FIG. 32) | |
| 92 | Toluene (FIG. 33) | |
| 106 | Xylene (FIG. 34) | |
| 120 | Mesitylene (FIG. 27) | |

The fractionation occurs because the electric field in a hyperbolic trap is a function of z, and the degree of fractionation is related to the energy gained by the ion from the electric field. Because ions with higher molecular weights gain less energy from the electric field, they occupy higher values of z. This is consistent with the earlier observation made on FIG. 17A where ions with greater mobility differences occupy lower values of z. By changing the polarity of one or more of the potentials, the ions can also be distributed along the r-axis of the trap.

Similar separations can also be accomplished under atmospheric pressure conditions by simply increasing the potentials involved, lowering AC frequencies, and/or reducing trap dimensions. These changes are needed to overcome the effects of the increased number of energy sapping collisions that occur in this pressure regime. An example of a good set of operating parameters for atmospheric pressure conditions is:

| Carrier Gas | Purified Air (absolutely no impurities) |
|---|---|
| Pressure | 760 mm Hg |
| Temperature | 50° C. |
| $r_0$ | 5 mm |
| $z_0$ | 5 mm |
| U | 1 Volt |
| $V_1$ | 900 Volts |
| $V_2$ | 450 Volts |
| $\omega$ | 200 kilocycles/sec |

The pressure utilized in the device may vary for each application. As shown by the above examples, it is preferable that the pressure be at least $5 \times 10^{-3}$ mm Hg. However, any pressure greater than this pressure can be utilized. The use of atmospheric pressure is particular advantageous in that vacuum pumps are not needed to support operation of the device. Pressures greater than atmospheric pressure are also possible.

Returning to the question relating to the asymmetric potential needed to excite an ion mobility storage trap, any waveform that allows equation 12 to be satisfied is satisfactory. Because of the linearity of equation 12 in the electric field, a linear combination of potentials that individually satisfy equation 12 are also satisfactory. For example, a linear combination of the waveforms in FIGS. 13 and 19 will provide a suitable asymmetric excitation potential, as will a linear combination of waveforms derived from FIGS. 13 or 19 with different frequencies. The Fourier principle suggests that a modified sawtooth waveform, a modified triangular waveform, etc. can be constructed using a weighted sum of the waveforms of the type displayed in FIG. 19 with different frequencies. On the other hand, not all waveforms will be as easy to generate, or be as effective in separating ions, as the waveform examples described in this patent.

Further Examples of Trap Structure

Figure 1:
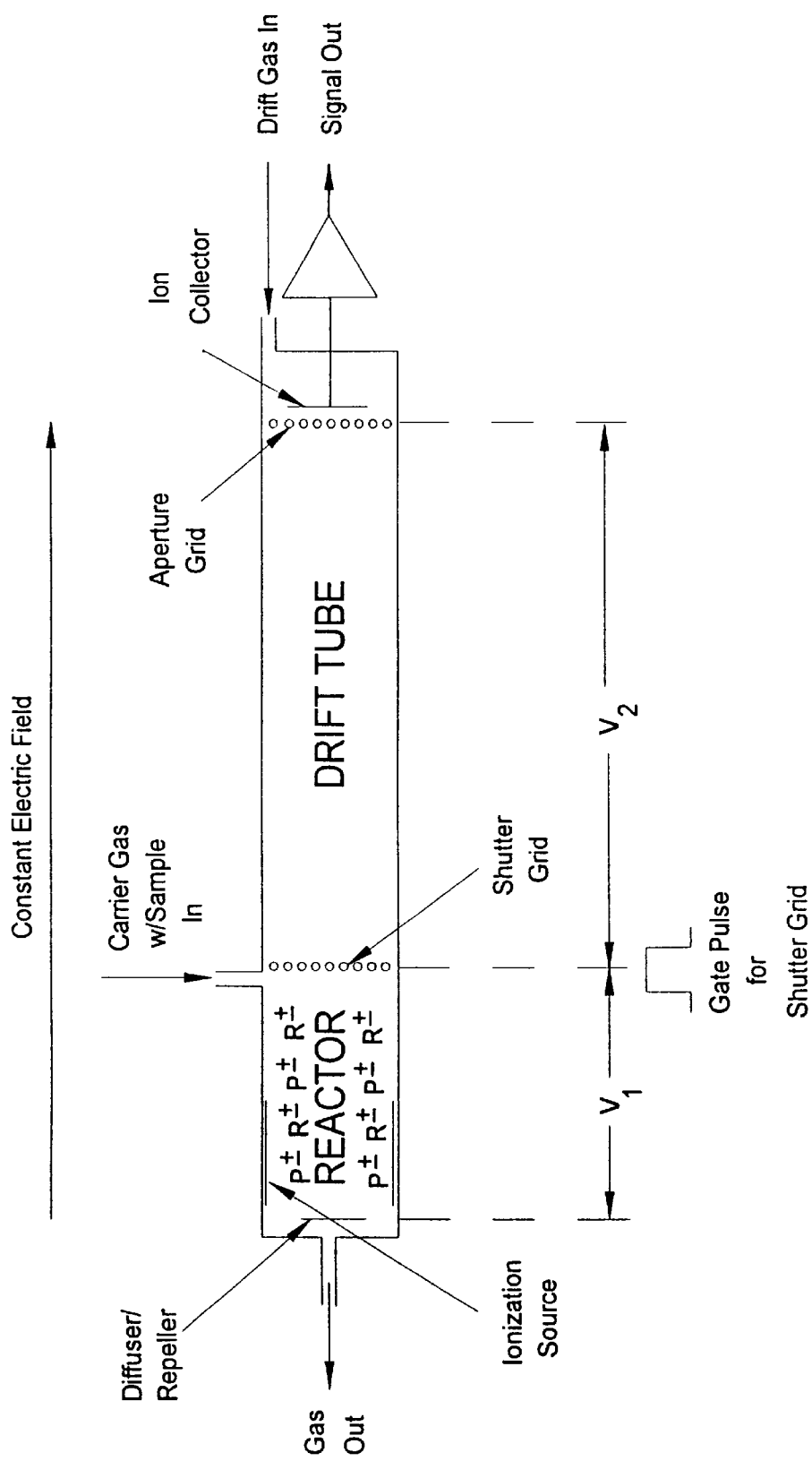
FIG. 1 is a simplified drawing illustrating the prior art for ion mobility spectrometry.
Figure 2:
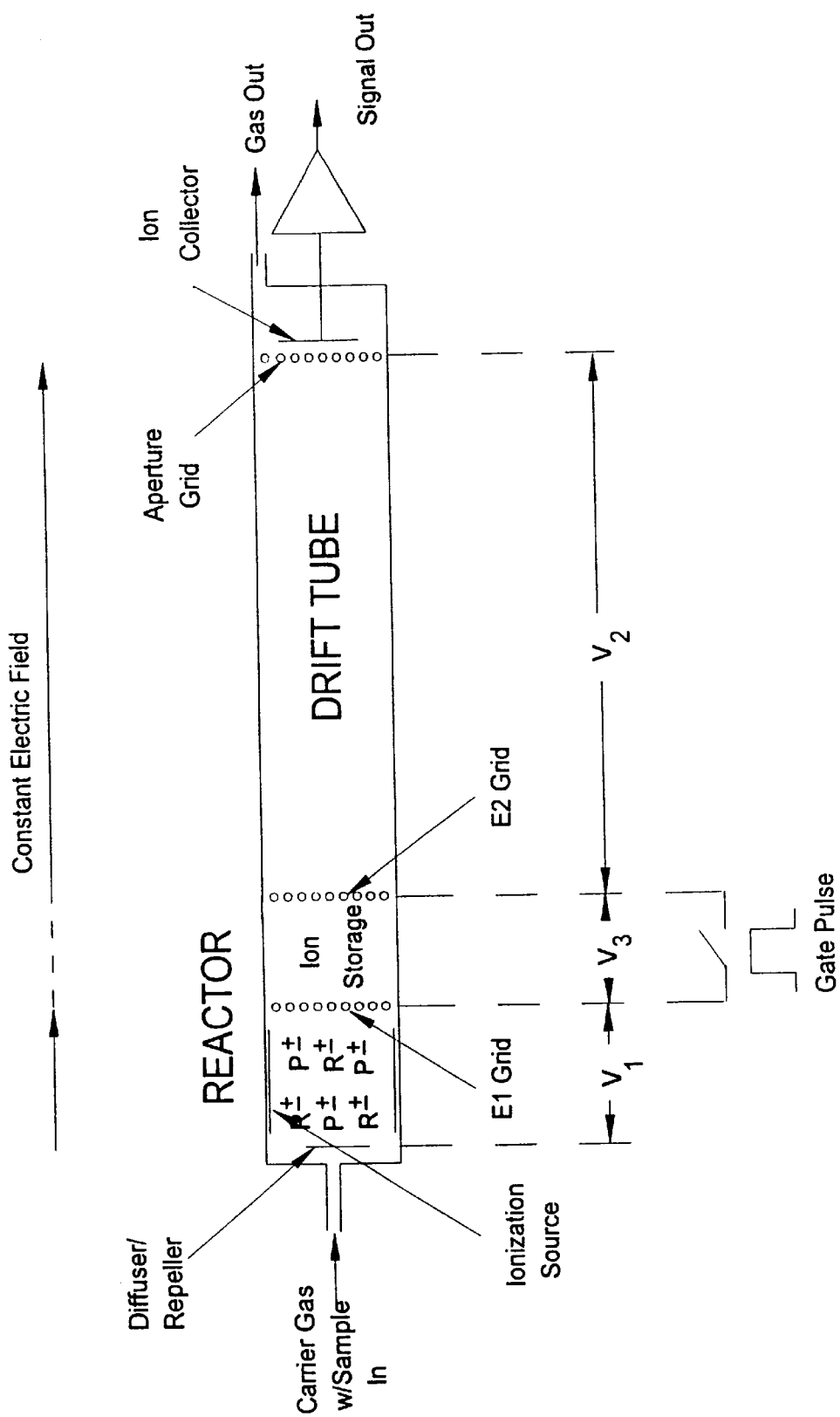
FIG. 2 is a simplified drawing for a variant of the prior art for ion mobility spectrometry, known as the "Ion Trap Mobility Spectrometer".
Figure 3:
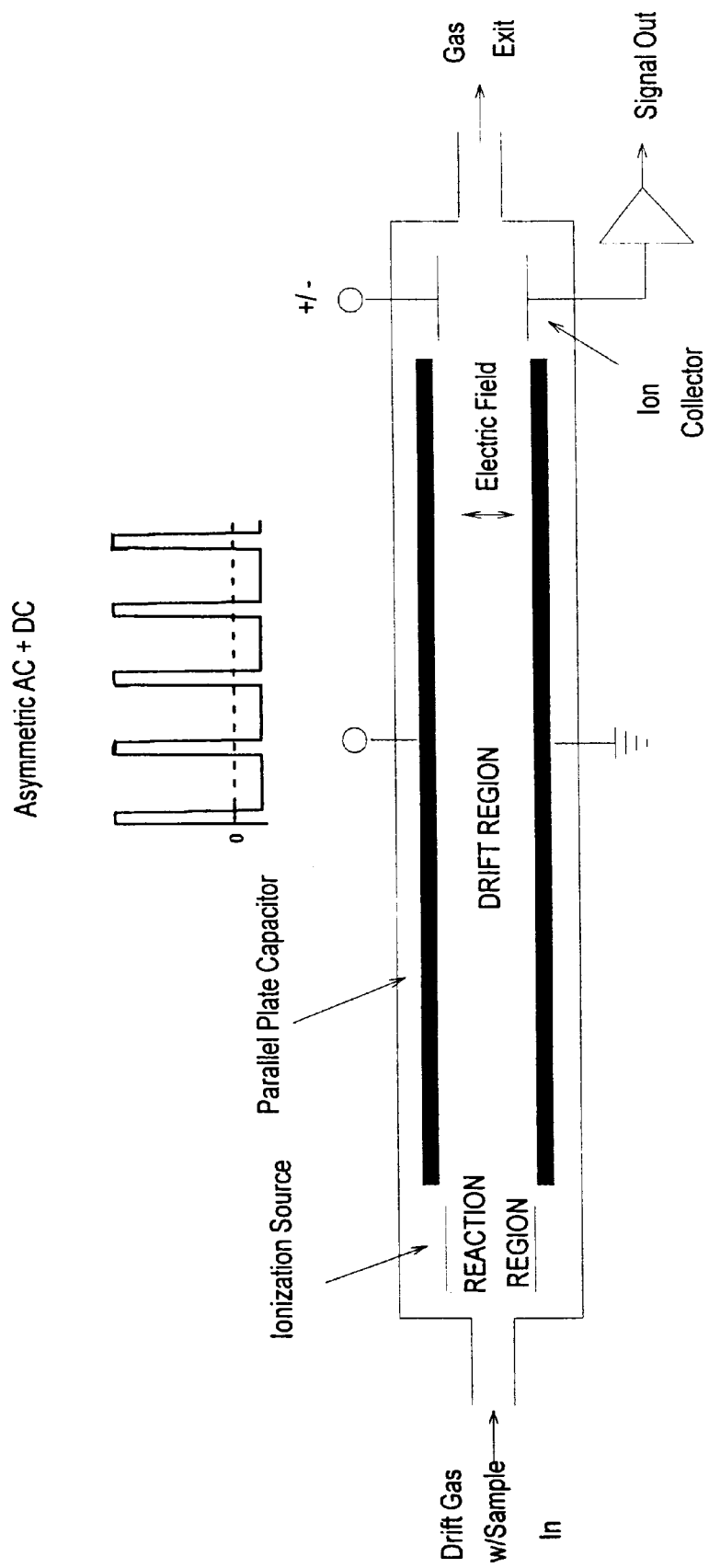
FIG. 3 is a simplified drawing for a parallel plate ion separator.
Figure 4:
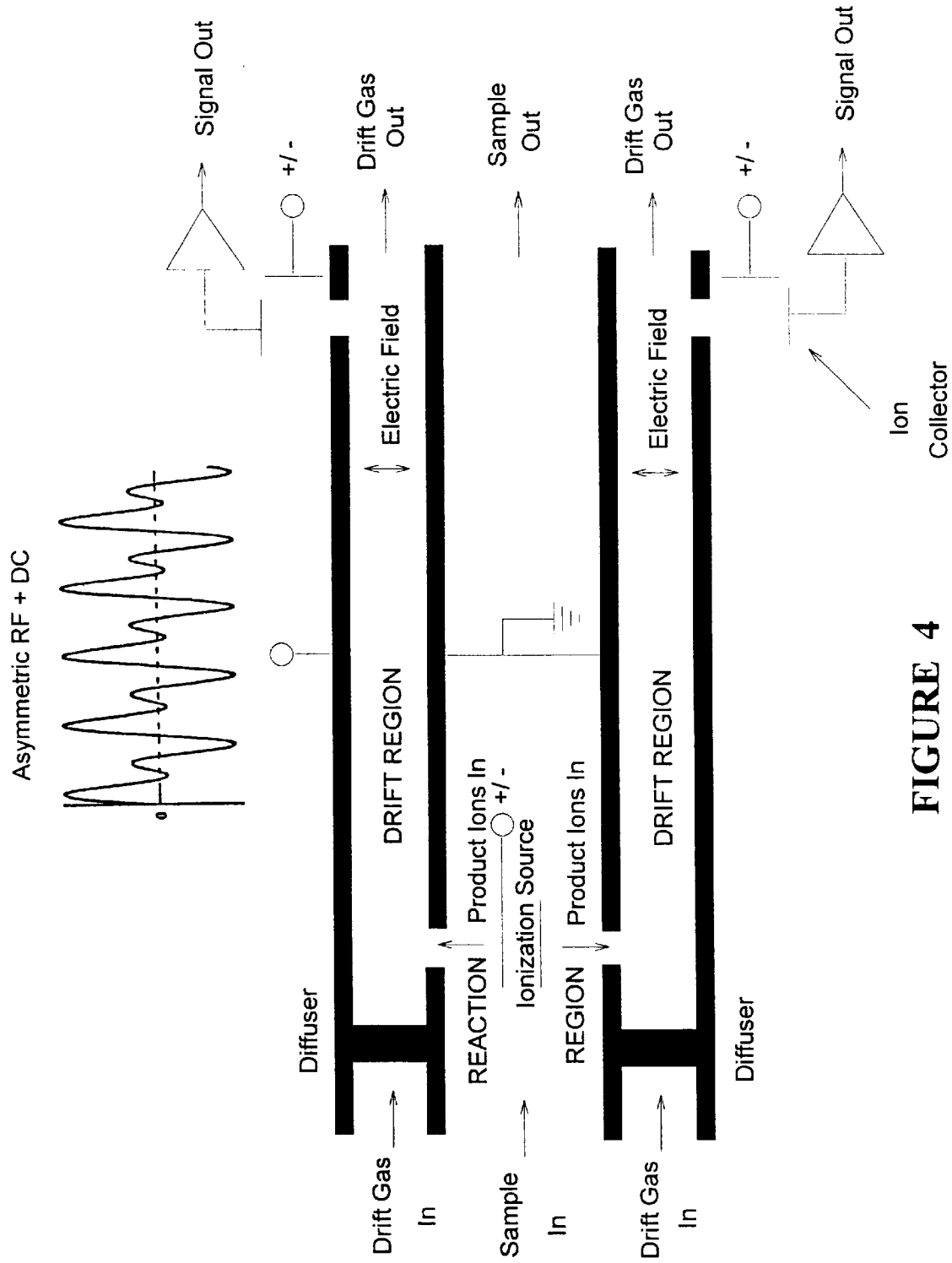
FIG. 4 is a simplified drawing for a later version of the parallel plate ion separator, known as the "Transverse Field Ion Mobility Spectrometer" or "Field Ion Spectrometer."
Figure 5:
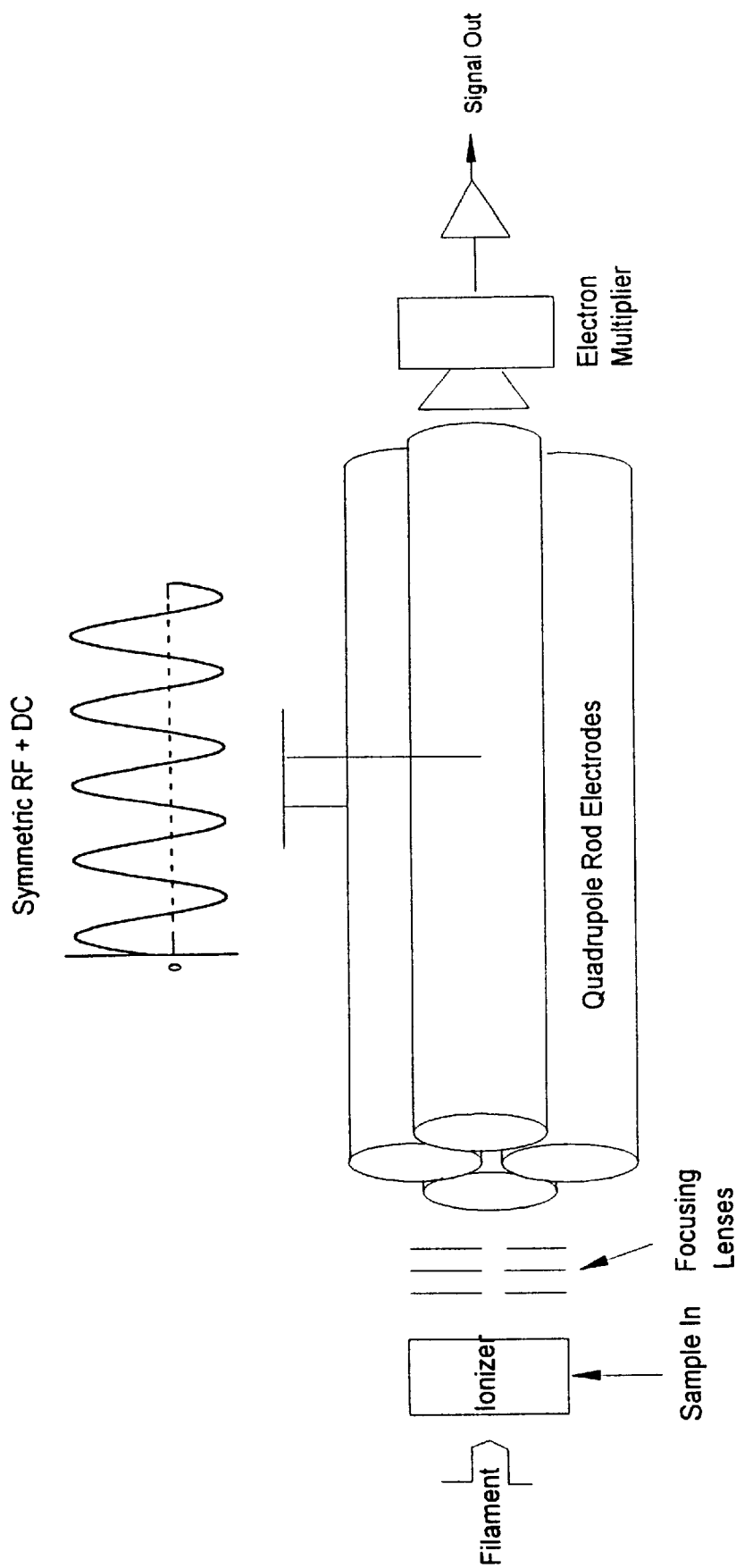
FIG. 5 is a simplified drawing illustrating the prior art for a quadrupole mass spectrometer.
Figure 6:
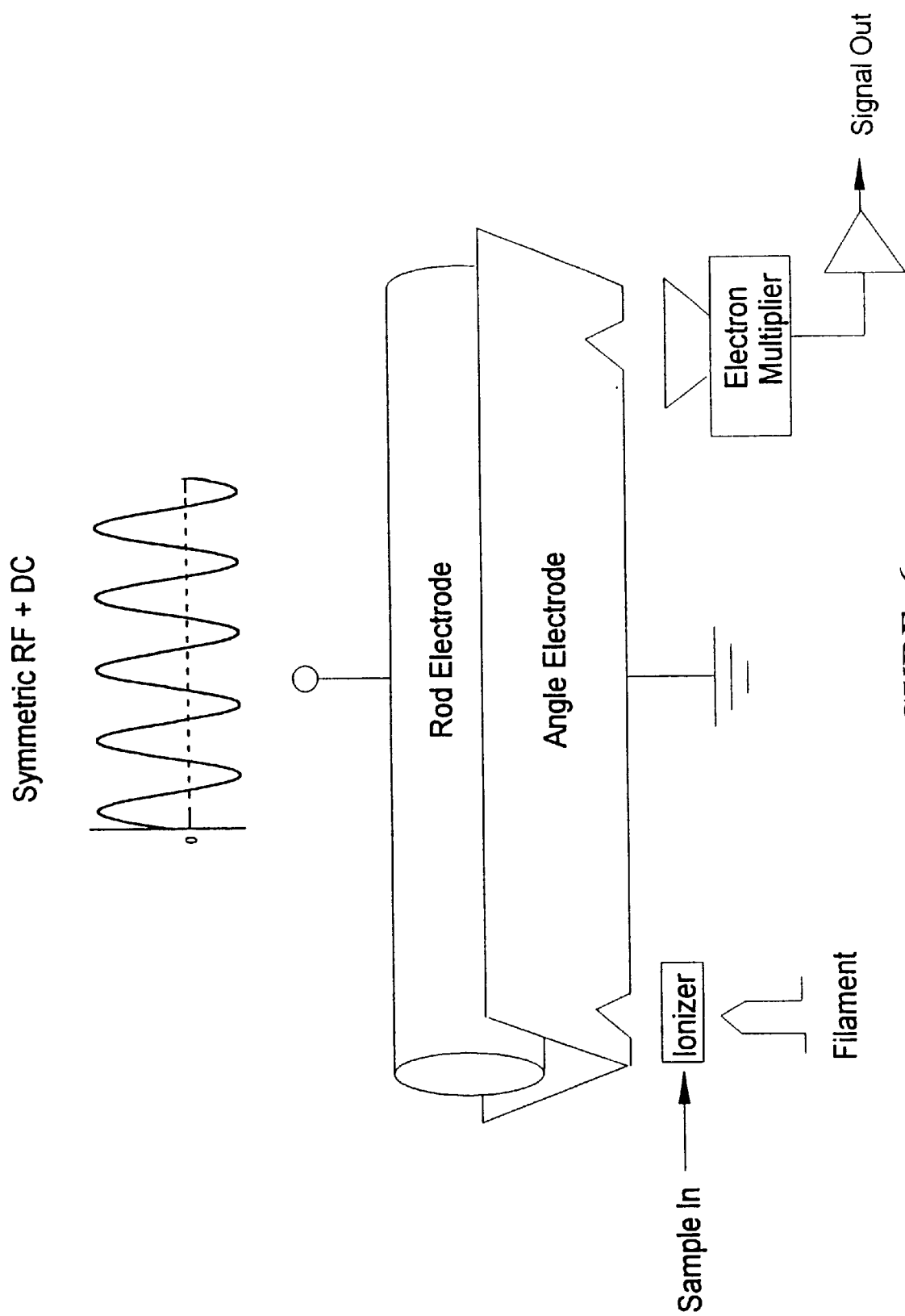
FIG. 6 is a simplified drawing illustrating the prior art for a monopole mass filter.
Figure 7:
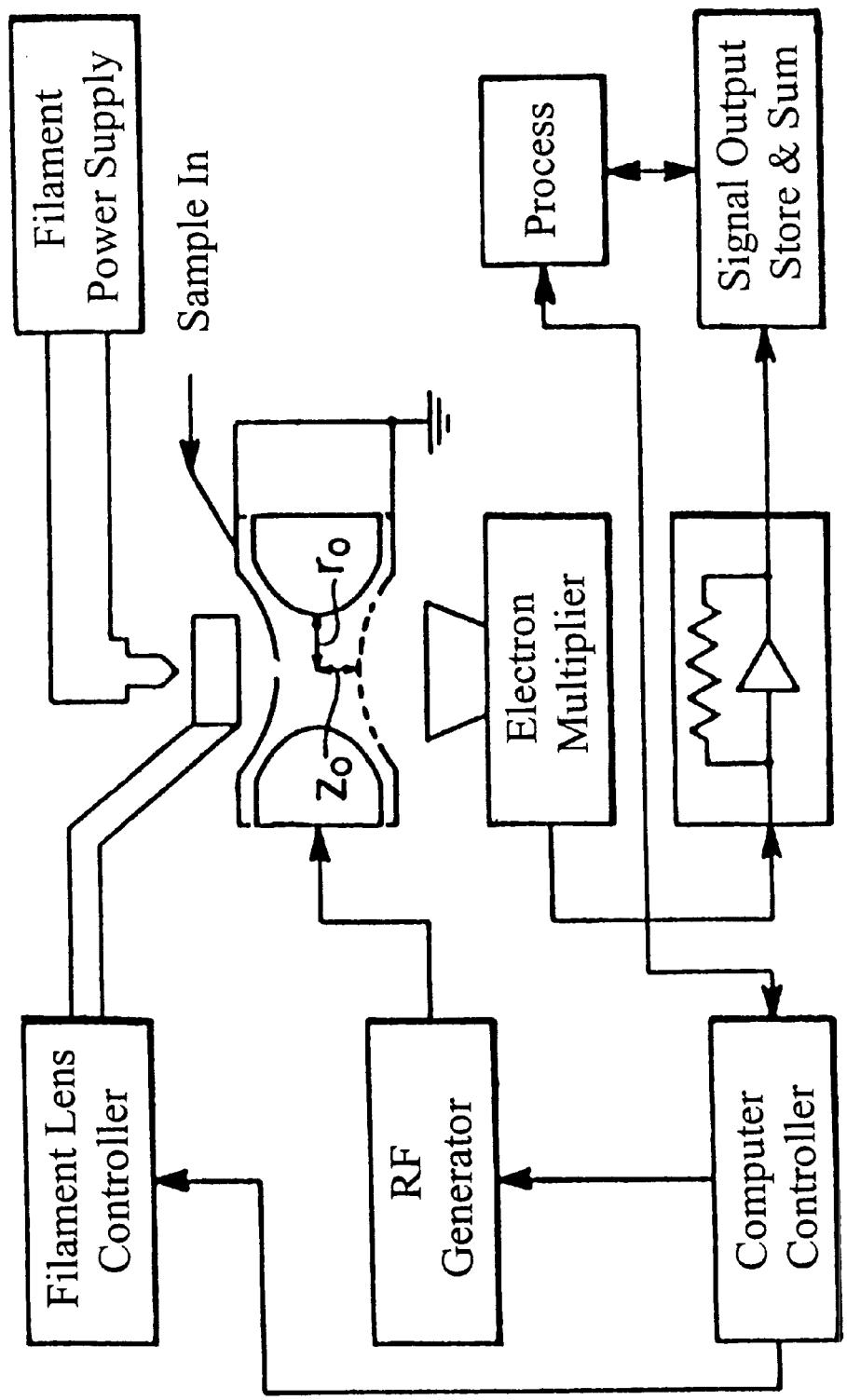
FIG. 7 is a simplified drawing illustrating the prior art for an ion trap mass spectrometer.
Figure 8A:
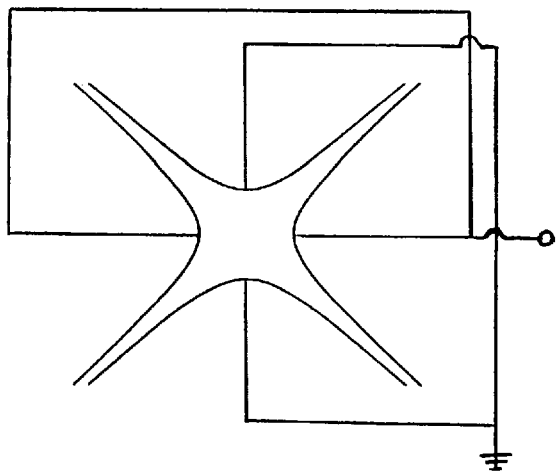
FIGS. 8A–8C show several electrode structures that might be used to generate a pure multipolar field; including the quadrupole (8A), hexapole (8B), and octapole (8C) fields.
Figure 8B:
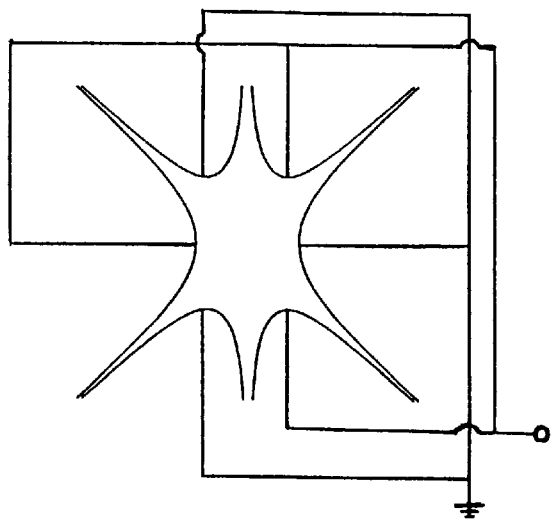
Figure 8C:
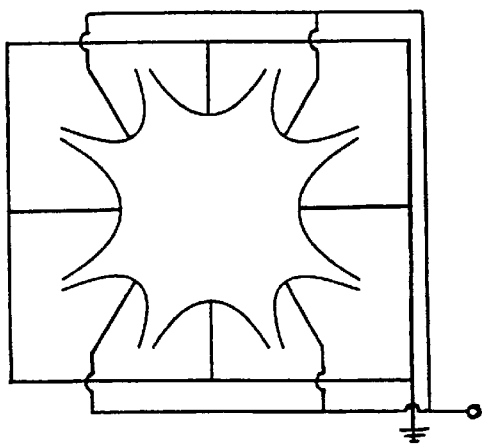
Figure 9A:
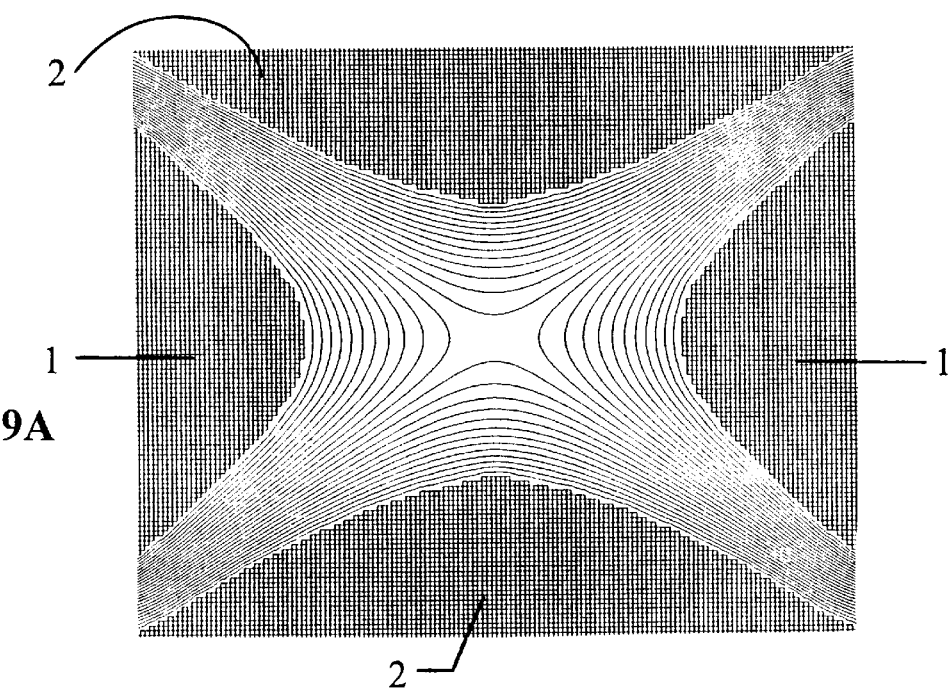
FIGS. 9A–9C show plots for the electrostatic equipotential field lines in a quadrupole ion trap (9A) and similar plots for planar traps (9B and 9C) designed to mimic the quadrupole ion trap.
Figure 9B:
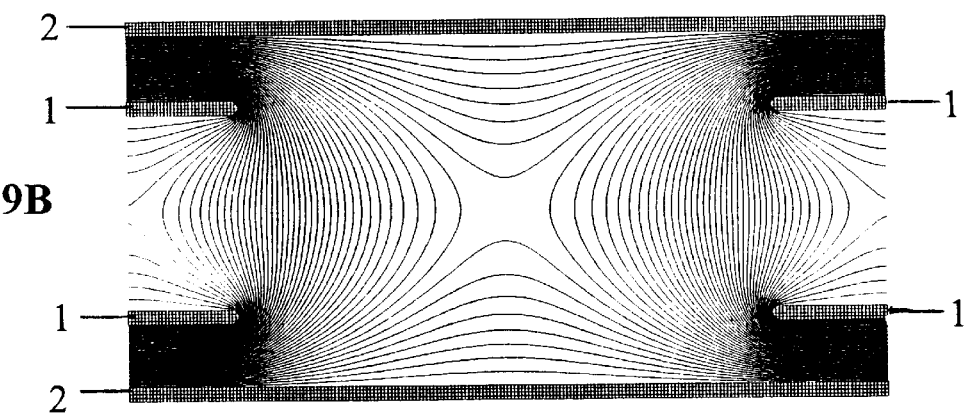
Figure 9C:
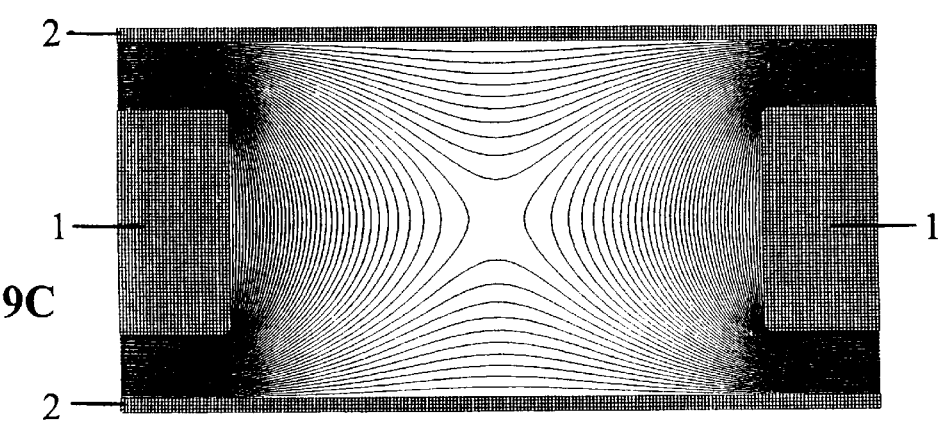

As will be obvious to those skilled in the art, the trap structure is not limited to the configuration of FIG. 15. Any device that creates a electromagnetic field in which, at least in one direction (e.g., along an axis), the strength of the field changes with location is equally suited. Such an electric field allows ions to be distributed along an axis at characteristic locations. Additionally, it is preferable that the equipotential lines of the electric field be an electrostatic focusing field so that the ions can be collected or stored at specific locations within the trap. Such a focusing field is created by designing an the electrode structure that has two or more poles. Because the device in FIG. 15 has four poles, it is known as a quadrupole ion trap. As discussed in connection with FIG. 9, a quadrupole field can be generated using a variety electrode structures. For purposes of this invention, each of these electrode structures are equally effective in separating ions in an ion mobility storage trap using the techniques just described. The traps illustrated in FIGS. 9B and 9C are advantageous from a manufacturing point of view in that their simple design would simplify fabrication. As discussed in connection with FIG. 8, other electrode structures can be used to produce higher order multipolar fields, or a linear combination thereof. Again for purposes of this invention, all these electrode structures are equally effective for trapping ions in an ion mobility storage trap. Because the functional dependence of the electric field upon location within the trap depends on the multipolarity of the field generated by the electrode structure, it is possible to adjust the range of ion mobilities stored in the trap by properly selecting and/or designing the electrode structure. This capability lies within the art associated with this invention.

Finally, FIG. 35 illustrates still other designs for an ion trap that works for the present invention. The equipotential lines displayed in FIG. 35 are again derived from SIMION, an electrostatic lens analysis and design program developed by D. C. McGilvery at LaTrobe University in Australia and extensively redesigned by D. A. Dahl at Idaho National Engineering Laboratories, Idaho Falls, Id. An analysis of the equipotential lines clearly shows that the traps produce a dipolar field in that only two poles are needed to describe the major features of the trap. A dipolar trap is not able to separate ions under vacuum conditions. However it is able to separate ions for the pressure conditions being considered for this invention. The results of FIGS. 16 and 24 to 34 show that only half of a quadrupole ion trap is needed to separate ions since the ion trajectories reside completely in the top half of the trap. Being half of a quadrupole ion trap, a dipolar trap may also be used to separate ions. Furthermore, the reduction in the number of parts to construct a dipolar trap simplifies its construction.

Figure 35A:
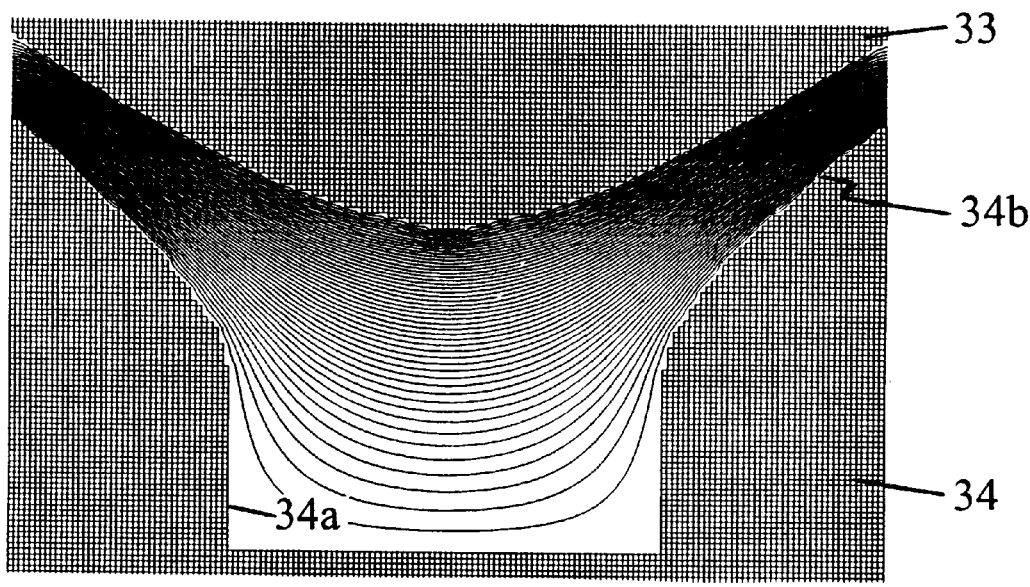
FIG. 35 shows SIMION plots for electrostatic equipotential field lines in a dipolar IMST.

FIG. 35A shows a hyperbolically shaped top electrode 33 separated from a bottom electrode 34. The bottom electrode 34 comprises a centrally located (symmetric[]al about the z-axis) rectangular well part 34a in a flange part 34b. Flange part 34b extends outwardly and upwardly towards electrode 33 from the edge of rectangular well part 34a. The dependence of the strength of the electric field on the z-coordinate is adjusted by adjusting the depth of the rectangular well part 34a.

Figure 35B:
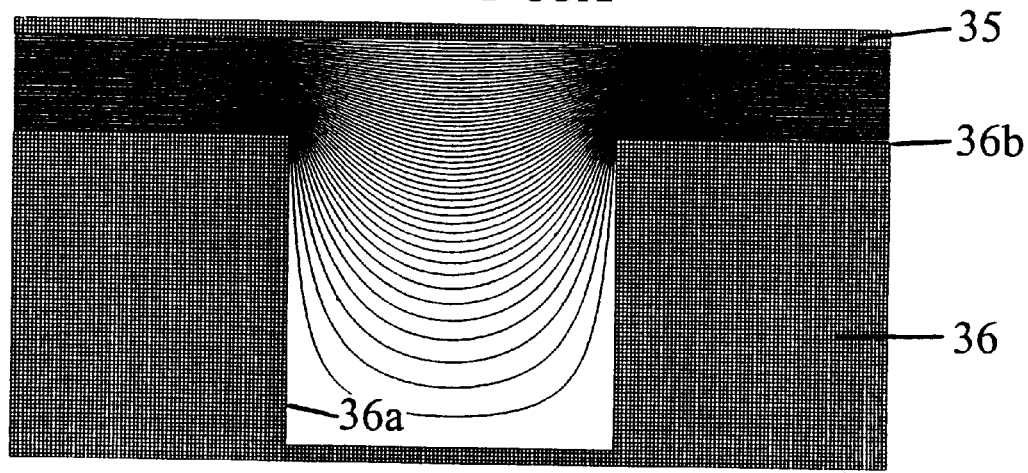

FIG. 35B shows a planar version of FIG. 35A. Replacing the hyperbolic top electrode is a flat plate 35 separated from the bottom electrode 36. The bottom electrode 36 includes a rectangular well part 36a and flange part 36b. Flange part 36b extends perpendicularly from the edges of rectangular well part 36a such that the surface of the flange part 36b is parallel with the opposing surface of top electrode 35. A comparison of the equipotential line profiles between FIGS. 35A and 35B shows that the simpler construction of the dipolar trap of FIG. 35B can be used to provide the same desired z-dependence for the electric field otherwise obtained by the more complex electrode structure of FIG. 35A.

Figure 35C:
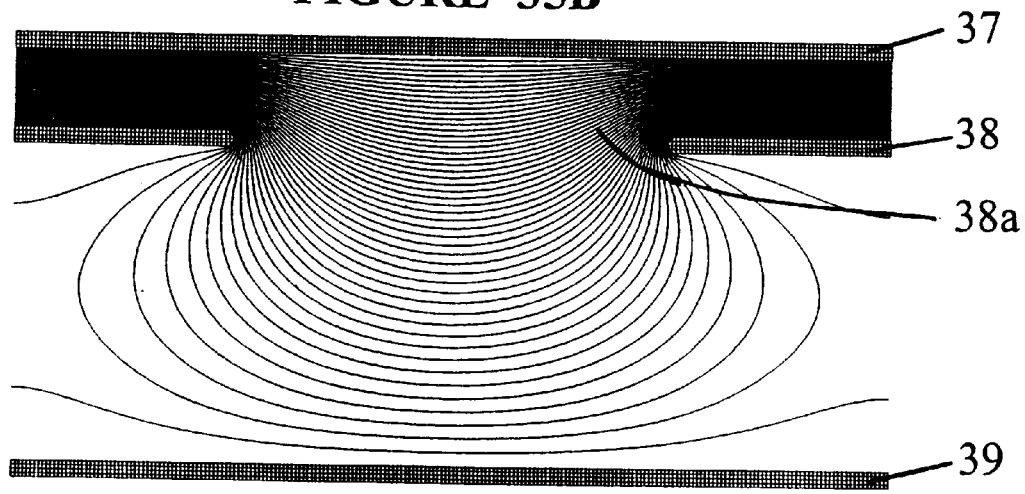

FIG. 35C shows still another example of a dipolar trap constructed using three parallel plates 37, 38 and 39. Plate 36 is interposed between plates 37 and 39. Top electrode is comprised of plate 37. Plates 38 and 39 comprise the bottom electrode and may be electrically connected to be held at the same potential. Plate 38 includes a circular hole 38a symmetrical about the z-axis thereby allowing an electric field to extend between plates 37 and 39 through hole 38a. Fringe fields radiating horizontally between plates 38 and 39 may cause defocussing of the ion cloud. This can be corrected by adding other plates (or another structure) between 38 and 39, if desired.

In FIG. 35, the sample is introduced into the traps by flowing a carrier gas through a hole in either of the top or bottom electrodes or through the space between the electrodes. Ions are removed along the z-axis through the top electrodes. The ionization of sample and the electrical biasing of the top and bottom electrodes is accomplished as described above.

Figure 36A:
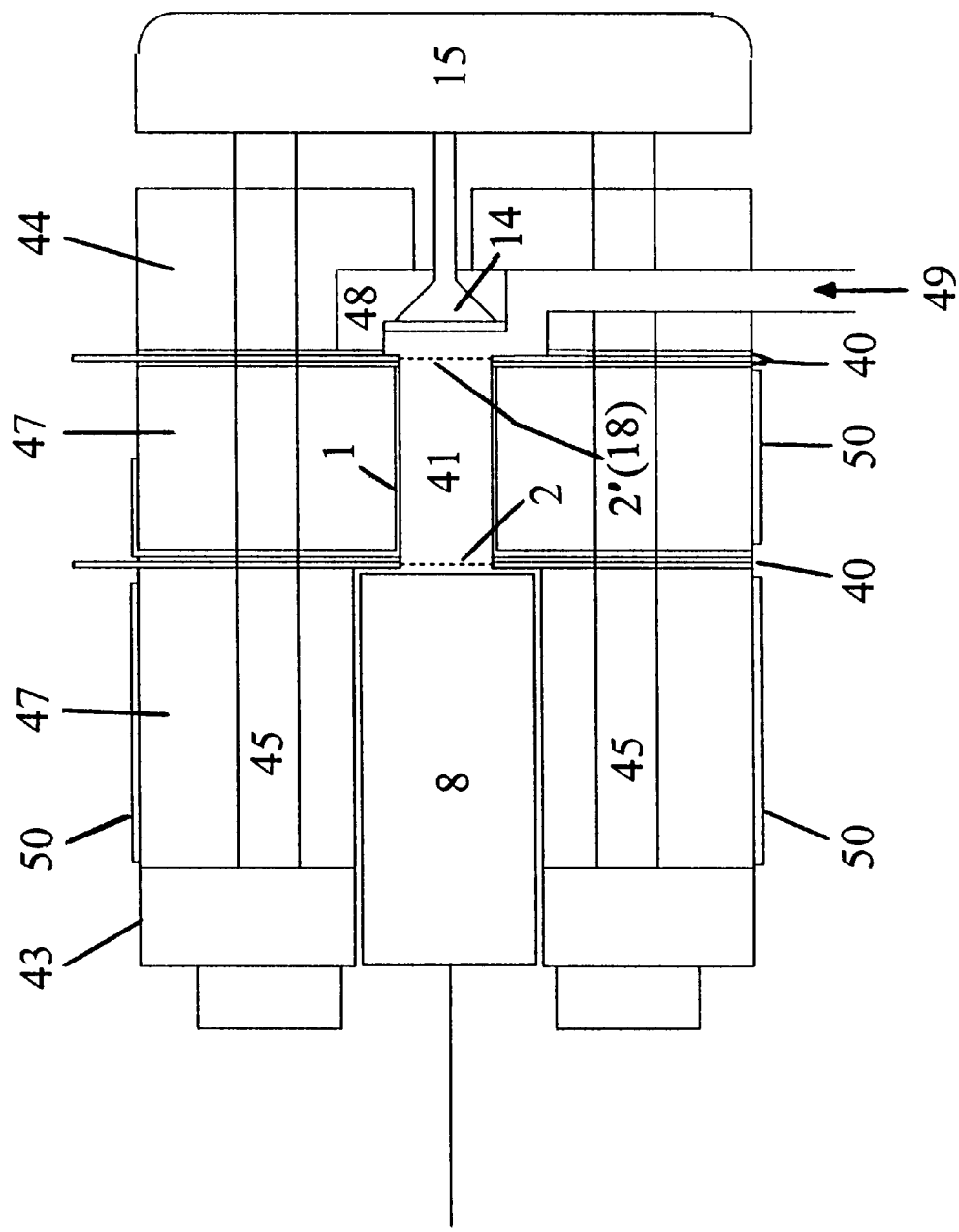

FIG. 36 shows an embodiment for a dipolar ion mobility storage trap that is compatible with a variety of ionization sources. FIG. 36A illustrates a pulsed photoionization lamp 8 coupled to a quadrupolar storage trap 41. The trap is a planar trap sandwiched between two metal flanges, 43 and 44, and clamped together using two or more support rods, 45. Two ceramic (e.g., Macor) blocks 47 position ring electrode 1 (for example, corresponding to electrode 1 in FIG. 9C) relative to end-cap electrodes 2 and 2' (for example, corresponding to electrodes 2 and 2' in FIG. 9C). Teflon sheet or ceramic paper/tape 40 is used to electrically insulate ring electrode 1 from the end-caps 2 and 2'. The end-cap electrodes are perforated to allow UV irradiation to enter the trap through end-cap electrode 2, and ions to leave the trap through end-cap electrode 2'. In this capacity, ring electrode 2' also serves as an aperture grid (for example, corresponding to 18 in FIG. 15). Ion collector 14 is mounted in ceramic (e.g., Macor) insulator 48 encapsulated in metal flange 44. Insulator 48 in combination with flange 44 also serves as a flow manifold for the sample 49 entering trap volume 41. After the sample is ionized in trap volume 41, it exits the trap by flowing around the exterior envelop of the photoionization flashlamp 8. Electrometer 15 is directly coupled to ion collector 14 to minimize pick-up of stray noise. Thick film resistor elements 50 are applied to the exterior surfaces of the ceramic trap for heating purposes.

FIG. 36B is a modification of the ion mobility storage trap of FIG. 36A where the photoionization flashlamp source 8 is replaced with a discharge ionization source. The discharge is located between electrodes 51 and 52 where the sample is ionized. Unlike the photoionization flashlamp source, the discharge between electrodes 51 and 52 does not irradiate volume 41 of quadrupole trap 41 of FIG. 36A. Consequently, trap 41 in FIG. 36B is shown as a dipolar trap. This allows ions to be injected through ring electrode 1 (including a grid for that purpose) and their removal through end-cap 2'. Electrodes 51 and 52 are biased relative to ring electrode 1 to cause the ions created in the discharge gap to migrate towards and enter trap volume 41 The ions enter trap volume 41 during at least a portion of the AC cycle applied to ring electrode 1. Ion injection may also be assisted by pulsing the potential applied to the discharge source or 1:he trap. Details for constructing the discharge ionization source are well-known to those skilled in the art. Electrode 51 is typically tungsten and electrode 52 may, for example, be a stainless steel capillary tube.

Figure 36C:
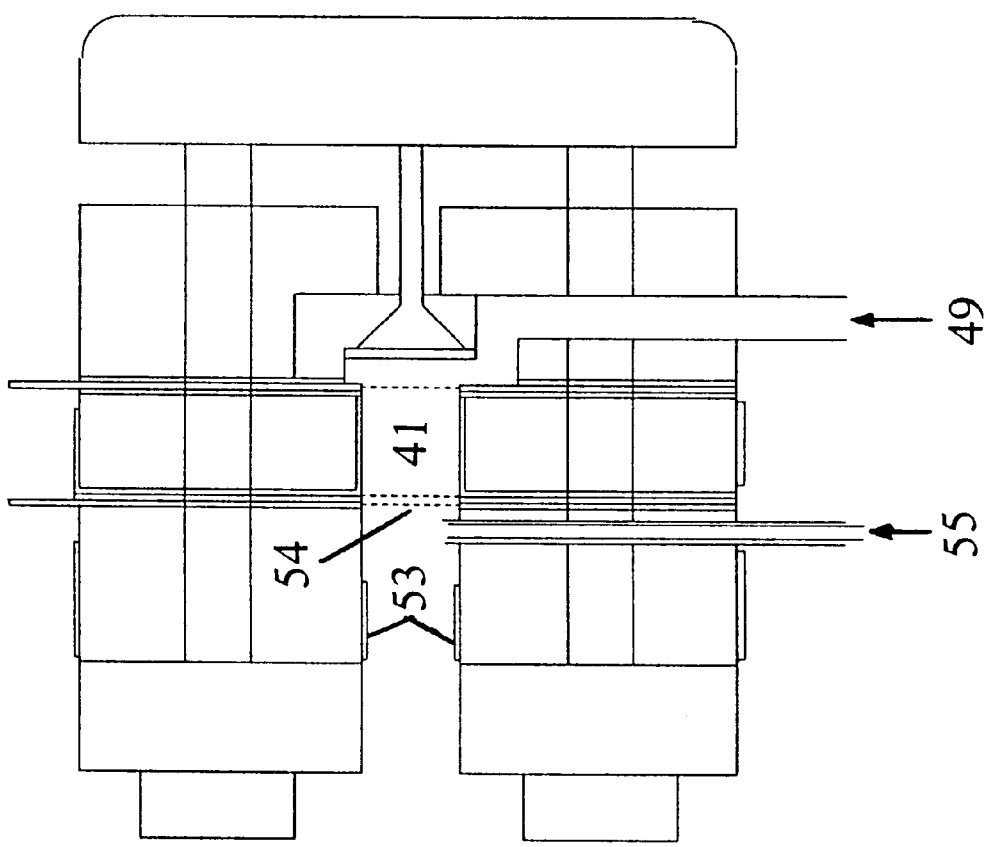

FIG. 36C is still another modification of the ion mobility storage trap of FIG. 36A where a radioactive source 53 is used for ionization instead of photoionization source 8. One example for a radioactive source is a $Ni^{63}$ isotope electroplated on a nickel foil. The $Ni^{63}$ isotope emits beta-particles that have sufficient energy to ionize gas contained in the irradiated source volume. Again because a radioactive source is unable to ionize gas in the full volume 41 of the quadrupole trap shown in FIG. 36A, a dipolar trap is shown in FIG. 36C. Shutter grid 54 is provided to assist in introducing ions into the trap. Sample can be introduced into the trap for ionization either through the collector manifold 49, or through orifice 55 leading directly into the irradiated volume containing radioactive source 53.

Sample can be introduced into the ion mobility storage traps (IMST's) of FIG. 36 using a variety of techniques. These include, but are not limited to, syringe injection, flash evaporation or desorption, purge and trapping, and membrane permeation of the sample into ports 49 or 55. Additionally a gas chromatographic column can be used to introduce sample into the trap. Gas chromatography is a technique whereby a sample is pre-separated into its component parts before it is delivered to a detector for detection. The pre-separation is accomplished by passing the sample through a column whose internal surface is coated with a polymerized "liquid" phase. As the sample passes through the column, its various components dissolve in the liquid phase and migrate through the column as the dissolution process competes with re-evaporation. As the sample components exit the column, they are presented to a detector for detection.

Figure 37:
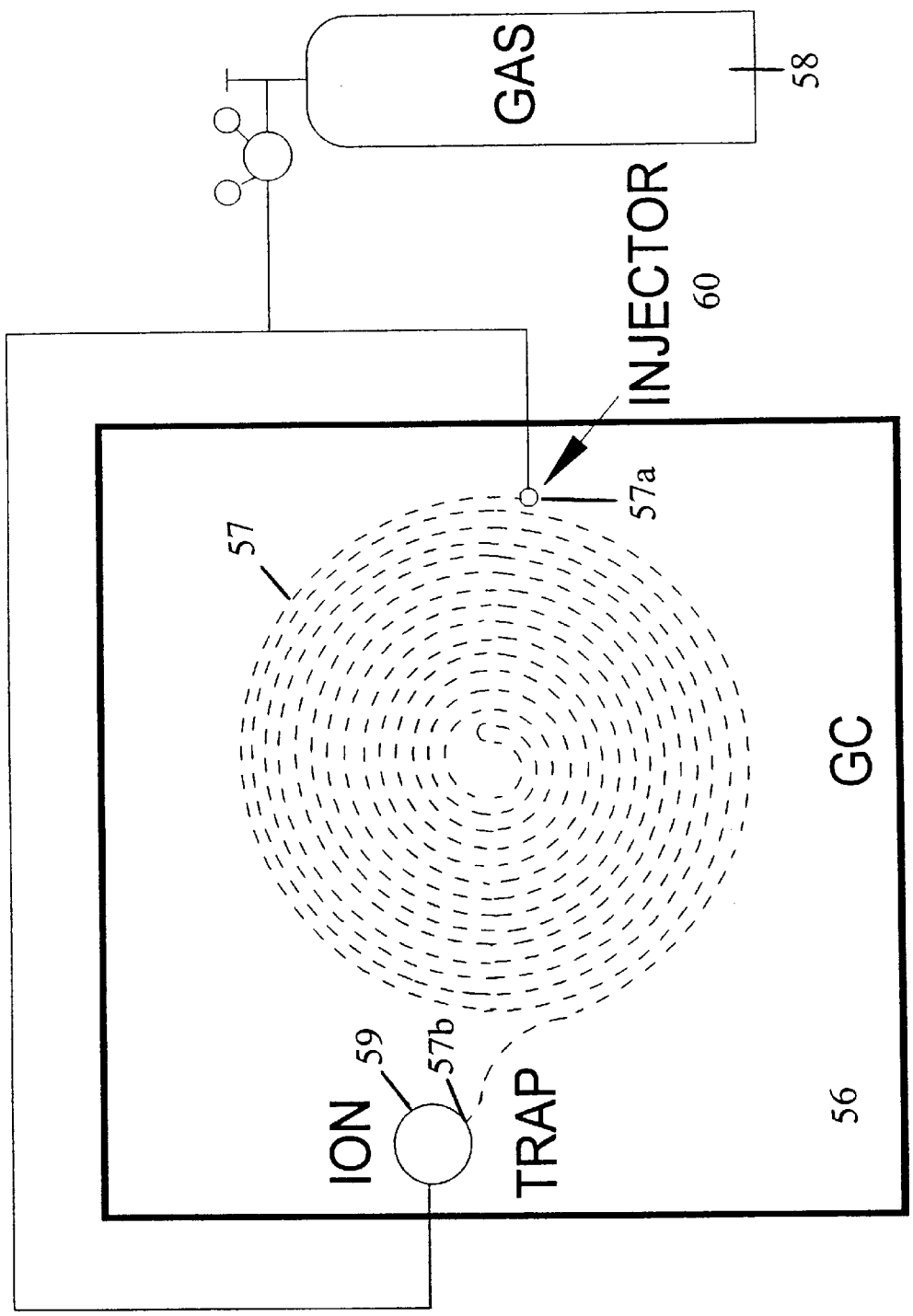
FIG. 37 shows an embodiment for the invention where an IMST is integrated with a gas chromatograph.

Such a gas chromatograph 56 is shown in FIG. 37 where gas chromatographic column 57 is shown delivering sample entrained in carrier gas 58 to one or more IMST's 59 (one is shown). The sample is introduced into the gas chromatographic column 57 by injector 60 at entrance 57a. As known to those skilled in the art of gas chromatography, the injector may be a syringe injector, a gas sampling loop, a purge-and-trap system, an aspirating inlet, or the like. After injection, the sample separates into its component parts as it partitions between the flowing carrier gas 60 and the stationary liquid phase. In FIG. 37, the path followed by the sample through the column is shown to first spiral into the center of gas chromatograph 58, and after reaching the center, spiraling back out. This is a satisfactory flow pattern, but others are also possible depending on how the gas chromatograph is constructed. As the sample components migrate through gas chromatographic column 57, they eventually exit the column and enter ion trap 59 through column exit 57b. Again as known to those skilled in the art of gas chromatography, column exit 57b may include a splitter to accommodate more than one IMST.

The gas chromatograph 56 of FIG. 37 may be a commercial chromatograph such as is manufactured by Hewlett Packard of Wilmington, Del.; Perkin Elmer of Norwalk, Conn.; Shimadzu Scientific Instruments of Columbia, Md.; Varian of Walnut Creek, Calif.; or SRI Instruments of Torrance, Calif. For these instruments, the IMST would be mounted on the heated detector block and the glass capillary column inserted into ports 49 or 55 of FIG. 36 for the IMST. Alternatively, the gas chromatograph 56 of FIG. 37 may be a micromachined column as described by S. C. Terry in a dissertation written in partial fulfillment for a Ph.D. degree from Stanford University in May, 1975. Terry disclosed procedures for fabricating a gas chromatographic column 57 by etching a groove in a silicon wafer, encapsulating the groove with a cover plate bonded to the silicon wafer, and coating the encapsulated groove (or column) with conventional coating techniques. His work is further described in *IEEE Transactions on Electron Devices*, volume ED-26 (December, 1979), pp. 1880–1886 and *Scientific American*, volume 248 (April, 1983), pp. 44–55; and was repeated by E. S. Kolesar, et al. in the *Journal of Microelectromechanical Systems*, volume 3 (1994), pp. 134–154. While Terry and Kolesar used wet chemical etching techniques to etch their column, those skilled in the art of microfabrication know that other approaches (such as reactive ion etching) to micromachining silicon are possible, particularly if deep etching is required. Sample is delivered to the IMST from a micromachined column by an capillary column extension or by including the miniature IMST on the micromachined silicon wafer.

Figure 38:
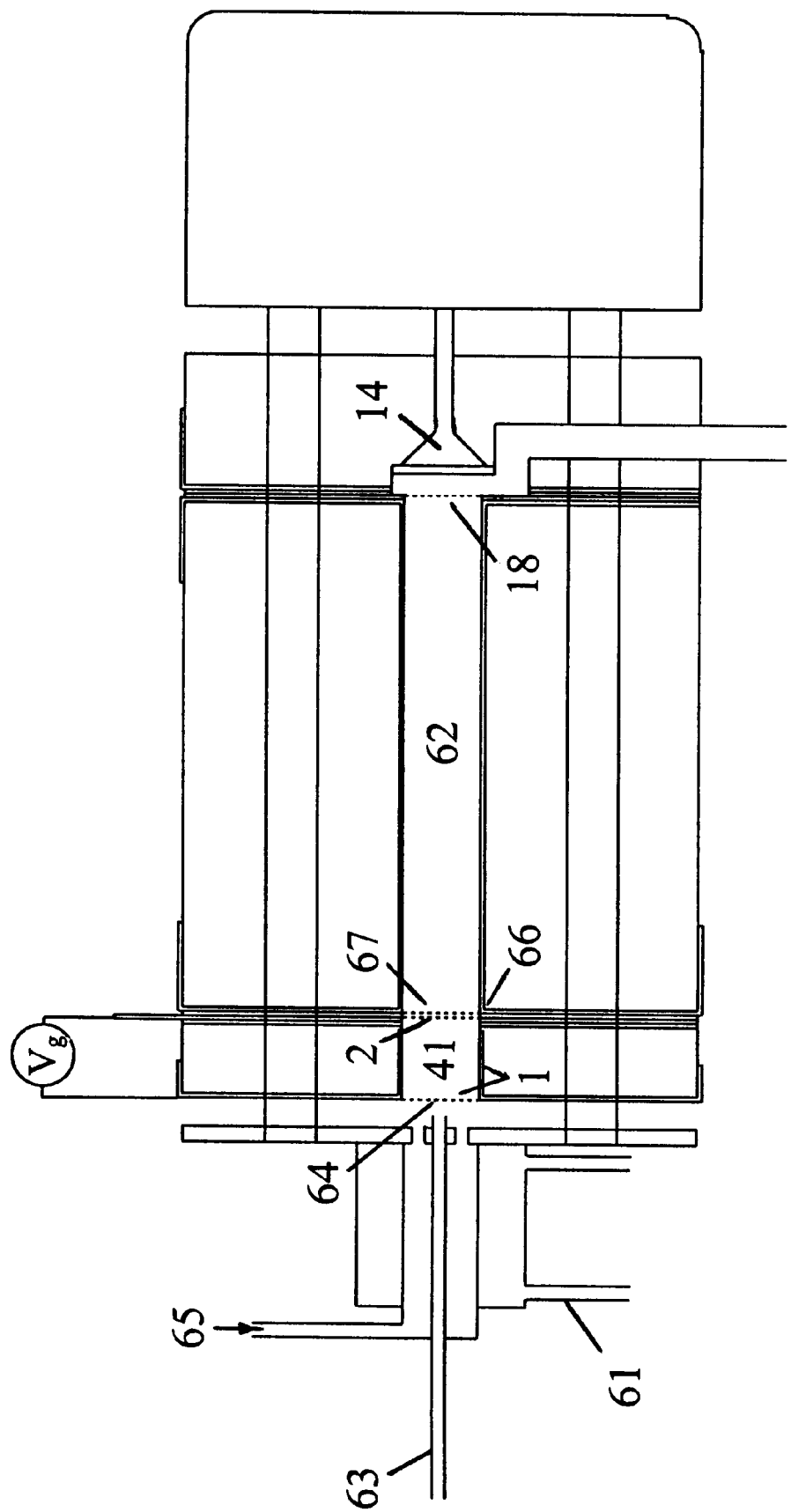
FIG. 38 shows an embodiment for the invention where a dipolar IMST is used to store ions from an electrospray ionization source and to introduce the stored ions into the drift tube of a linear IMS.

Another application for the IMST is as an ion storage device and electromagnetic lens to focus ions from an ionization source onto an ion separator. An embodiment for the invention demonstrating this flnction for the IMST is shown in FIG. 38. In FIG. 38. IMST 41 serves to desolvate ions generated by an electrospray ionization source and focuses the icons onto the drift tube 62 of a linear ion mobility spectrometer for additional analysis. Electrospray ionization mobility spectrometry is described by D. Wittmer, Y. H. Chen, B. K. Luckenbill, and H. H. Hill, Jr. in *Analytical Chemistry*, volume 66 (1994), pp. 2348–2355. An electrospray ionization source consists of a syringe needle 63 through which is passed an electrolyte, for example from a liquid chromatograph. As the electrolyte emerges from the syringe needle, it is exposed to a high electric field and the solvent stripping action of a curtain gas 65. In Wittner, et al.'s application, volume 41 is a buffer volume that provides additional time for desolvation before the ions are submitted to drift tube 62 for analysis. The present invention replaces buffer volume 41 with an IMST that helps desolvate the ions by oscillating them in asymmetric field. The dipolar IMST consists of ring electrode 1 (including grid 64) and end-cap electrode 2. Because a high potential is maintained between the electrospray ionization source 61 and grid 64, the ring electrode of the IMST is not the electrode excited with RF as in the other configurations for this invention. Rather the RF potential is applied to end-cap electrode 2 which additionally serves in combination with grid 67 as a shutter grid to introduce ions into drift tube 62. The ions are stored by using predetermined values for the AC and DC components of the potential applied across electrodes 1 and 2 by voltage generator Vg. The stored ions are pulsed out of the reactor by simultaneously applying an accelerating potential between grids 2 and 67, and increasing the DC component of voltage source Vg. By providing a delay between the time the DC component of voltage source Vg is increased and when the shutter grid 66 is opened, ions with a narrow range of mobilities can be introduced into linear drift tube. The linear drift tube may be, for example, a stacked-ring drift tube as initially described by J. H. Schummers, G. M. Thomson, D. R. James, I. R. Gatland E. W. McDaniel in *Physical Review A*, volume 7 (1973), pp. 683–688, or a ceramic drift tube containing an inlaid thick film resistor as described in U.S. Pat. No. 4,390,784 which issued on Jun. 28, 1983 to D. R. Browning, et al.

As the ions enter drift tube 62, they are attracted towards Faraday plate 14 due to a potential applied to grid 18. Because the drift tube is filled with a drift gas, the speed at which the ions travel through the drift tube is determined by their mobilities. The electric field produced within drift tube 62 is such that the mobilities of the ions are relatively constant, as compared to the mobilities of the ions within volume 41 of the IMST. As the ions hit Faraday plate 14, an ion current is generated. Based upon the time lapse between the opening of shutter grid 66 and the detection of the ion current, the ions may be identified.

Because the IMST can store ions, the solvated ions can be more effectively desolvated before they are introduced into the drift tube. Furthermore because the IMST accumulates ions, a greater number of ions can be introduced into drift tube 62. Additionally, ions with progressively increasing or decreasing mobilities can be delivered to drift tube 62 by the IMST to provide an greater resolution in determining mobilities. This resolution can be traded for a shorter drift tube that provides the same resolution as a conventional ion mobility spectrometer.

The embodiment of FIG. 38 can also be used without a shutter grid. For that configuration, grid 67 is removed. The asymmetric AC and DC voltage generator Vg then focuses and stores the ions at specific locations within trap volume 41, depending upon the mobility characteristics of the specific ions. When the asymmetric AC potential is removed and an accelerating potential is applied across electrodes 1 and 2, the ions are injected into drift tube 62 for subsequent mobility analysis.

Figure 39:
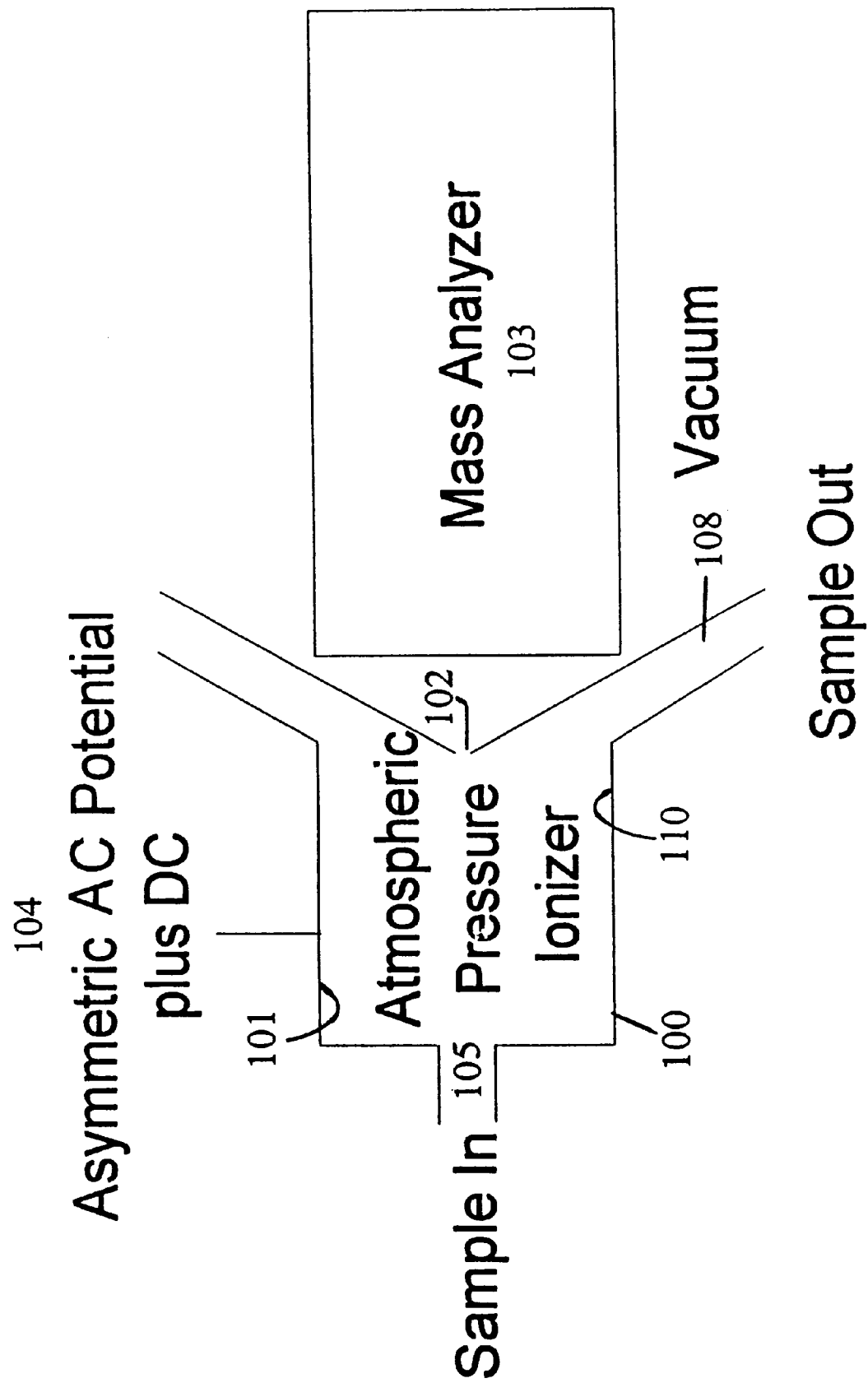
FIG. 39 shows an embodiment for the invention where a dipolar trap is integrated with an atmospheric pressure ionizer for a mass spectrometer.
Figure 40:
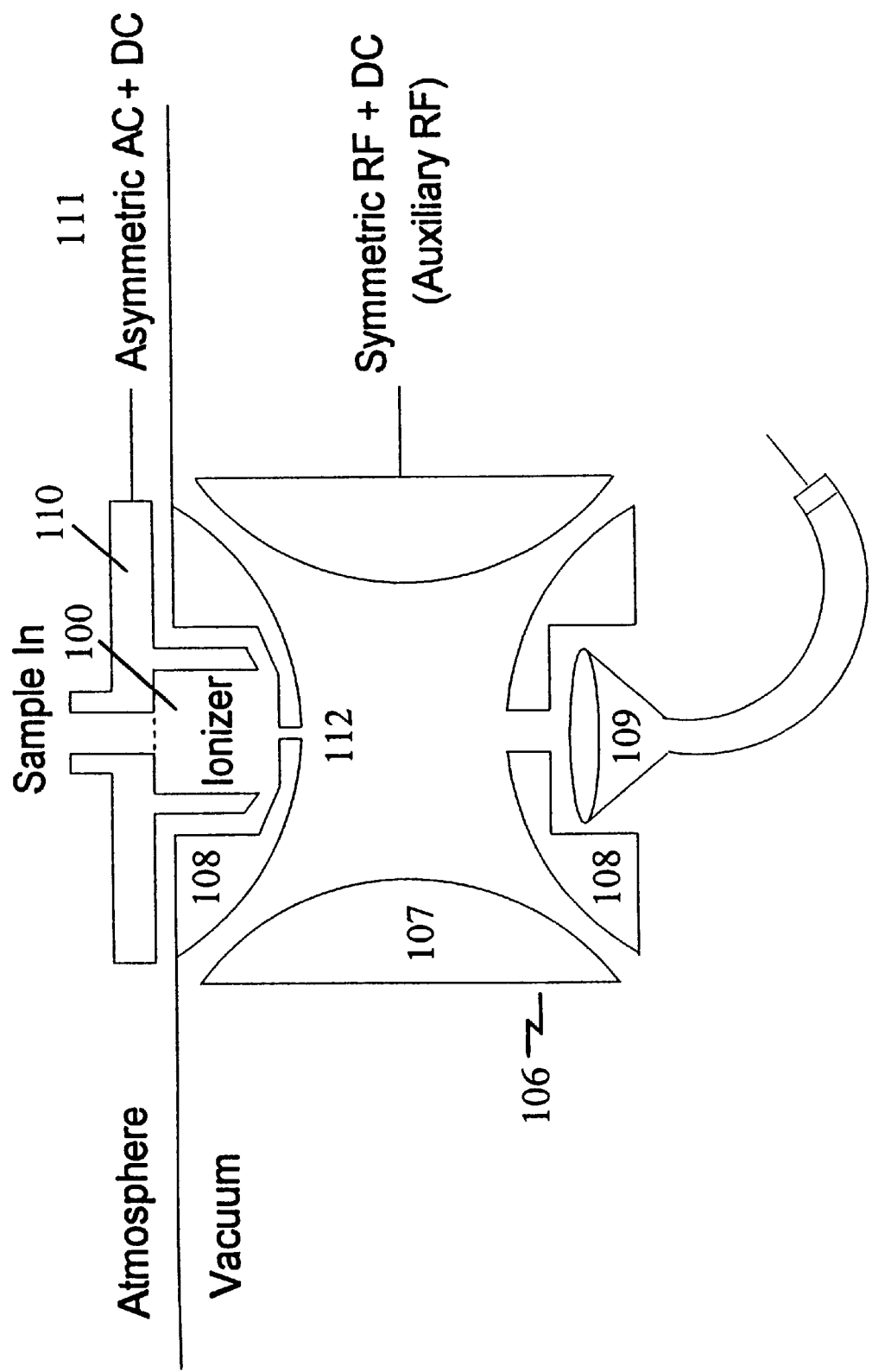
FIG. 40 shows the dipolar trap integrated with the ionizer of an ion trap mass spectrometer.

A final embodiment for the current invention is shown in FIGS. 39 and 40 where the dipolar IMST is coupled to a mass spectrometer as an atmospheric pressure ionizer. The atmospheric pressure ionizer 100 of FIG. 40 is similar to that disclosed by E. C. Horning, et al. in a paper published in *Analytical Chemistry*, volume 45 (1973), pp. 936–943. Ionizer 100 uses a radioactive source 101 (other ionization sources are possible) to ionize sample under atmospheric pressure conditions, and the ions are sampled through orifice 102 into the mass spectrometer 103. Because the mass spectrometer requires a hard vacuum for operation, such a system typically uses fast vacuum pumps to draw the ions through a 10 to 100 micron pinhole or tube into the mass spectrometer using flowing gas. With one exception, there is usually no provision to focusing the ions formed by ionizer 100 onto the ion sampling orifice 102 on the atmospheric pressure side. The exception is a corona discharge that enriches the ion concentration in the vicinity of the pinhole leading into the mass spectrometer. The current invention provides such a capability where a dipolar IMST is used to focus the ions onto the pinhole. The dipolar IMST comprises an electrode structure placed within atmospheric pressure ionizer 100 and a power source to apply an asymmetric AC and DC potential across the electrodes. Specifically, a first electrode 110 may define a majority of the atmospheric pressure ionizer chamber, while a second electrode 108 may define one side of the atmospheric pressure ionizer 100. The second electrode 108 includes pinhole 102. Under the influence of the applied asymmetric AC and DC potentials 104, the ions migrate toward the center of the ionizer 100 (i.e., r=0 or the z-axis which extends from orifice 102 to sample inlet 105) where they are introduced into orifice 102 by simply increasing the DC component of potential 104.

FIG. 41 shows an ionizer 100 similar that in FIG. 40 coupled to an ion trap mass spectrometer 106. The ion trap mass spectrometer consists of ring-electrode 107, end-car, electrodes 108, and electron multiplier 109. Applied to ring-electrode 107 is a symmetric AC plus DC potential that can be scanned to produce a mass spectrum as taught in U.S. Pat. No. 4,540,884 which issued on Sep. 10, 1985 to G. C. Stafford, P. E. Kelley and D. R. Stephens. In addition, an auxiliary AC can be applied to ring-electrode 107 to allow operation of the trap in MS/MS mode as taught by U.S. Pat. No. 4,736,101 which issued on Apr. 5, 1988 to J. E. P. Syka, J. N. Louris, P. E. Kelley, G. C. Stafford and W. E. Reynolds along with corrections describe by U.S. Pat. No. Revision 34,000 issued on Jul. 21, 1992. Ionizer 100 is a planar dipolar IMST including ring-electrode 110 and end-cap electrode 108. Asymmetric AC and DC potentials 111 are applied to the ring-electrode 110 to cause the ions to migrate to the center of dipolar IMST 100. The ions are then scanned through aperture 112 for mass analysis by the ion trap mass spectrometer 106 by increasing the DC component of potential 111.

Manufacturing of the above disclosed trap electrode structures may be performed by microfabrication. Microfabrication is advantageous in order that a lower voltage may be applied across the electrodes which is still able to produce an electric field of sufficient strength due to the proximity of the electrodes. The dipolar ion mobility storage traps illustrated in FIG. 35 are particularly suited for microfabrication due to their simple structure. As compared to other spectrometry devices, micromachining is especially easy as the electrode structure of the ion mobility storage traps does not need to be extremely precise. Chemical etching, plasma etching, laser etching and LIGA several examples of micromachining techniques that may be used to properly shape electrodes of the ion mobility storage traps.

In order to compensate for the lower amount of ions generated by a microfabricated storage trap (due to its size, e.g.), several microfabricated storage traps may be used in combination as an array. For example, the device illustrated in FIG. 37 may include a plurality of storage traps manufactured on a silicon wafer.

The above description of the examples of the invention describe :specific storage trap examples in combination with specific ion mobility storage trap systems (such as those illustrated in FIGS. 10A and 10B), in combination with specific ionization sources, and in combination with other spectrometry devices. Additional embodiments of the invention include the replacement of the described examples of the storage traps, the trap systems, the ionization sources and other spectrometry devices with any of the corresponding elements described elsewhere in the specification.

Also, the above description is intended only to exemplify the invention. Modifications and variations of these examples will be obvious to those skilled in the art which still achieve the spirit of this invention. For example, the above description describes two specific examples of systems which can be used to provide the appropriate voltages to traps. However, these examples may be replaced by any voltage source which achieves the appropriate electric field within a trap volume. In addition, the description of the trap structures are only several detailed examples; many different trap structures will be apparent to those skilled in the art which fall within the scope of this invention.

Also, the above description details the positioning or localizing of the ions along an axis (or along a line or curve), the separation of the ions and the storage of the ions with respect to several different examples. It is intended that any of the disclosed examples may be utilized to perform only one of these functions or any combination thereof. Similarly, it is intended that one or more of these functions may be encompassed by other devices which fall within the scope of this invention.

It is intended that any of the disclosed storage trap examples may be used with any voltage generation source, and/or any ion mobility storage trap system, and/or in combination with any of the disclosed spectrometry devices (such as the gas chromatographic column, the drift tube or mass spectrometer) and/or other spectrometry devices, and/ or with any type of ionization source. Many other modifications other than those specifically mentioned here will be obvious to those skilled in the art.

The above detailed descriptions of the examples of the invention are for illustrative purposes. Modifications and variations of these examples will be obvious to those skilled in the art which still achieve the spirit and scope of the present invention.

I claim:

1. A method of separating and storing ions, comprising:
(a) applying an electric field to a volume containing a neutrally charged carrier gas and ions; and
separating the ions in the volume containing the neutrally charged carrier gas according to type to temporarily fixed positions within the volume as a function of the electric field applied to the volume and mobility characteristics of the ions, the mobility characteristics of the ions resulting from multiple collisions of the ions with molecules of the neutrally charged carrier gas.

2. The method of claim 1, further comprising:
(b) removing the separated ions from the volume by changing the electric field applied to the volume to move the temporarily fixed positions.

3. The method of claim 1, wherein step (a) includes applying the electric field to the volume with a voltage, the voltage varying with respect to time in a periodic manner, the integral of the voltage over a period being equal to first value, and the shape of the waveform of the voltage being asymmetric about the first value.

4. The method of claim 1, wherein step (a) includes applying the electric field to the volume, the electric field varying with respect to time to change the mobility coefficient value of the ions at a first portion of the volume.

5. The method of claim 4, wherein step (a) includes applying the electric field to the volume, the electric field at a second portion of the volume maintaining a substantially constant mobility coefficient value of the ions.

6. The method of claim 4, wherein step (a) includes applying the electric field to the volume, the integral of the electric field with respect to time at a position within the volume equal to a first value, and the shape of a waveform of the electric field with respect to time being asymmetric about the first value.

7. The method of claim 6, wherein step (a) includes applying the electric field to the volume, a strength of the electric field changing as a function of position within the volume.

8. The method of claim 1, wherein the carrier gas is maintained at a pressure greater than or equal to $10^{-3}$ mm Hg.

9. The method of claim 1, wherein the carrier gas is maintained at a pressure greater than or equal $10^{-2}$ mm Hg.

10. The method of claim 1, wherein the carrier gas is maintained at atmospheric pressure.

11. The method of claim 1, wherein the carrier gas is maintained at greater than atmospheric pressure.

12. The method of claim 1, further comprising
(b) injecting a sample into the volume containing the carrier gas; and
(c) ionizing the sample to create the ions.

13. A method of separating and storing ions within a trap, the trap including at least two electrodes positioned about a trap volume containing a carrier gas, comprising:
(a) applying a voltage across the at least two electrodes creating an electric field within the trap volume, and separating and storing the ions according to a difference in mobility experienced by each ion as a function of a change in the electric field, the mobility of the ions resulting from multiple collisions of the ions with molecules of the carrier gas.

14. The method of claim 13, wherein step (a) includes applying a voltage periodically varying, the voltage having a DC component and an AC component, the AC component being asymmetrical.

15. The method of claim 14, further comprising:
(b) changing the DC component of the voltage to remove the ions from the trap volume.

16. The method of claim 14, further comprising:
(b) changing the AC component of the voltage to remove the ions from the trap volume.

17. The method of claim 13, further comprising:
(b) introducing a sample into the trap volume; and
(c) ionizing the sample to create the ions.

18. The method of claim 17, further comprising:
(b) repeating steps (b) and (c);
(e) removing the ions from the trap volume by changing the voltage applied across the electrodes; and
(f) identifying the ions removed from the trap volume.

19. The method of claim 18, wherein step (f) includes identifying an ion as a function of the DC and AC components of the voltage applied across the at least two electrodes when an ion current is measured.

20. The method of claim 19, wherein step (f) includes measuring the ion current with a Faraday plate.

21. The method of claim 18, wherein step (f) includes identifying an ion with a mass spectrometer.

22. The method of claim 18, wherein step (f) includes identifying an ion with a drift tube.

23. The method of claim 17, further comprising:
injecting the sample through a gas chromatographic column before step (a).

24. The method of claim 17, further comprising injecting the sample using one of the following techniques:
syringe injection;
purge and trap;
sample loop;
aspiration;
or membrane inlet.

25. The method of claim 13, wherein the at least two electrodes include a ring electrode having a surface which is a revolution of a hyperboloid, the ring electrode being symmetrical about an axis and first and second end-cap electrodes having hyperbolic surfaces positioned to face one another along the axis of symmetry of the ring electrode, the first and second end-cap electrodes being electrically connected at the same potential, and step (a) includes applying the voltage across the ring electrode and the first and second end-cap electrodes.

26. The method of claim 13, wherein the at least two electrodes constitute only first and second electrodes, and step (a) includes applying the voltage across the first and second electrodes.

27. The method of claim 26, wherein the first electrode is plate shaped and the second electrode includes a cylindrical interior surface symmetrical about an axis which is perpendicular to a planar surface of the plate shaped first electrode and a flat interior surface parallel and opposite to the plate shaped first electrode joined to the cylindrical interior surface.

28. The method of claim 26, wherein the first electrode is hyperbolically shaped, symmetrical about an axis, and the second electrode includes a cylindrical interior surface symmetrical about the axis and a flat interior surface parallel and opposite to the plate shaped first electrode joined to the cylindrical interior surface.

29. The method of claim 13, wherein the at least two electrodes include a plate shaped first electrode, a plate shaped second electrode having a circular hole therein, and a plate shaped third electrode, the second electrode being sandwiched between the first and third electrode, the first, second and third electrodes lying in substantially parallel planes, and the second and third electrodes being electrically connected to maintain the same potential, the first, second and third electrodes thereby creating a dipolar electric field.

30. The method of claim 13, wherein the at least two electrodes include first and second electrodes having disk shapes, and third and fourth electrodes having ring shapes, the first, second, third, and fourth electrodes positioned co-axially with the third and fourth electrodes positioned between the first and second electrodes, the first and second electrodes being electrically connected to maintain the same potential and the third and fourth electrodes being electrically connected to maintain the same potential.

31. The method of claim 13, wherein the at least two electrodes include first and second electrodes having a disk shape and a third electrode having a ring shape, the first, second, and third electrodes being co-axial, the first and second electrodes placed to surround the third electrode, the first and second electrodes being electrically connected to maintain the same potential.

32. The method of claim 13, wherein the at least two electrodes create a multipolar field selected from the group consisting of a dipolar field, a quadrupole field, a hexapole field, an octapole field, and a combination thereof.

33. The method of claim 13, wherein step (a) includes storing the ions within the trap volume such that ions are moved to equilibrium positions within the trap volume according to ion type and the ions of each type oscillate about the corresponding equilibrium position.

34. The method of claim 13, wherein step (a) includes storing the ions within the trap volume such that each ion in the trap volume is moved to an equilibrium position within the trap volume according to a difference in the mobility of the ion during periods corresponding to positive and negative phases of the voltage applied across the at least two electrodes.

35. The method of claim 34, wherein, in step (a), each equilibrium position associated with the ions lies on one axis of the trap volume.

36. An apparatus for separating and storing ions, comprising:
at least two electrodes positioned about a trap volume containing a neutrally charged gas; and
a voltage source connected to the at least two electrodes to apply a voltage varying with respect to time in a periodic manner, the integral of the voltage over a period being equal to first value, and the shape of the waveform with respect to time of the voltage being asymmetric about the first value; wherein
the at least two electrodes are shaped and positioned to create an electric field across the trap volume having an electric field strength that diminishes at least along a first direction and equipotential lines of the electric field curve about a line within the trap volume which is parallel to the first direction,
whereby the pressure of the gas is maintained in the trap volume such that movement of ions within the trap volume is dictated by the mobility of the ions, the mobility of the ions resulting from multiple collisions of the ions with molecules of the neutrally charged gas.

37. The apparatus of claim 36, further comprising:
an ionizer to ionize a sample introduced into the trap volume.

38. The apparatus of claim 36, further comprising:
an ionizer to ionize a sample exterior to the trap volume, the ionized sample being then introduced into the trap volume.

39. The apparatus of claim 6, wherein the voltage source includes an AC voltage generator outputting an AC voltage and a DC voltage generator outputting a DC voltage, the voltage applied to the at least two electrodes comprising a combination of the AC voltage and the DC voltage.

40. The apparatus of claim 39, wherein at least one of the AC voltage generator and the DC voltage generator is controlled to remove ions from the trap volume.

41. The apparatus of claim 40, wherein the DC voltage generator is controlled to slowly increase the DC voltage component of the voltage applied to the at least two electrodes to remove ions from the trap volume.

42. The apparatus of claim 39, further comprising:
a Faraday plate positioned at an exit of the trap volume; and
a logic circuit identifying an ion as a function of the DC and AC components of the voltage applied across the at least two electrodes when an ion current generated by an ion contacting the Faraday plate is measured.

43. The apparatus of claim 36, further comprising:
means for applying a large potential to at least one of the at least two electrodes to remove all ions within the trap volume simultaneously.

44. The apparatus of claim 36, further comprising:
a mass spectrometer positioned at an exit of the trap volume, identifying ions which have exited the trap volume.

45. The apparatus of claim 36, further comprising:
a drift tube positioned at an exit of the trap volume, identifying ions which have exited the trap volume.

46. The apparatus of claim 36, further comprising:
a gas chromatographic column positioned at an entrance of the trap volume, preliminarily separating components of a sample before introducing the sample components into the trap volume.

47. The apparatus of claim 36, wherein the at least two electrodes include a ring electrode having a surface which is a revolution of a hyperboloid, the ring electrode being symmetrical about an axis, and first and second end-cap electrodes having hyperbolic surfaces positioned facing one another along the axis of symmetry of the ring electrode, the first and second end-cap electrodes being electrically connected at the same potential, and the voltage source applies the voltage across the ring electrode and the first and second end-cap electrodes.

48. The apparatus of claim 36, wherein the at least two electrodes constitute only first and second electrodes, and the voltage source applies the voltage across the first and second electrodes.

49. The apparatus of claim 48, wherein the first electrode is plate shaped and the second electrode includes a cylindrical interior surface symmetrical about an axis which is perpendicular to a planar surface of the plate shaped first electrode and a flat interior surface parallel and opposite to the plate shaped first electrode joined to the cylindrical interior surface.

50. The apparatus of claim 48, wherein the first electrode is hyperbolically shaped, symmetrical about an axis, and the second electrode includes a cylindrical interior surface symmetrical about the axis and a flat interior surface parallel and opposite to the plate shaped first electrode joined to the cylindrical interior surface.

51. The apparatus of claim 36, wherein the at least two electrodes include a plate shaped first electrode, a plate shaped second electrode having a circular hole therein, and a plate shaped third electrode, the second electrode being sandwiched between the first and third electrode, the first, second and third electrodes lying in substantially parallel planes, and the second and third electrodes being electrically connected to maintain the same potential, the voltage source applied across the first, second and third electrodes to thereby create a dipolar electric field.

52. The method of claim 36, wherein the at least two electrodes include first and second electrodes having disk shapes, and third and fourth electrodes having ring shapes, the first, second, third, and fourth electrodes positioned co-axially with the third and fourth electrodes positioned between the first and second electrodes, the first and second electrodes being electrically connected to maintain the same potential and the third and fourth electrodes being electrically connected to maintain the same potential.

53. The method of claim 36, wherein the at least two electrodes include first and second electrodes having a disk shape and a third electrode having a ring shape, the first, second and third electrodes being co-axial, the first and second electrodes placed to surround the third electrode, the first and second electrodes being electrically connected to maintain the same potential.

54. The apparatus of claim 36, wherein the at least two electrodes create a multipolar field selected from the group consisting of a dipolar field, a quadrupole field, a hexapole field and an octapole field and a combination thereof.

55. The apparatus of claim 36, wherein the pressurized gas is maintained at a pressure greater than or equal to $10^{-3}$ mm Hg within the trap volume.

56. The apparatus of claim 36, wherein the pressurized gas is maintained at a pressure greater than or equal to $10^{-2}$ mm Hg within the trap volume.

57. The apparatus of claim 36, wherein the pressurized gas is maintained at atmospheric pressure within the trap volume.

58. The apparatus of claim 36, wherein the pressurized gas is maintained at greater than atmospheric pressure within the trap volume.

59. An apparatus for storing ions, comprising:
a container containing a neuturally charged gas and ions; and
electric field generating means for generating an electric field to move the ions to corresponding equilibrium positions within the container according to ion type and for oscillating the ions of each type about the corresponding equilibrium positions, at least two of the corresponding equilibrium positions being different from each other.

60. The apparatus of claim 59, further comprising:
at least two electrodes within the container; and
a voltage source, applying a voltage across the at least two electrodes; and
wherein the moving means moves each ion to an equilibrium position within the container according to a difference in the mobility of the ion during periods corresponding to positive and negative phases of the voltage applied across the at least two electrodes.

61. An apparatus comprising:
a container containing a neutrally charged gas and ions;
electric field generating means for generating an electric field to move the ions to equilibrium positions along an axis within the container such that the ions oscillate about the equilibrium positions along the axis according to mobility characteristics of the ions, the mobility characteristics of the ions resulting from multiple collisions of the ions with molecules of the neutrally charged gas, at least two of the equilibrium positions being different from each other.

62. A method of collecting ions, comprising:
(a) applying an electric field to a volume containing a neutrally charged carrier gas and ions; and
(b) converging the ions toward convergent points corresponding to the ion type, as a function of the electric field applied to the volume and mobility characteristics of the ions, the mobility characteristics of the ions resulting from multiple collisions of the ions with molecules of the neutrally charged carrier gas.

63. The method of claim 62, wherein step (a) includes varying the electric field strength of the electric field applied to the volume and step (b) includes converging the ions as a function of a difference of mobility experienced by each ion due to a difference in electric field strength of the electric field applied to the volume in step (a).

64. The method of claim 62, wherein step (b) includes converging the ions to convergent points located within the volume.

65. The method of claim 62, further comprising:
analyzing the ions in a spectrometer; and
wherein step (b) includes converging the ions towards an ion sampling entrance of the spectrometer.

66. The method of claim 65, wherein the spectrometer is a mass spectrometer and the ion sampling entrance is a pinhole aperture of the mass spectrometer.

67. The method of claim 65, wherein the spectrometer is an ion mobility spectrometer.

68. The method of claim 67, wherein the ion mobility spectrometer is a drift tube.

69. A method of separating and converging ions within a trap, the trap including at least two electrodes positioned about a trap volume containing a carrier gas, comprising:
(a) applying a voltage across the at least two electrodes creating an electric field within the trap volume, and
(b) separating and converging the ions according to a difference in mobility experienced by each ion as a function of a change in the electric field, the mobility of the ions resulting from multiple collisions of the ions with molecules of the carrier gas.

70. The method of claim 69, wherein step (b) includes collecting the ions to temporary equilibrium positions within the trap.

71. The method of claim 69, wherein step (b) includes converging the ions to an entrance of a mass spectrometer, and the method further comprises (c) detecting the ions with the mass spectrometer.

72. The method of claim 69, wherein step (b) includes converging the ions towards an axis within the trap volume.

73. The method of claim 72, wherein step (b) includes collecting the ions along the axis within the trap volume.

74. The method of claim 73, wherein step (b) includes collecting the ions at corresponding equilibrium positions along the axis within the trap volume.

75. The method of claim 74, wherein the axis is the axis of symmetry of the trap volume.

* * * * *